US006962973B1

(12) United States Patent
Brown et al.

(10) Patent No.: US 6,962,973 B1
(45) Date of Patent: Nov. 8, 2005

(54) PORCINE α₂δ-1 CALCIUM CHANNEL SUBUNIT CDNA AND SOLUBLE SECRETED α₂δ-1 SUBUNIT POLYPEPTIDES

(75) Inventors: Jason Peter Brown, Stapleford (GB); Nicolas Steven Gee, Dundee (GB)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/397,548

(22) Filed: Sep. 16, 1999

(51) Int. Cl.⁷ .................... C07K 14/00; C07K 14/705
(52) U.S. Cl. ................................... 530/350; 530/402
(58) Field of Search .............................. 530/350, 402

(56) References Cited

U.S. PATENT DOCUMENTS

| 5,429,921 A | 7/1995 | Harpold et al. |
| 5,846,757 A | 12/1998 | Harpold et al. |

FOREIGN PATENT DOCUMENTS

| WO | 93/04083 | 3/1993 |
| WO | WO 00/20450 A2 | 4/2000 |

OTHER PUBLICATIONS

Gee, N.S., et al., The Journal of Biological Chemistry, The Novel Anticonvulsant Drug, Gabapentin (Neurontin), Binds to the Alpha2Delta Subunit of a Calcium Channel, 1996, vol. 271:10, pp. 5768–5776.

Brown, J.P., et al., The Journal of Biological Chemistry, "Cloning and Deletion Mutagenesis of the Alpha2Delta Calcium Channel Subunit From Porcine Cerebral Cortex", 1998, vol. 273:39, pp. 25458–25465.

Kowalski, M.T., et al. Biochemical Society Transactions, "Effects of Anti–Calcium Channel A2–Subunit Antibodies on Calcium Flux and 1,4–Dihydropyridine Binding" 1990, p. 890.

Gurnett, C.A., et al., The J. of Biological Chemistry, "Extracellular Interaction of the Voltage–Dependent CA2+ Channel Alpha2Delta and Alpha1 Subunits", 1997, 272:29 pp 18508–18512.

Gurnett, C.A., et al., Neuron, "Dual Function of the Voltage–Dependent CA2+ Channel Alpha2Delta Subunit in Current Stimulation and Subunit Interaction" 1996, vol. 16, pp 431–440.

Felix, R., et al., J. of Neuroscience, "Dissection of Functional Domains of the Voltage–Dependent CA2+ Channel Alpha2Delta Subunit", 1997, vol. 17:18, pp. 6884–6891.

Field, M.J., et al., British Journalof Pharmacology, "Gabapentin (Neurontin) and S–(+)–3–Isobutylgaba Represent a Novel Class of Selective Antihyperalgesic Agents", 1997, vol. 121, pp. 1513–1522.

Klugbauer, N., et al., The Journal of Neuroscience, "Molecular Diversity of the Calcium Channel Alpha2Delta Subunit", 1999, vol. 19:2, pp. 684–691.

Tokumaru, H., et al., European Journal of Pharmacology–Molecular Pharmacology Section, "Purification of the Cardiac 1,4–Dihydropyridine Receptor Using Immunoaffinity Chromatography With a Monoclonal Antibody Against the Alpha2Delta Subunit of the Skeletal Muscle Dihydropyridine Receptor" 1992, vol. 227, pp. 363–370.

Hill, D.R., et al., European Journal of Pharmacology–Molecular Pharmacology Section, "Localization of [3H]Gabapentin to a Novel Site in Rat Brain: Autoradiographic Studies", 1993, vol. 244, pp. 303–309.

Dissanayake, V.U.K., et al., British Journal of Pharmacology, "Spermine Modulation Fo Specific [3H]–Gabapentin Binding to the Detergent–Solubilized Porcine Cerebral Cortex Alpha2Delta Calcium Channel Subunit" 1997, vol. 120, pp. 833–840.

Brickley, K., et al., FEBS Letters, "Use of Site–Directed Antibodies to Probe the Topography of the Alpha2 Subunit of Voltage–Gated CA2+ Channels", 1995, vol. 364, pp. 129–133.

Taylor, C.P., et al., Epilepsy Research, Potent and Stereospecific Anticonvulsant Activity of 3–Isobutyl Gaba Relates to in vitro Binding at a Novel Site Labeled by Tritiated Gabapentin, 1993, vol. 14, pp. 11–15.

Thurlow, R.J., et al., European Journal of Pharmacology–Molecular Pharmacology Section, "[3H]Gabapentin May Label a System–L–Like Neutral Amino Acid Carrier in Brain", 1993, vol. 247, pp. 341–345.

Suman–Chauhan, N., et al., European Journal of Pharmacology–Molecular Pharmacology Section, "Characterisation of [3H]Gabapentin Binding to a Novel Site in Rat Brain: Homogenate Binding Studies", 1993, vol. 244, pp. 293–301.

Ellis, S.B., et al., Science, "Sequence and Expression of MRNAS Encoding the Alpha1 and Alpha2 Subunit of a DHP–Sensitive Calcium Channel", 1988, vol. 241, pp. 1661–1664.

Dejongh, K.S., The Journal of Biological Chemistry, "Subunits of Purified Calcium Channels", 1990, vol. 265, pp. 14738–14741.

(Continued)

*Primary Examiner*—Michael Pak
(74) *Attorney, Agent, or Firm*—Eric J. Baude; Charles W. Ashbrook; Austin W. Zhang

(57) ABSTRACT

Soluble α₂δ-1 subtype polypeptides.

Methods for cloning, expression and purification of freely soluble α₂δ-1 subtype polypeptides.

5 Claims, No Drawings

OTHER PUBLICATIONS

Jay, S.D., et al., The Journal of Biological Chemistry, "Structural Characterization of the Dihydropyridine–Sensitive Calcium Channel Alpha2–Subunit and th Eassociated Delta Peptides", 1991, vol. 266, pp. 3287–3293.

Wiser, O., et al., FEBS Letters, The Alpha2/Delta Subunit of Voltage Sensitive CA2+ Channels is a Single Transmembrane Extracellular Protein Which is Involved in Regulated Secretion, 1996, vol. 379, pp. 15–20.

Brown, J.P., et al., Rev. Contemp. Pharmacother, "Mechanisms of Action of Gabapentin", 1996, vol. 7, pp. 203–214.

Brown, J.P., et al., Analytical Biochemistry, "Isolation of the [3H]Gabapentin–Binding Protein/Alpha2Delta CA2+ Channel Subunit From Porcine Brain: Development of a Radioligand Binding Assay for Alpha2Delta Subunits Using [3H] Leucine", 1998, vol. 255, pp. 236–243.

PORCINE $\alpha_2\delta$-1 CALCIUM CHANNEL SUBUNIT CDNA AND SOLUBLE SECRETED $\alpha_2\delta$-1 SUBUNIT POLYPEPTIDES

BACKGROUND OF THE INVENTION

Voltage-dependent $Ca^{2}+$ channels (VDCCS) are heteromultimeric complexes present in both neuronal and non-neuronal tissues, including heart and skeletal muscle. VDCCs are minimally composed of three subunits: a pore-forming transmembrane $\alpha_1$ subunit, a hydrophilic intracellular $\beta$ subunit, and a membrane-associated $\alpha_2\delta$-1 subunit; a transmembrane $\gamma$ subunit is also found in skeletal muscle tissue. Multiple subtypes and/or splice variants of the $\alpha_1$, $\beta$, and $\alpha_2\delta$-1 subunits have been found. In heterologous expression studies, the $\alpha_2\delta$-1 subunit has been shown to increase $\alpha_1$ currents both by facilitating the assembly of a $\alpha_1$ subunits at the cell surface and by stimulating the peak $\alpha_1$ current. The modulatory effects of $\alpha_2\delta$-1 are more pronounced if the $\alpha_2$ and $\alpha_2\delta$-1 subunits are co-expressed with the $\beta$ subunit. However, the functions of the $\alpha_2\delta$-1, $\beta$, and $\gamma$ subunits in vivo are not yet completely understood.

Gabapentin ((1-aminomethyl)cyclohexane acetic acid or Neurontin) is a structural analogue of GABA, which is mainly used as an adjunctive therapy for epilepsy. Recent research suggests that gabapentin may also have clinical utility for various indications including anxiety and pain. Although designed as a lipophilic GABA-mimetic, gabapentin does not have a high affinity for either $GABA_A$ or $GABA_B$ receptors, GABA uptake sites, or the GABA-degrading enzyme GABA-transaminase (EC 2.6.1.19).

A novel high affinity binding site for $[^3H]$gabapentin in rat, mouse, and pig brains has been characterized. Recently, the $[^3H]$gabapentin-binding protein was isolated from pig brain and identified as the $\alpha_2\delta$-1 subunit of VDCCs. None of the prototypic anticonvulsant drugs displace $[^3H]$ gabapentin binding from the $\alpha_2\delta$-1 subunit. $[^3H]$ Gabapentin-binding is stereospecifically inhibited by two enantiomers of 3-isobutyl GABA. The rank order of potency of gabapentin, and S- and R-isobutyl GABA, at the $[^3H]$ gabapentin binding site mirrors their anticonvulsant activity in mice. However, electrophysiological studies have yielded conflicting data on the action of gabapentin at VDCCs.

The $\alpha_2\delta$-1 subunit is derived from a single gene, the product of which is extensively post-translationally modified particularly through the cleavage of the signal sequence. The polypeptide is cleaved to form disulfide-bridged $\alpha_2$ and $\delta$ peptides, both of which are heavily glycosylated. Although the $\alpha_2$ and $\delta$ peptides are membrane-associated peptides, it is unclear whether these peptides comprise one or several transmembrane domains. Furthermore, the location, size and structural configuration of these eventual transmembrane domains remains to be determined.

In any event, the fact that $\alpha_2\delta$-1 is a membrane-associated protein, regardless of its precise structural configuration, renders its large scale expression in recombinant systems difficult. Indeed, since the $\alpha_2\delta$-1 protein is targeted to the membrane, it requires detergent solubilisation to purify it. Thus this important drawback imposes considerable restrictions for any potential applications requiring large amounts of recombinant protein.

SUMMARY OF THE INVENTION

In the context of the present invention, the inventors have cloned, isolated and sequenced the porcine cerebral cortical voltage-dependant calcium channel $\alpha_2\delta$-1 subunit cDNA. (hereinafter the porcine $\alpha_2\delta$-1 subunit cDNA).

The invention therefore concerns a purified or isolated nucleic acid encoding a porcine $\alpha_2\delta$-1 subunit cDNA or a sequence complementary thereto.

Oligonucleotide probes or primers specifically hybridizing to a nucleic acid encoding a porcine $\alpha_2\delta$-1 subunit, to fragments thereof or to a sequence complementary thereto are also part of the invention as well as DNA amplification and detection methods using said primers and probes.

The inventors have also found that it was possible to delete a portion of the nucleotide sequence encoding a eukaryotic, preferably a mammalian $\alpha_2\delta$-1 subunit to yield a soluble secreted protein which retains its affinity for $[^3H]$gabapentin and/or other derivatives or compounds such as pregabelin and gabapentoids.

Hence, the invention also concerns nucleotide sequence fragments of an $\alpha_2\delta$-1 subunit cDNA encoding a soluble secreted $\alpha_2\delta$-1 subunit polypeptide. Preferably, these nucleotide sequences encode a soluble secreted $\alpha_2\delta$-1 subunit polypeptide bearing a gabapentin or a $[^3H]$gabapentin binding site. More preferably, the soluble secreted $\alpha_2\delta$-1 subunit nucleic acid is derived from the porcine or human $\alpha_2\delta$-1 subunits.

A further object of the present invention concerns recombinant vectors comprising any of the nucleic acid sequence described herein, and in particular recombinant vectors comprising a nucleic acid sequence encoding a recombinant porcine $\alpha_2\delta$-1 subunit of the invention.

The invention also includes recombinant vectors comprising a nucleic acid sequence encoding a soluble secreted $\alpha_2\delta$-1 subunit polypeptide.

The invention also encompasses host cells and transgenic non-human mammals comprising said nucleic acid sequences or recombinant vectors.

The invention concerns an isolated recombinant porcine $\alpha_2\delta$-1 subunit.

The invention also concerns a porcine $\alpha_2\delta$-1 subunit polypeptide or a peptide fragment thereof as well as antibodies specifically directed against such porcine $\alpha_2\delta$-1 subunit polypeptide or peptide fragment.

Furthermore, the invention concerns a secreted soluble $\alpha_2\delta$-1 subunit polypeptide which is characterized in that it is a soluble secreted polypeptide having affinity for $[^3H]$ gabapentin. Preferably, the soluble secreted polypeptide is derived from the porcine or human $\alpha_2\delta$-1 subunits.

DETAILED DESCRIPTION OF THE INVENTION

The invention concerns an isolated nucleotide sequence of the porcine $\alpha_2\delta$-1 subunit cDNA. The invention also concerns truncated $\alpha_2\delta$-1 subunit cDNA sequences. These truncated sequences encode a soluble secreted polypeptide which retain affinity for $[^3H]$gabapentin. More details on the various embodiments of the invention are provided below.

A) Porcine $\alpha_2\delta$-1 Subunit cDNA

A first object of the present invention is of a purified or isolated nucleic acid encoding a porcine $\alpha_2\delta$-1 subunit, or a sequence complementary thereto.

This cDNA was isolated in several steps. First, a porcine cerebral cortical cDNA library was screened using a fragment of the rabbit skeletal muscle $\alpha_2\delta$-1 clone as the probe. This allowed the isolation of a $\alpha_2\delta$-1 coding region which was homologous to the 3' region of the human neuronal $\alpha_2\delta$-1 sequence but lacked a substantial portion of the 5' coding sequence. The missing sequence was then obtained by 5'-RACE using total RNA prepared from porcine cerebral cortex.

Another object of the invention is a purified or isolated nucleic having at least 90%, preferably 95%, more preferably 98% and most preferably 99% nucleotide identify with the nucleotide sequence of SEQ ID NO:1, or a sequence complementary thereto.

A further object of the present invention is a purified or isolated nucleic acid encoding a polypeptide having at least 80%, preferably 90%, more preferably 95%, and most preferably 98 or 99% amino-acid identity with the porcine polypeptide of the amino-acid sequence of SEQ ID NO:5 or with a peptide fragment thereof, or a sequence complementary thereto.

Polypeptides having amino-acid identity with the $\alpha_2\delta$-1 subunit of the invention encompass polypeptides:

that have primary structures which are related to the $\alpha_2\delta$-1 subunit of any one of the amino-acid sequences of SEQ ID NO:5, due to the high sequence identity between the amino-acid sequences; or that are biologically related to the polypeptides of any one of the amino-acid sequences of SEQ ID NO:5, either because these homologous polypeptides are recognized by antibodies specifically directed against the amino-acid sequence of SEQ ID NO:5 and/or because these homologous polypeptides have the same biological activity as the polypeptides of the amino-acid sequence of SEQ ID NO:5, such as for example the capacity of binding [$^3$H]gabapentin with suitable affinity.

It is important to note that the first 24 amino acids of the amino acid sequence of SEQ ID NO:5 is a signal peptide. This signal peptide can in some embodiments be deleted or replaced by a signal peptide from another species. For example, if one wishes to express this protein in insect cells, the native porcine $\alpha_2\delta$-1 signal peptide can be replaced by a signal peptide of insect origin.

The term "isolated", when used herein, requires that the material be removed from its original environment (e.g. the natural environment if it is naturally occurring). For example, a naturally occurring polynucleotide or a peptide present in a living animal is not isolated, but the same polynucleotide or peptide, separated from some or all of the coexisting materials in the natural system, is isolated. Such polynucleotide can be part of a vector and/or such polynucleotide or peptide can be part of a composition, and still be isolated. This is so because the vector or composition is not part of the original environment of the nucleotide sequence it contains.

The term "purified" does not require absolute purity; rather, it is intended as a relative definition. Purification of starting materials or natural materials to at least one order of magnitude, preferably two or three orders, and more preferably four or five orders of magnitude is expressly contemplated.

Throughout the present specification, the expression "nucleotide sequence" is used to designate indifferently a polynucleotide or a nucleic acid. More precisely, the expression "nucleotide sequence" encompasses the nucleic material and the sequence information and is not restricted to the sequence information (i.e. the succession of letters chosen among the four base letters) that biochemically characterizes a specific DNA or RNA molecule.

As used interchangeably herein, the terms "oligonucleotides", "nucleic acids" and "polynucleotides" include RNA, DNA, or RNA/DNA hybrid sequences of more than one nucleotide in either single chain or duplex form.

Further to its general meaning understood by the one skilled in the art, the term "nucleotide" is also used herein to encompass modified nucleotides which comprise at least one of the following modifications (a) an alternative linking group, (b) an analogous form of purine, (c) an analogous form of pyrimidine, or (d) an analogous sugar. For examples of analogous linking groups, purines, pyrimidines, and sugars, see for example PCT publication N°WO 95/04064.

The polynucleotide sequences of the invention may be prepared by any known method, including synthetic, recombinant, or a combination thereof as well as through any purification methods known in the art.

B) Secreted $\alpha_2\delta$-1 Subunit Polypeptides

The invention also encompasses polynucleotide fragments of a nucleic acid encoding a eukaryotic, preferably a mammal $\alpha_2\delta$-1 subunit. These fragments particularly include but are not restricted to 1) those fragments encoding a soluble secreted polypeptide of this $\alpha_2\delta$-1 subunit which preferably retains its binding affinity for [$^3$H]gabapentin and/or other derivatives or compounds such as pregabalin and gabapentoids and 2) nucleotide fragments useful as nucleic acid primers or probes for amplification or detection purposes. The expression "soluble secreted $\alpha_2\delta$-1 subunit" is intended to designate polypeptide sequences which, when produced by a recombinant host cell, are secreted at least partially into the culture medium rather than remaining associated with the host cell membrane.

1) cDNA Fragments Encoding Soluble Secreted $\alpha_2\delta$-1 Subunit Polypeptides One of the important embodiments of the present invention concerns truncated nucleotide sequences of $\alpha_2\delta$-1 subunit cDNAs which encode soluble secreted $\alpha_2\delta$-1 subunit polypeptides. The inventors have found that it was possible to generate deletion mutants of $\alpha_2\delta$-1 subunit cDNAs which, when expressed, produce a significant amount of soluble secreted proteins, preferably soluble secreted proteins, which retain their [$^3$H]gabapentin binding affinity. These truncated nucleotide sequences of the invention are of significant value to the skilled person as they now allow fast and reliable access to significant concentrations of selected soluble secreted $\alpha_2\delta$-1 subunit polypeptides. To that end, the inventors have determined the minimal and optimal fragment lengths required to express a polypeptide which: 1) binds [$^3$H]gabapentin with sufficient affinity and, 2) is obtained in a soluble secreted form.

The discussion provided below provides detailed comments on possible truncations, giving as an example the porcine $\alpha_2\delta$-1 subunit. However, given the very substantial cross-species homology for $\alpha_2\delta$-1 subunit sequences, the comments below can also be applied to other eukaryotic species, and more particularly other mammalian species such as rat, mouse, rabbit or human. Their $\alpha_2\delta$-1 subunit sequences, which are available in public databases, share a very substantial homology with the porcine $\alpha_2\delta$-1 subunit sequences.

In a first series of experiments, the inventors determined to what extent the coding sequence of the $\alpha_2\delta$-1 subunit could be truncated and still encode a polypeptide which binds [$^3$H]gabapentin.

The inventors found that full-length $\alpha_2\delta$ clones expressed in COS cells or in other cells of a similar nature such as HEK cells were partially cleaved by proteolytic enzymes. However, this proteolytic cleavage does not appear to completely separate the $\alpha_2$ and $\delta$ polypeptides encoded by the native gene. In fact, the inventors found that the deletion of the last 7 residues of the $\delta$ subunit appears to inhibit proteolytic cleavage of $\alpha_2\delta$-1 However, mutants on which a portion of the $\delta$ subunit coding sequence has been deleted encode proteins which are still binding [$^3$H]gabapentin even though no proteolytic cleavage seems to occur. Thus, it appears that:

the $\alpha_2\delta$-1 polypeptide is not proteolytically cleaved into separate $\alpha_2$ and $\delta$ peptides and;

at least some of the $\delta$ polypeptide must be co-expressed with $\alpha_2$ to form the [$^3$H]gabapentin binding pocket.

In order to determine the minimum of fragment of the $\delta$ subunit [$^3$H]gabapentin binding, the inventors constructed mutants with C-terminal deletions of the $\delta$ component. C-terminally truncated mutants extending to residues 966 and 983 of SEQ ID NO:5 both do not bind [$^3$H]gabapentin. However, mutants extending to residues 1018, 1036, 1063 and 1084 of SEQ ID NO:5 exhibit gabapentin binding activity. Thus, the inventors have identified a 35-residue stretch between residues 984 to 1018 of SEQ ID NO:5 which, when delected with the C-terminal residues which follow, results in the loss of specific [$^3$H]gabapentin binding.

Without wishing to be bound by any particular theory, the inventors believe that this region is either directly involved in the formation of the [$^3$H]gabapentin binding pocket or is required for the structural integrity of the subunit. The two pairs of cysteine residues at positions 984/987 and 1012/1014 may contribute to the tertiary structure of the protein by disulfide bridging. Further deletion experiments on residues 984–1018 of the $\alpha_2\delta$-1 subunit can be easily carried out by the skilled person to determine which mutants comprising a nucleotide sequence encoding within that region bind [$^3$H]gabapentin.

In a second series of experiments, the inventors found that nucleotide sequences encoding soluble secreted porcine $\alpha_2\delta$-1 subunit and which retain their binding affinity for [$^3$H]gabapentin could be generated by deleting a portion of the $\alpha_2\delta$-1 subunit cDNA.

In order to determine the optimal deletions on the $\alpha_2\delta$-1 subunit cDNA that yield a soluble secreted protein devoid of membrane anchorage structures, the inventors tested the expression of several porcine $\alpha_2\delta$-1 subunit cDNA deletion mutants. The inventors found that by deleting from the porcine $\alpha_2\delta$-1 subunit cDNA a nucleotide sequence encoding as much as amino-acids 967 to 1091 of the native protein, soluble secreted polypeptides could be obtained. On the other hand, the minimal deletion required to achieve solubility appears to be located around nucleotides encoding amino-acids 1064 to 1091 of the sequence of SEQ ID NO:5. In this regard, the mutant polypeptide expressed using a cDNA deletion mutant from which a sequence encoding amino-acids 1064 to 1091 is removed is found in both soluble and membrane-associated forms, with [$^3$H] gabapentin binding properties similar to that of the wild type protein. Furthermore, a mutant protein expressed using a cDNA deletion mutant from which a nucleotide sequence encoding amino-acids 1085 to 1091 is removed recovers its membrane anchorage properties. Also, mutant proteins expressed using cDNA deletion mutants from which nucleotide sequences encoding either amino-acids 1037 to 1091 or amino-acids 1019 to 1091 of SEQ ID NO:5 are removed are found in soluble form.

The inventors believe that the soluble secreted $\alpha_2\delta$-1 subunit polypeptides which are as close as possible to the native sequence and which are therefore more likely to retain their native folding and hence thir [$^3$H]gabapentin binding properties are those corresponding to the native protein in which amino-acid stretch 985–1091 to 1079–1091 of the amino-acid sequence of SEQ ID NO:5 has been deleted. The skilled scientist can quite easily determine within this 90 amino-acid stretch the optimal $\alpha_2\delta$-1 subunit polypeptides.

The inventions therefore particularly concerns a nucleotide sequence encoding a polypeptide having at least 80% identity with the polypeptide comprising from amino-acid 1 to between amino-acids 985 and 1054, preferably between amino-acids 985 and 1059, and most preferably between amino-acids 1019 and 1064 of SEQ ID NO:5 or SEQ ID NO:14. Preferred nucleotide sequences include those of SEQ ID NO:2, SEQ ID NO:3, SEQ ID NO:4, SEQ ID NO:19, SEQ ID NO:20 and SEQ ID NO:21.

2) Fragments of the Porcine $\alpha_2\delta$-1 Subunit cDNA Useful as Primers and Probes The present invention also concerns a purified or isolated polynucleotide comprising at least 10 consecutive nucleotides of a nucleic acid encoding the porcine $\alpha_2\delta$-1 subunit described herein, preferably at least 10 consecutive nucleotides of the nucleotide sequence of SEQ ID NO:1, or a sequence complementary thereto.

These nucleic acids consist of a contiguous span which ranges in length from 10, 12, 15, 18 or 20 to 25, 35, 40, 50, 70, 80, 100, 250, 500 or 1000 nucleotides, or be specified as being 10, 12, 15, 18, 20, 25, 35, 40, 50, 100, 200, 250, 500 or 1000 nucleotides in length.

These nucleic acids are useful as probes in order to detect the presence of at least a copy of a nucleotide sequence encoding the porcine $\alpha_2\delta$-1 subunit, more particularly the presence of at least a copy of a nucleotide sequence of SEQ ID NO:1 or a sequence complementary thereto or a fragment or a variant thereof in a sample. The sequence of such nucleic acids could be slightly modified (for example by substituting one nucleotide for another) without substantially affecting the ability of such modified sequence to hybridize with the targeted sequence of interest.

The nucleic acid probes of the invention may also be used for the analysis of the expression levels and patterns of the porcine $\alpha_2\delta$-1 subunit, such as described in the PCT Application N°WO 97/05 277, the entire contents of which is herein incorporated by reference.

The invention also concerns purified or isolated nucleic acid sequences that hybridize, under stringent hybridization conditions, with a nucleic acid encoding a porcine $\alpha_2\delta$-1 subunit or a sequence complementary thereto.

As an illustrative embodiment, stringent hybridization conditions can be defined as follows:

The hybridization step is conducted at 65° C. in the presence of 6×SSC buffer, 5×Denhardt's solution, 0.5% SDS and 100 µg/ml of salmon sperm DNA.

The hybridization step is followed by four washing steps:

two washings during 5 minutes, preferably at 65° C. in a 2×SSC and 0.1% SDS buffer;

one washing during 30 minutes, preferably at 65° C. in a 2×SSC and 0.1% SDS buffer;

one washing during 10 minutes, preferably at 35° C. in a 0.1×SSC and 0.1% SDS buffer, It being understood that the hybridization conditions defined above are suitable for nucleic acids of approximately twenty nucleotides in length and that these conditions may be also adapted for shorter or longer nucleic acids, according to techniques well known in the art, for example those described by Sambrook et al. (1989).

The appropriate length for probes under a particular set of assay conditions may be empirically determined by the one skilled in the art. The probes can be prepared by any suitable method, including, for example, cloning and restriction of appropriate sequences and direct chemical synthesis by a method such as the phosphodiester method of Narang et al.(1979), the phosphodiester method of Brown et al., (1979), the diethylphosphoramidite method of Beaucage et al. (1981) and the solid support method described in the application N°EP-0 707 792. The disclosures of all these documents are incorporated herein by reference.

Any of the nucleic acids of the present invention can be labelled, if desired, by incorporating a label detectable by spectroscopic, photochemical, biochemical, immunochemical, or chemical means.

For example, useful labels include radio-active substances ($^{32}$P, $^{35}$S, 3H, 125I), fluorescent dyes (5-bromodesoxyuridin, fluorecein, acetylaminofluoren, digoxygenin) or biotin. Examples of non-radioactive labelling of nucleic acid fragments are described in French Patent N°FR-78 10975 or by Urdea et al. (1988) or Sanchez-Pescador et al. (1988).

Advantageously, the probes according to the present invention may have structures and characteristics such that they allow signal amplification, such structural characteristics being, for example, those of branched DNA probes as described by Urdea et al. (1991).

Any of the nucleic acid probes of the invention can be conveniently immobilized on a solid support. Solid supports are known those skilled in the art and include the walls of wells of a reaction tray, test tubes, polystyrene beads, magnetic beads, nitro-cellulose strips, membranes, microparticules such as latex particles, sheep red blood cells, duracytes and others.

The nucleic acids of the invention and particularly the nucleotide probes described above can thus be attached to or immobilized on a solid support individually or in groups of at least 2, 5, 8, 10, 12, 15, 20 or 25 distinct nucleic acids of the invention to a single solid support.

In a specific embodiment of a support on which nucleic acid probes of the invention are immobilized, such a support may also contain other immobilized probes, preferably probes that hybridize specifically with a nucleic acid encoding the porcine $\alpha_2\delta$-1 subunit, or a variant thereof, or a sequence complementary thereto.

C) Amplification of the Porcine $\alpha_2\delta$-1 Subunit cDNA or of Soluble Secreted $\alpha_2\delta$-1 Subunit Nucleotide Sequences Another object of the invention consists of a method for the amplification of a nucleic acid encoding a porcine $\alpha_2\delta$-1 subunit or a soluble secreted $\alpha_2\delta$-1 subunit polypeptide, preferably a polypeptide bearing a [$^3$H]gabapentin binding site, said method comprising the steps of:

(a) contacting a test sample suspected of containing the target $\alpha_2\delta$-1 subunit nucleic acid, a fragment or a variant thereof, or a sequence complementary thereto, with an amplification reaction reagent comprising a pair of amplification primers which can hybridize under stringent conditions, the $\alpha_2\delta$-1 subunit nucleic acid region to be amplified, and (b) optionally, detecting the amplification products.

In a first preferred embodiment of the above method, the nucleic acid encodes a porine $\alpha_2\delta$-1 subunit of SEQ ID NO:5, or a secreted soluble $\alpha_2\delta$-1 subunit polypeptide of SEQ ID NO:6, SEQ ID NO:7, SEQ ID NO:8, SEQ ID NO:15, SEQ ID NO:16 and SEQ ID NO:17, In a second preferred embodiment of the above method, a first primer is the nucleotide sequence of SEQ ID NO:9 and a second primer is complementary to a portion of the 3' untranslated region of SEQ ID NO:5, such as the primer having the sequence of SEQ ID NO:22.

In a third preferred embodiment of the above amplification method, the amplification product is detected by hybridization with a labelled probe having a sequence which is complementary to the amplified region.

The invention also concerns a kit for the amplification of a nucleic acid encoding a porcine $\alpha_2\delta$-1 subunit, a fragment or a variant thereof, or a complementary sequence thereto in a test sample, wherein said kit comprises:

(a) a pair of oligonucleotide primers which can hybridize, under stringent conditions to $\alpha_2\delta$-1 subunit nucleic acid to be amplified;

(b) optionally, the reagents necessary for performing the amplification reaction.

In a first preferred embodiment of the kit described above, the nucleic acid encodes the porcine $\alpha_2\delta$-1 subunit of SEQ ID NO:5.

In a second preferred embodiment of the above amplification kit, the amplification product is detected by hybridization with a labelled probe having a sequence which is complementary to the amplified region.

In a third embedment of the above amplification kit, the amplification primers are respectively the nucleic sequences of SEQ ID NO:9 and SEQ ID NO:10.

D) Recombinant Vectors and Hosts Cells for the Expression of a Porcine $\alpha_2\delta$-1 Subunit or of a Secreted Soluble $\alpha_2\delta$-1 Subunit Polypeptide 1) Recombinant Vectors The present invention also encompasses a family of recombinant vectors comprising any one of the nucleic acids described herein. Firstly, the invention deals with a recombinant vector comprising a nucleic acid selected from the group consisting of:

(a) a purified or isolated nucleic acid encoding a porcine $\alpha_2\delta$-1 subunit, and more preferably a polypeptide having at least 80% amino acid identity with the polypeptide of SEQ ID NO:5, or a sequence complementary thereto;

(b) a purified or isolated nucleic acid having at least 90% nucleotide identity with a polynucleotide selected from the group consisting of the nucleotide sequences of SEQ ID NO:2, SEQ ID NO:3, SEQ ID NO:4, SEQ ID NO:19, SEQ ID NO:20 and SEQ ID NO:21 or a sequence complementary thereto;

(c) a purified or isolated polynucleotide comprising at least 10 consecutive nucleotides of a nucleic acid described in (a) or a sequence complementary thereto.

In a first preferred embodiment a recombinant vector of the invention is used to amplify the inserted polynucleotide derived from the nucleic acid encoding a porcine $\alpha_2\delta$-1 subunit of the invention in a suitable host cell, this polynucleotide being amplified every time the recombinant vector replicates.

Recombinant expression vectors comprising a nucleic acid encoding $\alpha_2\delta$-1 subunit polypeptides that are described in the present specification are also part of the invention.

These include, but are not restricted to, nucleic acids encoding from amino acid 1 to between amino-acids 985 to 1054, preferably between amino-acids 984 and 1059, more preferably between amino-acids 1019 to 1064, SEQ ID NO:5 and SEQ ID NO:14.

Another preferred embodiment of the recombinant vectors according to the invention consist of expression vectors comprising a nucleic acid encoding an $\alpha_2\delta$-1 subunit polypeptide of the invention, and more preferably a nucleic acid encoding a polypeptide selected from the group consisting of the amino acid sequences of SEQ ID NO:5, SEQ ID NO:6, SEQ ID NO:7, SEQ ID NO:8, SEQ ID NO:15, SEQ ID NO:16 and SEQ ID NO:17.

Within certain embodiments, expression vectors can be employed to express the porcine $\alpha_2\delta$-1 subunit of the invention or secreted soluble $\alpha_2\delta$-1 subunit polypeptides which can then be purified and for example, be used as a immunogen in order to raise specific antibodies directed against said porcine $\alpha_2\delta$-1 subunit protein or secreted soluble $\alpha_2\delta$-1 subunit polypeptides.

Preferred eukaryotic vectors of the invention are listed hereafter as illustrative but not limitative examples: pcDNA3, pFLAG, pCMV-Script, pIND, pMC1NEO, pHIL, pGAPZA, pMT/V5-His-TOPO, pMT/V5-His, pAc5.1/V5-HisA, pDS47/V5-His, pcDNA4, pcDNA6, pEF1, pEF4, pEF6, pUB6, pZeoSV2, pRc/CMv2, pcDM8, pCR3.1, pDisplay, pSecTag2, pVP22, pEMZ, pCMV/Zeo, pSinRep5, pCEP, pREP, pHook-1

Preferred bacteriophage recombinant vectors of the invention are P1 bacteriophage vectors such as described by Sternberg N. L. (1992;1994).

A suitable vector for the expression of a porcine $\alpha_2\delta$-1 subunit polypeptide of the invention or a soluble secreted $\alpha_2\delta$-1 subunit polypeptide is a baculovirus vector that can be propagated in insect cells and in insect cell-lines. Specific suitable host vectors includes, but are not restricted to pFastBac-1, pIZ/V5-His, pBacMan-1, pBlueBac4.5, pBlueBacHis2, pMelBacA, pVL1392, pVL1393

The recombinant expression vectors from the invention may also be derived from an adenovirus such as those described by Feldman and Steig. (1996) or Ohno et al. (1994). Another preferred recombinant adenovirus according to this specific embodiment of the present invention is the human adenovirus type two or five (Ad 2 or Ad 5) or an adenovirus of animal origin (French Patent Application n°FR 93 05 954).

a) Regulatory Expression Sequences

Expression requires that appropriate signals are provided in the vectors, said signals including various regulatory elements such as enhancers/promoters from both viral and mammalian sources that drive expression of the genes of interest in host cells. The regulatory sequences of the expression vectors of the invention are operably linked to the nucleic acid encoding the porcine $\alpha_2\delta$-1 subunit protein of interest or a soluble secreted $\alpha_2\delta$-1 subunit polypeptide.

As used herein, the term "operably linked" refers to a linkage of polynucleotide elements in a functional relationship. For instance, a promoter or an enhancer is operably linked to a coding sequence if it affects the transcription of the coding sequence.

More precisely, two DNA molecules (such as a polynucleotide containing a promoter region and a polynucleotide encoding a desired polypeptide or polynucleotide) are said to be "operably linked" if the nature of the linkage between the two polynucleotides does not: (1) result in the introduction of a frame-shift mutation or (2) interfere with the ability of the polynucleotide containing the promoter to direct the transcription of the coding polynucleotide.

Generally, recombinant expression vectors include origins of replication, selectable markers permitting transformation of the host cell, and a promoter derived from a highly expressed gene to direct transcription of a downstream structural sequence. The heterologous structural sequence is assembled in an appropriate frame with the translation, initiation and termination sequences, and preferably a leader sequence capable of directing sequences of the translated protein into the periplasmic space or the extra-cellular medium. In a specific embodiment wherein the vector is adapted for transfecting and expressing desired sequences in eukaryotic host cells, preferred vectors comprise an origin of replication from the desired host, a suitable promoter and an enhancer, and also any necessary ribosome binding sites, polyadenylation site, transcriptional termination sequences, and optionally 5'-flanking non-transcribed sequences.

DNA sequences derived from the SV 40 viral genome, for example SV 40 origin early promoter, enhancer, and polyadenylation sites may be used to provide the required non-transcribed genetic elements.

b) Promoter Sequences

Suitable promoter regions used in the expression vectors according to the invention are chosen taking into account the host cell in which the heterologous nucleic acids have to be expressed.

A suitable promoter may be heterologous with respect to the nucleic acid for which it controls the expression, or alternatively can be endogenous to the native polynucleotide containing the coding sequence to be expressed.

Additionally, the promoter is generally heterologous with respect to the recombinant vector sequences within which the construct promoter/coding sequence has been inserted.

c) Recombinant Host Cells

Host cells that have been transformed or transfected with one of the nucleic acids described herein, or with one of the recombinant vector, particularly recombinant expression vector, described herein are also part of the present invention.

Are included host cells that are transformed (prokaryotic cells) or are transfected (eukaryotic cells) with a recombinant vector such as one of those described above. Preferred host cells used as recipients for the expression vectors of the invention are the following:

(a) prokaryotic host cells: *Escherichia coli*, strains. (i.e. DH10 Bac strain) *Bacillus subtilis, Salmonella typhimurium* and strains from species such as *Pseudomonas, Streptomyces* and *Staphylococcus;*

(b) eukaryotic host cells: HeLa cells (ATCC N°CCL2; N°CCL2.1; N°CCL2.2), Cv 1 cells (ATCC N°CCL70), COS cells (ATCC N°CRL 1650; N°CRL 1651), Sf-9 cells (ATCC N°CRL 1711), C127 cells (ATCC N°CRL-1804), 3T3 cells (ATCC N°CRL-6361), CHO cells (ATCC N°CCL-61), human kidney 293 cells (ATCC N° 45504; N°CRL-1573), BHK (ECACC N°84100 501; N°84111301), sf9, sf21 and hi-5 cells.

E) Production of Recombinant $\alpha_2\delta$-1 Subunit Polypeptides

The present invention also concerns a method for producing one of the amino acid sequences described herein and especially a polypeptide selected from the group consisting the amino acid sequences of SEQ ID NO:5, SEQ ID NO:6, SEQ ID NO:7, SEQ ID NO:8, SEQ ID NO:15, SEQ ID NO:16 or SEQ ID NO:17 wherein said method comprises the steps of:

(a) inserting the nucleic acid encoding the desired amino acid sequence in an appropriate vector, (b) culturing, in an appropriate culture medium, a host cell previously transformed or transfected with the recombinant vector or of step (a);

(c) harvesting the culture medium thus obtained or lyse the host cell, for example by sonication or osmotic shock;

(d) separating or purifying, from said culture medium, or from the pellet of the resultant host cell lysate, the thus produced recombinant polypeptide of interest.

In some instances, it may be required to tag the $\alpha_2\delta$-1 subunit polypeptide prior to purification. The tag is then in most instances encoded into the nucleotide sequence that is needed to express the polypeptide. Examples of such tags include, but are not limited to sequences encoding C-myc, FLAG, a sequence of histidine residues, heamaglutin A, V5, Xpress or GST. Most of these tags can be incorporated directly into the sequence, for instance through PCR amplification by incorporating the appropriate coding sequence in one of the PCR amplification primers. However, the tag can also be introduced by other means such as covalent binding of the appropriate nucleic acid sequence encoding the tag moiety with the 3' or 5' end of the nucleic acid sequence encoding the polypeptide sequence. This is the case for GST.

Purification of the recombinant $\alpha_2\delta$-1 subunit polypeptides according to the present invention is then carried out by passage onto a nickel or copper affinity chromatography column, such as a Ni NTA column.

In another embodiment of the above method, the polypeptide thus produced is further characterized, for example by binding onto an immuno-affinity chromatography column on which polyclonal or monoclonal antibodies directed to the $\alpha_2\delta$-1 subunit polypeptide, of interest have been previously immobilised.

F) Purified Recombinant $\alpha_2\delta$-1 Polypeptides

Another object of the present invention consists of a purified or isolated recombinant polypeptide comprising the amino acid sequence of the porcine $\alpha_2\delta$-1 subunit or the amino acid sequence of a secreted soluble $\alpha_2\delta$-1 subunit polypeptide.

Preferred isolated recombinant polypeptides of the invention include those having at least 80%, preferably 90%, more preferably 95, and most preferably 98 or 99%, amino-acid identity with polypeptides comprising from amino acid 1 to between amino-acids 985 and 1054, preferably between amino-acids 985 and 1059, and more preferably between amino-acids 1019 and 1064 of SEQ ID NO:5 or SEQ ID NO:14.

In a further preferred embodiment, the polypeptide comprises an amino acid sequence having at least 80%, preferably 90%, more preferably 95%, and most preferably 98% or 99% amino acid identity with the amino acid sequence of SEQ ID NO:5, SEQ ID NO:6, SEQ ID NO:7, SEQ ID NO:8, SEQ ID NO:15, SEQ ID NO:16 and SEQ ID NO:17.

G) Modified $\alpha_2\delta$-1 Subunit Polypeptides

The invention also relates to a porcine $\alpha_2\delta$-1 subunit, or a secreted soluble $\alpha_2\delta$-1 subunit polypeptide comprising amino acid changes ranging from 1, 2, 3, 4, 5, 10, 20, 25, 30, 35, 40 substitutions, additions or deletions of one amino acid as regards to polypeptides of anyone of the amino acid sequences of the present invention. Preferred sequences are those of SEQ ID NO:5, SEQ ID NO:6, SEQ ID NO:7, SEQ ID NO:8, SEQ ID NO:15, SEQ ID NO:16 and SEQ ID NO:17.

In the case of an amino acid substitution in the amino acid sequence of a polypeptide according to the invention, one or several consecutive or non-consecutive amino acids are replaced by "equivalent" amino acids. The expression "equivalent" amino acid is used herein to designate any amino acid that may be substituted for one of the amino-acids belonging to the native protein structure without decreasing the binding properties of the corresponding peptides to the antibodies raised against the polypeptides of the invention. In other words, the "equivalent" amino-acids are those which allow the generation or the synthesis of a polypeptide with a modified sequence when compared to the amino acid sequence of the $\alpha_2\delta$-1 subunit polypeptides of interest, said modified polypeptide being able to bind to the antibodies raised against the $\alpha_2\delta$-1 subunit polypeptide of interest and/or to induce antibodies recognizing the parent polypeptide.

Alternatively, amino acid changes encompassed are those which will not abolish the biological activity of the resulting modified polypeptide. These equivalent amino-acids may be determined either by their structural homology with the initial amino-acids to be replaced, by the similarity of their net charge or of their hydrophobicity, and optionally by the results of the cross-immunogenicity between the parent peptides and their modified counterparts.

The peptides containing one or several "equivalent" amino-acids must retain their specificity and affinity properties to the biological targets of the parent protein, as it can be assessed by a ligand binding assay or an ELISA assay.

Examples of amino-acids belonging to specific classes include Acidic (Asp, Glu), Basic (Lys, Arg, His), Non-polar (Ala, Val, Leu, Ile, Pro, Met, Phe, Trp) or uncharged Polar (Gly, Seu, Thr, Iys, Tyr, Asn, Gln) amino-acids.

Preferably, a substitution of an amino acid in a porcine $\alpha_2\delta$-1 subunit polypeptide of the invention, or in a peptide fragment thereof, consists in the replacement of an amino acid of a particular class for another amino acid belonging to the same class.

By an equivalent amino acid according to the present invention is also contemplated the replacement of a residue in the L-form by a residue in the D form or the replacement of a Glutamic acid (E) residue by a Pyro-glutamic acid compound. The synthesis of peptides containing at least one residue in the D-form is, for example, described by Koch (1977).

A specific embodiment of a modified peptide of interest according to the present invention, includes, but is not limited to, a peptide molecule, which is resistant to proteolysis. This is a peptide in which the —CONH— peptide bond is modified and replaced by a ($CH_2NH$) reduced bond, a (NHCO) retro inverso bond, a ($CH_2$—O) methylene-oxy bond, a ($CH_2S$) thiomethylene bond, a ($CH_2CH_2$) carba bond, a (CO—$CH_2$) cetomethylene bond, a (CHOH—$CH_2$) hydroxyethylene bond), a (N—N) bound, a E-alcene bond or also a —CH=CH-bond. The invention also encompasses a porcine $\alpha_2\delta$-1 subunit polypeptide or a secreted soluble $\alpha_2\delta$-1 subunit polypeptide in which at least one peptide bond has been modified as described above.

The polypeptides according to the invention may also be prepared by the conventional methods of chemical synthesis, either in a homogenous solution or in solid phase. As an illustrative embodiment of such chemical polypeptide synthesis techniques, it may be cited the homogenous solution technique described by Houbenweyl (1974).

The porcine $\alpha_2\delta$-1 subunit polypeptide of interest, or a fragment thereof may thus be prepared by chemical synthesis in liquid or solid phase by successive couplings of the different amino acid residues to be incorporated (from the N-terminal end to the C-terminal end in liquid phase, or from the C-terminal end to the N-terminal end in solid phase) wherein the N-terminal ends and the reactive side chains are previously blocked by conventional groups.

For solid phase synthesis, the technique described by Merrifield (1965a; 1965b) may be used in particular.

H) Antibody Production

The porcine $\alpha_2\delta$-1 subunit polypeptides of the invention and their peptide fragments of interest can be used for the preparation of antibodies.

Polyclonal antibodies may be prepared by immunization of a mammal, especially a mouse, a rabbit or a sheep, with a polypeptide according to the invention that is combined with an adjuvant of immunity, and then by purifying the specific antibodies contained in the serum of the immunized animal on an affinity chromatography column on which has previously been immobilized the polypeptide that has been used as the antigen.

Monoclonal antibodies may be prepared from hybridomas according to the technique described by Kohler and Milstein (1975).

The present invention also deals with antibodies produced by the trioma technique and by the human B-cell hybridoma technique, such as described by Kozbor et al. (1983).

Antibodies of the invention also include chimeric single chain Fv antibody fragments (U.S. Pat. No. 4,946,778, Martineau et al., (1998), antibody fragments obtained through phage display libraries Ridder et al. (1995) and humanized antibodies (Leger et al., (1997)).

EXAMPLES

Example 1
Cloning of the Porcine Cerebral Cortical $\alpha_2\delta$-1 cDNA

An oligo dT-primed λgt10 porcine cerebral cortical cDNA library was screened by ECL (Amersham) using a 2,381-bp HindIII fragment (coding sequence 268–2649) of the rabbit skeletal muscle $\alpha_2\delta$-1 clone (pcDNA3-Rab-$\alpha_2\delta$-(+); supplied by Dr. Offord, Parke-Davis Pharmaceutical Research, Ann Arbor, Mich.) as the probe.

A positive insert was identified and subcloned into pBluescript-SK-(+) to generate pB-PC-$\alpha_2\delta$-1.1. The clone was sequenced on both strands, except for a 711-bp stretch at one end of the clone, which had a high degree of homology to mitochondrial C oxidase.

The $\alpha_2\delta$-1 coding region was homologous to the 3' region of the human neuronal$\alpha_2\delta$ sequence but lacked 926 bp of 5' coding sequence. The missing sequence was obtained by 5'-RACE using total RNA prepared from porcine cerebral cortex. RACE was performed across a BglI site unique in known $\alpha_2\delta$-1 sequences (rabbit (accession no. M21948), rat (accession number M86621), human (accession no. M76559)

Primers were designed to amplify the missing 5' portion of the $\alpha_2\delta$ cDNA by 5' Rapid Amplification of cDNA Ends (5' RACE). A series of primers were synthesized based on the $\alpha_2\delta$ cDNA antisense sequence derived from the $\alpha_2\delta$ coding region obtained above, all are downstream (3') of a unique BglI restriction site. Total RNA was prepamed from porcine cortical membranes and single slrand cDNA synthesized using SuperScipt II reverse transcriptase and the primer furthest from the BglI site (JB039; 5'-TTCTCTAATTCTGCATCAAGG-3', SEQ ID NO:24). The cDNA was then purified and tailed with dCTP's using terminal deoxynucleotidyl transferase. Aliquots of this tailing reaction were then PCR amplified tough 35 cycles using Taq DNA polymerase and the primer pair JB041 (5'-TTTGGATGTAATAAAACATAG-3', SEQ ID NO:25) and the universal amplificaton primer (5'-CUACUACUACUAGGCCACGCGTCGACTAGTAC-3', SEQ ID NO:26). Several PCR products were generated and Qiaex gel-purified. All products were positive by Southern blot hybridization using a 1,264 bp probe (5' $\alpha_2\delta$ coding sequence) derived from a Hind III/BglI restriction digest of pcDNA3-Rab-$\alpha_2\delta$-(+). Each PCR product was sub-cloned into pBluescript. The 5' and 3' ends of each insert were sequenced confirming that all clones contain $\alpha_2\delta$ sequence as predicted from the Southern blot experiment. The longest of the inserts contained sequence that extended 24 bp into the non-coding sequence of the $\alpha_2\delta$ cDNA.

The sequence derived from the 5' RACE product was used to design a primer (JB042, 5'-GGGGATTGATCTTCGATCGCG-3'; SEQ ID NO:9) specific for the 5'-untranslated end of the cDNA. PCR was then performed with Pfu DNA polymerase using JB042 and a primer downstream of the BglI site (5'-GCAGATTTGGTTTTAGAAGGG-3', SEQ ID NO:22) The PCR product was ligated to EcoRI linkers (5'-GGAATTCC-3') and then digested with EcoRI and BglI. The 1,564-bp fragment (5' portion of the $\alpha_2\delta$ cDNA) was gel-purified.

Similarly, a 2,303-bp fragment (3' portion of the $\alpha_2\delta$ cDNA) was isolated after digestion of pB-PC-$\alpha_2\delta$-1.1 with BglI and EcoRI. The two fragments of $\alpha_2\delta$-1 cDNA were then ligated to EcoRI-digested pcDNA3 in a three-way ligation. A clone was picked with the full-length $\alpha_2\delta$-1 sequence in the positive orientation with respect to the cytomegalovirus promoter (pcDNA3-PC-$\alpha_2\delta$-(+)). The PCRderived 5' $\alpha_2\delta$-1 sequence in this plasmid was sequenced on both strands.

Example 2
Generation and Purification of Anti-$\alpha_2$ and Anti-$\delta$ Polyclonal Antibodies The $\alpha_2\delta$-1 subunit was purified from porcine brains as described by Gee et al. up to, and including, the Sephacryl S400 step. The sample of partially purified $\alpha_2\delta$-1 subunits was then further purified on a 1-ml $CuSO_4$ charged iminodiacetic acid-Sepharose column. Prior to each use, the column was recharged with $CuSO_4$ following a modified version of the protocol described by Brown et al.

Briefly, the column was stripped of metal ions with 3 ml of 0.5 M EDTA/NaOH, pH 8.0 (at 21° C.), washed with 20 ml of $H_2O$, and then charged with 20 ml of 0.3 M CuSO, before a second wash with 20 ml of $H_2O$ and equilibration in buffer A (750 mM NaCl, 0.08% Tween 20, 10 mM HEPES/KOH, pH 7.4 (at 21° C.)).

The partially purified $\alpha_2\delta$-1 subunits obtained from the S400 chromatography was applied to this column at 0.5 ml/min. Breakthrough material was concentrated to ≈100 microlitter by ultrafiltration (10,000 $M_T$ cut-off membrane) before separation by SDS-polyacrylamide gel electrophoresis on an 8% preparative gel. The 145-kDa band was excised, and the peptide recovered from the gel by electroelution. Rabbits were immunized by Serotec (Oxford, UK).

Anti-$\delta$ antibodies were raised by immunizing rabbits with a keyhole lympet hemocyanin-conjugated peptide, VEMEDDDFTASLSKQSC (SEQ ID NO:11), corresponding to the start sequence of the $\delta$ polypeptide (residues 922–938, relative to the first residue of the mature $\alpha_2$ polypeptide). Peptide synthesis and immunization protocols were performed by Genosys Biotechnologies Inc. (The Woodlands, Tex.).

Purified pig brain $\alpha_2\delta$-1 (125 microgramm) was electrophoresed under reducing conditions on a single wide track 4–20% gradient SDS-polyacrylamide gel. After transfer onto nitrocellulose membrane, two thin horizontal strips corresponding to the $\alpha_2$ and $\delta$ polypeptides were excised with a razor blade. The strips were incubated with blocking buffer (2% milk powder, 150 mM NaCl, 0.1% Tween 20,50 mM Tris-Cl, pH 7.5) for 30 min. Immune serum (1 ml) was diluted 5-fold in blocking buffer and incubated with the appropriate strip for 2 h at 4° C. Strips were then washed three times (15 min each) with blocking buffer and eluted with 2 ml of 50 mM glycine/HCl, pH 2.3. The solution was neutralized with 0.4 ml of 1 M HEPES, pH 8.0. Aliquots of the affinity-purified antibodies were stored frozen at −70° C.

Example 3
Construction of C-terminally Deleted Mutant

For mutants C (▲275–1091 (i.e. residues 275 to 1091 deleted)), D (▲470–1091), E (▲621–1091), F (▲804–1091), G (▲946–1091), H (▲967–1091), I (▲984–1091), J (▲1019–1091, SEQ ID NO:6), K (▲1037–1091, SEQ ID NO:7), L (▲1064–1091, SEQ ID NO:8), M (▲1085–1091), and PCR-WT (3'-untranslated region deleted) amplifications were performed with an anchored 5' primer (JB055, 5'-TGGCTTATCGAAATTAATACG-3', SEQ ID NO:12), which anneals at position 849–869 in pcDNA3-PC-$\alpha_2\delta$-(+).

For mutants A (▲135–1091) and B (▲253–1091), the anchored 5' primer was 5'-AACTCCGGGGATTGATCTTCG-3' (JB 115, SEQ ID NO:13), which anneals at position 971–991. The 3' primer was designed to anneal internally to the $\alpha_2\delta$ coding sequence to generate the specified C-terminally truncated $\alpha_2\delta$ mutant.

All 3' primers had the following tail structure: a double stop codon followed by an EcoRI site (5'-

CAGAATTCCTCATCA-N$_{(18-21)}$-3'), where N is the in-frame site-specific sequence complementary to the α$_2$δ cDNA. Pfu DNA polymerase was used in the PCR reactions a preferred sequence of which is SEQ ID N° 23 (5'-CAGAATTCCTCATCAAGAAACACCACCACAGTCGGT-3') for cloning mutant L, and the products amplified with JB055 were blunt-end cloned into pBluescript-SK(+). The insert was then subcloned into the EcoRI site of pcDNA3. Products generated with JB 115 were cloned directly into the EcoRV site of pcDNA3.

Clones were sequenced to confirm primer regions and a positive orientation with respect to the cytomegalovirus promoter.

Example 4

Construction of a 5-Only Mutant

The α$_2$ sequence (residues 1–921) was deleted utilizing the two-round PCR method employing Pfu DNA polymerase. The product was blunt-end cloned into pBluescriptSK-(+) and then directionally subcloned into pcDNA3 as described above.

Example 5

Transient Expression in COS-7 Cell, Extraction of COS-7 Membranes and Recovery of the Soluble Fractions All media contained 50 units/ml penicillin and 50 microgramm per ml streptomycin. COS-7 cells were maintained in Dulbecco's modified Eagle's medium+glutamax, 10% fetal bovine serum (gamma irradiated) in a 37° C./5% CO$_2$ incubator and passaged by trypsinization. For transient expression experiments, 150-mm culture dishes were seeded with 3.9×10$^6$ cells and incubated for 16 h. Cells were then washed twice with 30 ml of optiMEM-1 and transfected (t=0 h) with 30 microgramm of plasmid DNA by lipofectamine-mediated transfection in 21 ml of optiMEM-1. At t=6 h, a further 21 ml of optiMEM-1 was added. At t=24 h, the medium was replaced with 42 ml of optiMEM-1. At t=48 h, the cells were washed twice with 30 ml of phosphate-buffered saline and then harvested in 3 ml of buffer A (1 nM EDTA, 1 mM EGTA, 20% glycerol, 10 mm HEPES, pH 7.4, at 4° C.) plus 0.1 mM phenymethylsulfonyl fluoride using a cell scraper.

All subsequent operations were performed at 4° C. The cells were rotated on a Spiramix (Denley Instruments) for 30 min, centrifuged at 20,000×g for 5 min, resuspended in 1 ml of buffer A, recentrifuged at 20,000×g for 5 min, and finally resuspended in 400 microliter of buffer A. Membrane preparations were stored at −70° C. until required.

Spent tissue culture medium recovered at t=24 and 48 h was ultracentrifuged at 100,000×g for 1 h and then concentrated by ultrafiltration (10,000 M, cut-off) to approximately 1 ml. The concentrated sample was then extensively dialyzed against buffer A and stored at −70° C. until required.

Samples of membranes (3 microgramms in 48 microliter) were agitated for 2 h on a Spiramix at 4° C. in a total volume of 60 microliters with a final concentration of either 1 M NaCl or 10% ethylene glycol. Samples were ultracentrifuged at 100,000×g for 2 h, and 20 microliter of supernatant was removed for SDS-polyacrylamide gel electrophoresis. The pellet was washed again for 10 min at 4° C. in 1 ml of the same buffer before ultracentrifugation at 100,000×g for 30 min. The supernatant was discarded, and the pellet was resuspended in 120 microgramms of SDS-polyacrylamide gel electrophoresis loading buffer and boiled for 20 min; 40 microgramms was loaded onto the gel.

Example 6

Miscellaneous Methods

Protein concentrations were determined by the method of Bradford using bovine serum albumin as a standard. [$^3$H] Gabapentin binding assays were performed as described previously. For saturation analysis, incubations were performed in duplicate. All other incubations were performed in triplicate. SDS-polyacrylamide gel electrophoresis and Western blotting were performed using the Novex gel and buffer system (Novex Europe, Frankfurt, Germany). Molecular weights were determined by reference to Kaleidoscope markers (Bio-Rad). Detection was performed using the ECL system (Amersham).

References

Perez-Reyes, E., and Schneider, T. (1994) *Drug Dev. Res.* 33, 295–318

Catterall, W. A. (1995) *Annu. Rev. Biochem.* 64, 493–531

Birnbaumer, L., Campbell, K. P., Catterall, W. A., Harpold, M. M., Hofmann, F., Home, W. A., Mori, Y., Schwartz, A., Snutch, T. P., Tanabe, T., and Tsien, R. W. (1994) Neuron 13, 505–506

Brust, P. F., Simerson, S., McCue, A. F., Deal, C. R., Schoonmaker, S., Williams, M. E., Velicelebi, G., Johnson, E. C., Harpold, M. M., and Ellis, S. B. (1993) *Neuropharmacology* 32, 1089–1102

Itagaki, K., Koch, W. J., Bodi, L, Klockner, U., Slish, D. F., and Schwartz, A. (1992) *FEBS Lett.* 297, 221–225

Mikami, A, Imoto, F$_{13}$ Tanabe, T., Niidome, T., Mori, Y., Takeshima, H., Narumiya, S., and Numa, S. (1989) *Nature* 340, 230–233

Mori, Y., Friedrich, T., Kim, M. S., Mikami, A., Nakai, J., Ruth, P., Bosse, E., Hofmann, F., Flockerzi, V., Furuichi, T., Mikoshiba, K., Imoto, K, Tanabe, T., and Numa, S. (1991) *Nature* 350,398–402

Singer, D., Biel, M., Lotan, I., Flockerzi, V., Hofmnann, F., and Dascal, N. (1991) *Science* 253,1553–1657

Ramsay, R. E. (1994) *Neurology* 44, Suppl. 5, 23–30

Watson, W. P., and Little, H. J. (1995) *Br. J: Pharmacol.* 116, 33P (abstr.)

Singh, L., Field, M. J., Ferris, P., Hunter, J. C., Oles, R. J., Williams, R. G., and Woodruff, G. N. (1996) *Psychopharmacology* 127, 1–9

Xiao, W. H., and Bennet, G. L (1995) *Soc. Neurosci.* 21, 897 (abstr.)

Mellick, G. A., Mellicy, L. B., and Mellick, L. B. (1995) *J. Pain Symptom Manage.* 10, 265–266

Shimoyama, N., Shimoyama, M., Davis, A. M., Inturrisi, C. E., and Elliott, K. J. (1997) *Neurosci. Lett.* 222, 65–67

SegaL A. Z., and Rordorf, G. (1996) *Neurology* 46, 1175–1176

Mellick, G. A., and Mellick, L. B. (1996) *Sleep* 19, 224–226

Patel, J., and Naritoku, D. K (1996) *Clin. Neuropharmacol.* 19, 185–188

Suman Chauhan, N., Webdale, L., Hill, D. R., and Woodruff, G. N. (1993) *Eur, J. Pharmacol.* 244, 293–301

Macdonald, R. L., and Kelly, F__M. (1993) *Epilepsia* 34, Suppl. 5, S1–S8

Taylor, C. P. (1994) *Neurology* 44, Suppl. 5, 10–16

Gotz, E., Feuerstein, T. J., Lais, A., and Meyer, D. K (1993) *Arzneimittelforschung* 43, 636–638

Loscher, W., Honack, D., and Taylor, C. P. (1991) *Neurosci. Lett* 128,150–154

Honmou, O., Knesis, J. D., and Richerson, G. B. (1995) *Epilepsy Res.* 20, 193–202

Honmou, O., Oyelese, A. A., and Kocsis, J. D. (1995) *Brain Res.* 692,273–277

Petroff, O. A. C., Rothman, D. L., Behar, K. L., Lamoureux, D., and Mattson, R. H. (1996) *Ann. Neurol.* 39, 95–99

Reimann, W. (1983) *Eur. J. Pharmacol.* 94, 341–344

Dooley, D. J., Bartoszyk, G. D., Hartenstein, J., Reimann, W., Rock, D. M., and Satzinger, G. (1986) *Golden Jubilee Conference and Northern European Epilepsy Meeting.* Abstracts, University of York, UK, September 1986 (Abstract 8).

Thurlow, R. J., Brown, J. P., Gee, N. S., Hill, D. R., and Woodruff, G. N. (1993) *Eur. J Pharmacol.* 247, 341–345

Gee, N. S., Brown, J. P., Dissanayake, V. U. I, Offord, J., Thurlow, R., and Woodruff, G. N. (1996) *J. Biol. Chem.* 271, 5768–5776

Dissanayake, V. U. I-, Gee, N. S., Brown, J. P., and Woodruff, G. N. (1997) *Br. J. Pharmacol.* 120, 833–840

Taylor, C. P., Vartanian, M. G., Yuen, P. W., Bigge, C., Suman Chauhan, N., and Hill, D. R. (1993) *Epilepsy Res.* 14,11–15

Rock, D. M., Kelly, K. M., and Macdonald, R. L. (1993) *Epilepsy Res.* 16, 89–98

Wamil, A. W., Mclean, M. J., Nashville, T. N., and Taylor, C. P. (1991) *Neurology* 41, Suppl. 1, 140 (abstr.)

De Jongh, K S., Warner, C., and Catterall, W. A. (1990) *J. Biol. Chem.* 265, 14738–14741

Jay, S. D., Sharp, A. H., Kahl, S. D., Vedvick, T. S., Harpold, M. M., and Campbell, K. P. (1991) *J. Biol. Chem.* 266, 3287–3293

Burgess, A. J., and Norman, R. 1. (1988) *Eur. J Biochem.* 178, 527–533

Ellis, S. B., Williams, M. E., Ways, N. R., Brenner, R., Sharp, A. H., Leung, A. T., Campbell, K. P., McKenna, E., Koch, W. J., Hai, A., Schwartz, A., and Harpold, M. M. (1988) *Science* 241, 1661–1664

Brickley, K., Campbell, V., Berrow, N., Leach, R., Norman, R. I., Wray, D., Dolphin, A. C., and Baldwin, S. A- (1995) *FEBS Lett.* 364,129–133

Brice, N. L., Berrow, N. S., Campbell, V., Page, K. M., Brickley, K., Tedder, I., Dolphin, A C. (1997) *Eur. J. Neurosci.* 9, 749–759

Wiser, O., Trus, M., Tobi, D., Halevi, S., Giladi, E., and Atlas, D. (1996) *FEBS Lett.* 379,15–20

Xu, X., and Arnason, U. (1994) *Gene (Amst.)* 148, 357–362

Williams, M. E., Feldman, D. H., McCue, A. F., Brenner, R., Velicelebi, G., Ellis, S. B., and Harpold, M. M. (1992) *Neuron* 8, 71–84

Kim, H. L., Kim, H., Lee, P., King, R. G., and Chin, H. (1992) *Proc. Natl. Acad Sci. U. S.A.* 89,3251–3255

Brown, J. P., Dissanayake, V. U. K., Briggs, A. R., Milic, M. R., and Gee, N. S. (1998) *Anal. Biochem.* 255, 236–243

Higuchi, R. (1990) in *PCR Protocols: A Guide to Methods and Applications* (Innis, M. A., Gelfand, D. H., Sninsky, J. J., and White, T. J. eds) pp. 177–183, Academic Press, Ltd., London Bradford, M. M. (1976) *Anal. Biochem.* 72, 248–252

Kyte, J., and Doolittle, F. (1982) *J. Mol. Biol.* 157, 105–132

Summers, M. F., Henderson, L. E., Chance, M. R., Bess, J. W., Jr., South, T. L., Blake, P. R., Sagi, I., Perez-Alvarado, G., Sowder, R. C., Hare, D. R., and Arthur, L. O. (1992) *Protein Sci.* 1, 563–574

Klug, A. and Rhodes, D. (1987) *Trends. Biochem. Sci.* 12, 464–469

Pieler, T., and Bellefroid, E. (1994) *Mol. Biol. Rep.* 20, 1–8

Preston, R. A., Manolson, M. F., Becherer, M, Weidenhammer, E., Kirkpatrick, D., Wright, R., and Jones, E. W. (1991) *Mol. Cell, Biol.* 11, 5801–5812

Tan, X., Waterham, H. R., Veenhuis, M., and Cregg, J. M. (1995) *J. Cell Biol.* 128,307–319

Scotland, P. B., Colledge, M., Melnikova, I., Dai, Z., and Froehner, S. C. (1993) *J. Cell Biol.* 123, 719–728

Henderson, L. E., Copeland, T. D., Sowder, R. C., Smythers, G. W., and Oroszlan, S. (1981) *J. Biol. Chem.* 256, 8400–8406

Beaucage et al., *Tetrahedron Lett* (1981) 22: 1859–1862.

Brown El.; Belagaje R, Ryan M J, Khorana H G, *Methods Enzymol* (1979); 68, 109–151.

Feldman and Steg, (1996) *Medecine/Sciences, synthese,* 12, 47–55.

Houbenweyl, (1974), *Meuthode der Organischen Chemie*, E. Wunsch Ed., Volume 15-I et 15-II, Thieme, Stuttgart.

Koch Y. (1977), *Biochem. Biophys. Res. Commun.,* 74, 488–491.

Kohler G. and Milstein C., (1975) *Nature,* 256, 495.

Kozbor et al., (1983) *Hybridoma,* 2(1), 7–16.

Leger O J, ct al. (1997) *Hum Antibodies,* 8(1), 3–16.

Martineau P, Jones P, Winter G. (1998), *J. Mol. Biol,* 280(1), 117–127.

Merrifield R B, 1965a, *Nature,* 207(996), 522–523.

Merrifield R B, 1965b, *Nature,* 207 (996), 22–523.

Narang S A, Hsiung H M, Brousseau R, *Methods Enzymol* 1979, 68, 90–98.

Ohno et al., (1994), *Science,* 265, 781–784.

O'Reilly et al., (1992) *Baculovirus expression vectors: a Laboratory Manual.* W. H. Freeman and Co., New York.

Ridder R. Schmitz R, Legay F, Gram H, (1995) *Biotechnology* (NY), 13(3), 255–260.

Smith et al., (1983), *Mol. Cell. Biol.,* 3, 2156–2165.

Sternberg N. L. (1992), *Trends Genet,* 8, 1–16.

Sternberg N. L. (1994) *Mamm. Genome,* 5, 397–404.

Sambrook, J. Fritsch, E. F. and T. Maniatis (1989). *Molecular cloning: a laboratory manual*, 2ed. Cold Spring Harbor Laboratory, Cold Spring Harbor, N.Y.

Sanchez-Pescador R., (1988), *J. Clin. Microbiol.,* 26(10), 1934–1938.

Urdea et al., MS (1988) *Nucleic Acids Research,* 11, 4937–4957.

Urdea et al., MS (1991) *Nucleic Acids Symp Ser.,* 24, 197–200.

SEQUENCE LISTING

1 - porcine nucleotide sequence alpha2 delta-1

```
GGGGATTGATCTTCGATCGCGAAGATGGCTGCTGGCTGCCTGCTGGCCTTGACTCTGACAC
TTTTCCAATCTTTGCTGATCGGTCCCTCATCGCAGGAGCCGTTCCCGTCGGCCGTCACTAT
CAAGTCATGGGTGGATAAAATGCAAGAAGACCTTGTCACCCTGGCAAAAACAGCAAGTGGA
GTCAATCAGCTTGTCGATATTTATGAAAAATACCAAGATTTGTATACTGTGGAACCAAATA
ATGCACGCCAGCTGGTGGAAATTGCAGCCAGGGATATTGAGAAACTTCTGAGCAACAGATC
TAAAGCCCTGGTGCGCCTAGCTTTGGAAGCAGAGAAGGTTCAAGCAGCCCACCAGTGGAGA
GAGGATTTTGCAAGCAATGAAGTTGTCTACTACAATGCAAAGGATGATCTCGATCCTGAAA
AAAATGACAGTGAGCCAGGCAGCCAGAGGATAAAACCTGTTTTTATTGATGATGCTAATTT
TGGGCGACAGATATCTTATCAGCATGCAGCAGTCCATATTCCCACCGACATCTATGAGGGC
TCAACAATTGTGTTAAATGAACTGAACTGGACAAGTGCCTTAGATGAAGTTTTCAAGAAAA
ATCGAGAGGAAGATCCCTCATTATTGTGGCAGGTGTTTGGCAGTGCCACAGGCCTGGCCCG
GTATTATCCAGCTTCTCCATGGGTTGATAACAGTAGAACTCCAAACAAGATTGACCTTTAT
GATGTACGAAGGAGACCATGGTACATCCAAGGAGCTGCATCTCCTAAAGATATGCTTATTC
TGGTCGACGTGAGTGGAAGTGTTAGTGGTTTGACGCTTAAACTGATCCGAACATCTGTCTC
TGAAATGTTGGAAACCCTCTCAGATGACGATTTTGTGAATGTAGCTTCATTTAACAGCAAT
GCCCAGGATGTAAGCTGTTTTCAACACCTTGTCCAAGCAAATGTAAGAAATAAGAAAGTGC
TGAAAGATGCAGTTAATAATATCACAGCAAAAGGAATCACAGATTACAAGAAGGGCTTTAG
TTTTGCTTTTGAACAACTGCTTAATTATAACGTTTCTAGAGCCAACTGCAATAAGATTATC
ATGTTGTTCACCGATGGAGGAGAAGAGAGAGCTCAGGAGATATTTGCCAAATACAACAAAG
ACAAAAAAGTACGTGTATTCACATTTTCAGTTGGTCAACATAATTATGACAGAGGACCTAT
TCAGTGGATGGCCTGTGAAAATAAAGGTTATTATTATGAAATTCCTTCCATTGGAGCAATC
AGAATCAATACTCAGGAATATTTGGATGTTCTGGGAAGACCAATGGTTTTAGCAGGAGACA
AAGCTAAGCAAGTCCAGTGGACAAACGTGTACCTGGATGCACTGGAACTGGGACTTGTCAT
TACTGGAACTCTTCCGGTCTTCAACATAACCGGCCAAAATGAAAATAAGACGAACTTAAAG
AACCAGCTGATTCTTGGTGTGATGGGAGTTGATGTATCTTTGGAAGATATTAAAAGACTGA
CACCACGTTTTACACTGTGCCCCAATGGCTATTACTTTGCAATTGATCCTAATGGCTATGT
TTTATTACATCCAAATCTTCAGCCAAAGAACCCCAAATCTCAGGAGCCAGTAACCTTGGAT
TTCCTTGATGCAGAATTAGAGAATGATATTAAAGTGGAGATCCGAAATAAAATGATAGATG
GAGAAAGTGGAGAAAAAACATTCAGAACTCTGGTTAAATCTCAAGATGAGAGATATATTGA
CAAAGGAAACAGGACATATACATGGACTCCTGTCAATGGCACAGATTACAGTTTGGCCTTG
GTATTACCAACCTACAGTTTTTACTATATAAAAGCCAAAATAGAAGAGACAATAACTCAGG
CCAGATCAAAAAAGGGCAAAATGAAGGATTCAGAAACACTGAAGCCTGATAATTTTGAAGA
ATCTGGCTATACATTCATAGCACCAAGAGACTACTGCAATGACCTTAAAATATCAGATAAT
AATACCGAATTTCTTTTAAACTTTAATGAGTTTATTGATAGAAAAACTCCAAACAACCCGT
CCAAAATTACTGGAGTAAGCAGTTTTTCATCAAGGGAGTGAAAGCACGGTTTGTTGTAACT
GATGGAGGGATTACCAGAGTTTATCCCAAAGAGGCTGGAGAAAATTGGCAAGAAACCCAG
AAACATATGAGGACAGCTTCTATAAAAGAAGTCTAGATAACGATAACTATGTTTTCACTGC
TCCCTACTTTAACAAAAGTGGACCTGGTGCTTATGAATCAGGCATCATGGTAAGCAAAGCT
```

-continued

SEQUENCE LISTING

GTAGAAATATACATCCAAGGAAAACTTCTTAAACCTGCAGTTGTTGGAATTAAAATTGATG

TAAATTCCTGGATAGAGAATTTCACCAAAACATCAATCAGGGATCCGTGTGCTGGTCCAGT

TTGTGATTGTAAAAGAAACAGTGATGTAATGGATTGTGTGATTCTAGATGATGGTGGGTTT

CTTTTGATGGCAAATCATGATGATTATACTAACCAGATTGGAAGGTTTTTTGGAGAGATTG

ACCCAAGTTTGATGAGACACCTGGTTAATATATCAGTTTATGCTTTTAACAAATCTTACGA

TTATCAGTCAGTGTGTGAGCCTGGTGCTGCACCAAAACAAGGAGCAGGACATCGCTCAGCA

TATGTGCCATCAATAGCAGACATCTTACACATTGGCTGGTGGGCCACTGCAGCTGCATGGT

CTATTCTACAGCAGTTTCTCTTGAGTTTGACCTTTCCACGACTTCTTGAAGCAGTTGAGAT

GGAAGATGATGACTTTACCGCCTCTCTGTCAAAGCAGAGTTGCATTACTGAACAAACCCAG

TATTTCTTTGATAATGATAGCAAATCCTTCAGTGGGTCTTGGACTGTGGTAACTGTTCCA

GAATCTTTCACGTTGAAAAACTTATGAACACCAACTTAATATTCATAATGGTTGAGAGCAA

AGGGACTTGTCCTTGTGACACACGATTGCTCATACAAGCTGAGCAGACTTCTGACGGTCCA

GATCCTTGTGATATGGTTAAGCAACCCAGATACCGAAAAGGGCCTGATGTCTGTTTTGATA

ACAATGCCTTGGAGGATTATACCGACTGTGGTGGTGTTTCTGGATTAAATCCCTCCCTGTG

GTCCATCTTCGGAATCCAGTGTGTTTTACTTTGGCTTTTATCTGGCAGCAGACACTACCAG

TTATGACCCTTCTAAAACCAAATCTGCATATTAAACTTCAGACCCTGCCAGAATAGGAGCC

CTCAATTGCATTAAAATAGGGTAAACTGCAGAATCAGCAGAACTCTAGCTGGGCCCATCCC

ATGGCATCAATCTCAGACTCATAAGGCACCCACTGGCTGCATGTCAGGGTATCAGATCCTG

AAACTTGTGTGAATGCTGCATCATCTATGTATAACATCAGAGCAAAATTCTATACCTATTC

TATTGGAAAATTTGAGAATTTGTTGTTGCATTGTTGGTGATTACATGTAAAAGGGCTCCCC

ACACAGTTGTGTATGAATCACGCAAATTGTCTTGATTTTGACTTGCTGCAATCCTTGTCCT

TTTACCAAGAAAATCTCTAGAGGGAAAAAAAAAGTCTTTTTTTTCCTTCACTAATTCTGCT

ACAAATTATTTCCTGCTTGGAGTAGTTATTATTAAAAAATATATATATAGAGAGAGAGA

GAGAATTAACATTGGTGTAATCTGTCAAAATAGAAATAATGGCTTATTTTCTACAAAAAA

2 - porcine nucleotide sequence

ATGGCTGCTGGCTGCCTGCTGGCCTTGACTCTGACACTTTTCCAATCTTTGCTGATCGGTC

CCTCATCGCAGGAGCCGTTCCCGTCGGCCGTCACTATCAAGTCATGGGTGGATAAAATGCA

AGAAGACCTTGTCACCCTGGCAAAAACAGCAAGTGGAGTCAATCAGCTTGTCGATATTTAT

GAAAAATACCAAGATTTGTATACTGTGGAACCAAATAATGCACGCCAGCTGGTGGAAATTG

CAGCCAGGGATATTGAGAAACTTCTGAGCAACAGATCTAAAGCCCTGGTGCGCCTAGCTTT

GGAAGCAGAGAAGGTTCAAGCAGCCCACCAGTGGAGAGAGGATTTTGCAAGCAATGAAGTT

GTCTACTACAATGCAAAGGATGATCTCGATCCTGAAAAAAATGACAGTGAGCCAGGCAGCC

AGAGGATAAAACCTGTTTTTATTGATGATGCTAATTTTGGGCGACAGATATCTTATCAGCA

TGCAGCAGTCCATATTCCCACCGACATCTATGAGGGCTCAACAATTGTGTTAAATGAACTG

AACTGGACAAGTGCCTTAGATGAAGTTTTCAAGAAAAATCGAGAGGAAGATCCCTCATTAT

TGTGGCAGGTGTTTGGCAGTGCCACAGGCCTGGCCCGGTATTATCCAGCTTCTCCATGGGT

TGATAACAGTAGAACTCCAAACAAGATTGACCTTTATGATGTACGAAGGAGACCATGGTAC

ATCCAAGGAGCTGCATCTCCTAAAGATATGCTTATTCTGGTCGACGTGAGTGGAAGTGTTA

SEQUENCE LISTING

```
GTGGTTTGACGCTTAAACTGATCCGAACATCTGTCTCTGAAATGTTGGAAACCCTCTCAGA

TGACGATTTTGTGAATGTAGCTTCATTTAACAGCAATGCCCAGGATGTAAGCTGTTTTCAA

CACCTTGTCCAAGCAAATGTAAGAAATAAGAAAGTGCTGAAAGATGCAGTTAATAATATCA

CAGCAAAAGGAATCACAGATTACAAGAAGGGCTTTAGTTTTGCTTTTGAACAACTGCTTAA

TTATAACGTTTCTAGAGCCAACTGCAATAAGATTATCATGTTGTTCACCGATGGAGGAGAA

GAGAGAGCTCAGGAGATATTTGCCAAATACAACAAAGACAAAAAAGTACGTGTATTCACAT

TTTCAGTTGGTCAACATAATTATGACAGAGGACCTATTCAGTGGATGGCCTGTGAAAATAA

AGGTTATTATTATGAAATTCCTTCCATTGGAGCAATCAGAATCAATACTCAGGAATATTTG

GATGTTCTGGGAAGACCAATGGTTTTAGCAGGAGACAAAGCTAAGCAAGTCCAGTGGACAA

ACGTGTACCTGGATGCACTGGAACTGGGACTTGTCATTACTGGAACTCTTCCGGTCTTCAA

CATAACCGGCCAAAATGAAAATAAGACGAACTTAAAGAACCAGCTGATTCTTGGTGTGATG

GGAGTTGATGTATCTTTGGAAGATATTAAAAGACTGACACCACGTTTTACACTGTGCCCCA

ATGGCTATTACTTTGCAATTGATCCTAATGGCTATGTTTTATTACATCCAAATCTTCAGCC

AAAGAACCCCAAATCTCAGGAGCCAGTAACCTTGGATTTCCTTGATGCAGAATTAGAGAAT

GATATTAAAGTGGAGATCCGAAATAAAATGATAGATGGAGAAAGTGGAGAAAAAACATTCA

GAACTCTGGTTAAATCTCAAGATGAGAGATATATTGACAAAGGAAACAGGACATATACATG

GACTCCTGTCAATGGCACAGATTACAGTTTGGCCTTGGTATTACCAACCTACAGTTTTTAC

TATATAAAAGCCAAAATAGAAGAGACAATAACTCAGGCCAGATCAAAAAAGGGCAAAATGA

AGGATTCAGAAACACTGAAGCCTGATAATTTTGAAGAATCTGGCTATACATTCATAGCACC

AAGAGACTACTGCAATGACCTTAAAATATCAGATAATAATACCGAATTTCTTTTAAACTTT

AATGAGTTTATTGATAGAAAAACTCCAAACAACCCGTCATGCAACACAGATTTGATTAATA

GAGTCTTGCTGGATGCGGGCTTTACAAATGAACTTGTCCAAAATTACTGGAGTAAGCAGAA

AAACATCAAGGGAGTGAAAGCACGGTTTGTTGTAACTGATGGAGGGATTACCAGAGTTTAT

CCCAAAGAGGCTGGAGAAAATTGGCAAGAAAACCCAGAAACATATGAGGACAGCTTCTATA

AAAGAAGTCTAGATAACGATAACTATGTTTTCACTGCTCCCTACTTTAACAAAAGTGGACC

TGGTGCTTATGAATCAGGCATCATGGTAAGCAAAGCTGTAGAAATATACATCCAAGGAAAA

CTTCTTAAACCTGCAGTTGTTGGAATTAAAATTGATGTAAATTCCTGGATAGAGAATTTCA

CCAAAACATCAATCAGGGATCCGTGTGCTGGTCCAGTTTGTGATTGTAAAAGAAACAGTGA

TATAATGGATTGTGTGATTCTAGATGATGGTGGGTTTCTTTTGATGGCAAATCATGATGAT

TATACTAACCAGATTGGAAGGTTTTTTGGAGAGATTGACCCAAGTTTGATGAGACACCTGG

TTAATATATCAGTTTATGCTTTTAACAAATCTTACGATTATCAGTCAGTGTGTGAGCCTGG

TGCTGCACCAAAACAAGGAGCAGGACATCGCTCAGCATATGTGCCATCAATAGCAGACATC

TTACACATTGGCTGGTGGGCCACTGCAGCTGCATGGTCTATTCTACAGCAGTTTCTCTTGA

GTTTGACCTTTCCACGACTTCTTGAAGCAGTTGAGATGGAAGATGATGACTTTACCGCCTC

TCTGTCAAAGCAGAGTTGCATTACTGAACAAACCCAGTATTTCTTTGATAATGATAGCAAA

TCCTTCAGTGGGGTCTTGGACTGTGGTAACTGTTCCAGAATCTTTCACGTTGAAAAACTTA
```

TGAACACCAACTTAATATTCATAATGGTTGAGAGCAAAGGGACTTGTCCTTGTGACACACG
ATTGTGA

3 - porcine nucleotide sequence

ATGGCTGCTGGCTGCCTGCTGGCCTTGACTCTGACACTTTTCCAATCTTTGCTGATCGGTC
CCTCATCGCAGGAGCCGTTCCCGTCGGCCGTCACTATCAAGTCATGGGTGGATAAAATGCA
AGAAGACCTTGTCACCCTGGCAAAAACAGCAAGTGGAGTCAATCAGCTTGTCGATATTTAT
GAAAAATACCAAGATTTGTATACTGTGGAACCAAATAATGCACGCCAGCTGGTGGAAATTG
CAGCCAGGGATATTGAGAAACTTCTGAGCAACAGATCTAAAGCCCTGGTGCGCCTAGCTTT
GGAAGCAGAGAAGGTTCAAGCAGCCCACCAGTGGAGAGAGGATTTTGCAAGCAATGAAGTT
GTCTACTACAATGCAAAGGATGATCTCGATCCTGAAAAAAATGACAGTGAGCCAGGCAGCC
AGAGGATAAAACCTGTTTTTATTGATGATGCTAATTTTGGGCGACAGATATCTTATCAGCA
TGCAGCAGTCCATATTCCCACCGACATCTATGAGGGCTCAACAATTGTGTTAAATGAACTG
AACTGGACAAGTGCCTTAGATGAAGTTTTCAAGAAAAATCGAGAGGAAGATCCCTCATTAT
TGTGGCAGGTGTTTGGCAGTGCCACAGGCCTGGCCCGGTATTATCCAGCTTCTCCATGGGT
TGATAACAGTAGAACTCCAAACAAGATTGACCTTTATGATGTACGAAGGAGACCATGGTAC
ATCCAAGGAGCTGCATCTCCTAAAGATATGCTTATTCTGGTCGACGTGAGTGGAAGTGTTA
GTGGTTTGACGCTTAAACTGATCCGAACATCTGTCTCTGAAATGTTGGAAACCCTCTCAGA
TGACGATTTTGTGAATGTAGCTTCATTTAACAGCAATGCCCAGGATGTAAGCTGTTTTCAA
CACCTTGTCCAAGCAAATGTAAGAAATAAGAAAGTGCTGAAAGATGCAGTTAATAATATCA
CAGCAAAAGGAATCACAGATTACAAGAAGGGCTTTAGTTTTGCTTTTGAACAACTGCTTAA
TTATAACGTTTCTAGAGCCAACTGCAATAAGATTATCATGTTGTTCACCGATGGAGGAGAA
GAGAGAGCTCAGGAGATATTTGCCAAATACAACAAAGACAAAAAAGTACGTGTATTCACAT
TTTCAGTTGGTCAACATAATTATGACAGAGGACCTATTCAGTGGATGGCCTGTGAAAATAA
AGGTTATTATTATGAAATTCCTTCCATTGGAGCAATCAGAATCAATACTCAGGAATATTTG
GATGTTCTGGGAAGACCAATGGTTTTAGCAGGAGACAAAGCTAAGCAAGTCCAGTGGACAA
ACGTGTACCTGGATGCACTGGAACTGGGACTTGTCATTACTGGAACTCTTCCGGTCTTCAA
CATAACCGGCCAAAATGAAAATAAGACGAACTTAAAGAACCAGCTGATTCTTGGTGTGATG
GGAGTTGATGTATCTTTGGAAGATATTAAAAGACTGACACCACGTTTTACACTGTGCCCCA
ATGGCTATTACTTTGCAATTGATCCTAATGGCTATGTTTTATTACATCCAAATCTTCAGCC
AAAGAACCCCAAATCTCAGGAGCCAGTAACCTTGGATTTCCTTGATGCAGAATTAGAGAAT
GATATTAAAGTGGAGATCCGAAATAAAATGATAGATGGAGAAAGTGGAGAAAAAACATTCA
GAACTCTGGTTAAATCTCAAGATGAGAGATATATTGACAAAGGAAACAGGACATATACATG
GACTCCTGTCAATGGCACAGATTACAGTTTGGCCTTGGTATTACCAACCTACAGTTTTTAC
TATATAAAAGCCAAAATAGAAGAGACAATAACTCAGGCCAGATCAAAAAAGGGCAAAATGA
AGGATTCAGAAACACTGAAGCCTGATAATTTTGAAGAATCTGGCTATACATTCATAGCACC
AAGAGACTACTGCAATGACCTTAAAATATCAGATAATAATACCGAATTTCTTTTAAACTTT
AATGAGTTTATTGATAGAAAAACTCCAAACAACCCGTCATGCAACACAGATTTGATTAATA
GAGTCTTGCTGGATGCGGGCTTTACAAATGAACTTGTCCAAAATTACTGGAGTAAGCAGAA

-continued

SEQUENCE LISTING

AAACATCAAGGGAGTGAAAGCACGGTTTGTTGTAACTGATGGAGGGATTACCAGAGTTTAT

CCCAAAGAGGCTGGAGAAAATTGGCAAGAAAACCCAGAAACATATGAGGACAGCTTCTATA

AAAGAAGTCTAGATAACGATAACTATGTTTTCACTGCTCCCTACTTTAACAAAAGTGGACC

TGGTGCTTATGAATCAGGCATCATGGTAAGCAAAGCTGTAGAAATATACATCCAAGGAAAA

CTTCTTAAACCTGCAGTTGTTGGAATTAAAATTGATGTAAATTCCTGGATAGAGAATTTCA

CCAAAACATCAATCAGGGATCCGTGTGCTGGTCCAGTTTGTGATTGTAAAAGAAACAGTGA

TGTAATGGATTGTGTGATTCTAGATGATGGTGGGTTTCTTTTGATGGCAAATCATGATGAT

TATACTAACCAGATTGGAAGGTTTTTTGGAGAGATTGACCCAAGTTTGATGAGACACCTGG

TTAATATATCAGTTTATGCTTTTAACAAATCTTACGATTATCAGTCAGTGTGTGAGCCTGG

TGCTGCACCAAAACAAGGAGCAGGACATCGCTCAGCATATGTGCCATCAATAGCAGACATC

TTACACATTGGCTGGTGGGCCACTGCAGCTGCATGGTCTATTCTACAGCAGTTTCTCTTGA

GTTTGACCTTTCCACGACTTCTTGAAGCAGTTGAGATGGAAGATGATGACTTTACCGCCTC

TCTGTCAAAGCAGAGTTGCATTACTGAACAAACCCAGTATTTCTTTGATAATGATAGCAAA

TCCTTCAGTGGGGTCTTGGACTGTGGTAACTGTTCCAGAATCTTTCACGTTGAAAAACTTA

TGAACACCAACTTAATATTCATAATGGTTGAGAGCAAAGGGACTTGTCCTTGTGACACACG

ATTGCTCATACAAGCTGAGCAGACTTCTGACGGTCCAGATCCTTGTGATATGGTTAAGTGA

4 - porcine nucleotide sequence

ATGGCTGCTGGCTGCCTGCTGGCCTTGACTCTGACACTTTTCCAATCTTTGCTGATCGGTC

CCTCATCGCAGGAGCCGTTCCCGTCGGCCGTCACTATCAAGTCATGGGTGGATAAAATGCA

AGAAGACCTTGTCACCCTGGCAAAAACAGCAAGTGGAGTCAATCAGCTTGTCGATATTTAT

GAAAAATACCAAGATTTGTATACTGTGGAACCAAATAATGCACGCCAGCTGGTGGAAATTG

CAGCCAGGGATATTGAGAAACTTCTGAGCAACAGATCTAAAGCCCTGGTGCGCCTAGCTTT

GGAAGCAGAGAAGGTTCAAGCAGCCCACCAGTGGAGAGAGGATTTTGCAAGCAATGAAGTT

GTCTACTACAATGCAAAGGATGATCTCGATCCTGAAAAAAATGACAGTGAGCCAGGCAGCC

AGAGGATAAAACCTGTTTTTATTGATGATGCTAATTTTGGGCGACAGATATCTTATCAGCA

TGCAGCAGTCCATATTCCCACCGACATCTATGAGGGCTCAACAATTGTGTTAAATGAACTG

AACTGGACAAGTGCCTTAGATGAAGTTTTCAAGAAAAATCGAGAGGAAGATCCCTCATTAT

TGTGGCAGGTGTTTGGCAGTGCCACAGGCCTGGCCCGGTATTATCCAGCTTCTCCATGGGT

TGATAACAGTAGAACTCCAAACAAGATTGACCTTTATGATGTACGAAGGAGACCATGGTAC

ATCCAAGGAGCTGCATCTCCTAAAGATATGCTTATTCTGGTCGACGTGAGTGGAAGTGTTA

GTGGTTTGACGCTTAAACTGATCCGAACATCTGTCTCTGAAATGTTGGAAACCCTCTCAGA

TGACGATTTTGTGAATGTAGCTTCATTTAACAGCAATGCCCAGGATGTAAGCTGTTTTCAA

CACCTTGTCCAAGCAAATGTAAGAAATAAGAAAGTGCTGAAAGATGCAGTTAATAATATCA

CAGCAAAAGGAATCACAGATTACAAGAAGGGCTTTAGTTTTGCTTTTGAACAACTGCTTAA

TTATAACGTTTCTAGAGCCAACTGCAATAAGATTATCATGTTGTTCACCGATGGAGGAGAA

GAGAGAGCTCAGGAGATATTTGCCAAATACAACAAAGACAAAAAAGTACGTGTATTCACAT

TTTCAGTTGGTCAACATAATTATGACAGAGGACCTATTCAGTGGATGGCCTGTGAAAATAA

AGGTTATTATTATGAAATTCCTTCCATTGGAGCAATCAGAATCAATACTCAGGAATATTTG

GATGTTCTGGGAAGACCAATGGTTTTAGCAGGAGACAAAGCTAAGCAAGTCCAGTGGACAA

SEQUENCE LISTING

```
ACGTGTACCTGGATGCACTGGAACTGGGACTTGTCATTACTGGAACTCTTCCGGTCTTCAA

CATAACCGGCCAAAATGAAAATAAGACGAACTTAAAGAACCAGCTGATTCTTGGTGTGATG

GGAGTTGATGTATCTTTGGAAGATATTAAAAGACTGACACCACGTTTTACACTGTGCCCCA

ATGGCTATTACTTTGCAATTGATCCTAATGGCTATGTTTTATTACATCCAAATCTTCAGCC

AAAGAACCCCAAATCTCAGGAGCCAGTAACCTTGGATTTCCTTGATGCAGAATTAGAGAAT

GATATTAAAGTGGAGATCCGAAATAAAATGATAGATGGAGAAAGTGGAGAAAAAACATTCA

GAACTCTGGTTAAATCTCAAGATGAGAGATATATTGACAAAGGAAACAGGACATATACATG

GACTCCTGTCAATGGCACAGATTACAGTTTGGCCTTGGTATTACCAACCTACAGTTTTTAC

TATATAAAAGCCAAAATAGAAGAGACAATAACTCAGGCCAGATCAAAAAAGGGCAAAATGA

AGGATTCAGAAACACTGAAGCCTGATAATTTTGAAGAATCTGGCTATACATTCATAGCACC

AAGAGACTACTGCAATGACCTTAAAATATCAGATAATAATACCGAATTTCTTTTAAACTTT

AATGAGTTTATTGATAGAAAAACTCCAAACAACCCGTCATGCAACACAGATTTGATTAATA

GAGTCTTGCTGGATGCGGGCTTTACAAATGAACTTGTCCAAAATTACTGGAGTAAGCAGAA

AAACATCAAGGGAGTGAAAGCACGGTTTGTTGTAACTGATGGAGGGATTACCAGAGTTTAT

CCCAAAGAGGCTGGAGAAAATTGGCAAGAAAACCCAGAAACATATGAGGACAGCTTCTATA

AAAGAAGTCTAGATAACGATAACTATGTTTTCACTGCTCCCTACTTTAACAAAAGTGGACC

TGGTGCTTATGAATCAGGCATCATGGTAAGCAAAGCTGTAGAAATATACATCCAAGGAAAA

CTTCTTAAACCTGCAGTTGTTGGAATTAAAATTGATGTAAATTCCTGGATAGAGAATTTCA

CCAAAACATCAATCAGGGATCCGTGTGCTGGTCCAGTTTGTGATTGTAAAAGAAACAGTGA

TGTAATGGATTGTGTGATTCTAGATGATGGTGGGTTTCTTTTGATGGCAAATCATGATGAT

TATACTAACCAGATTGGAAGGTTTTTTGGAGAGATTGACCCAAGTTTGATGAGACACCTGG

TTAATATATCAGTTTATGCTTTTAACAAATCTTACGATTATCAGTCAGTGTGTGAGCCTGG

TGCTGCACCAAAACAAGGAGCAGGACATCGCTCAGCATATGTGCCATCAATAGCAGACATC

TTACACATTGGCTGGTGGGCCACTGCAGCTGCATGGTCTATTCTACAGCAGTTTCTCTTGA

GTTTGACCTTTCCACGACTTCTTGAAGCAGTTGAGATGGAAGATGATGACTTTACCGCCTC

TCTGTCAAAGCAGAGTTGCATTACTGAACAAACCCAGTATTTCTTTGATAATGATAGCAAA

TCCTTCAGTGGGGTCTTGGACTGTGGTAACTGTTCCAGAATCTTTCACGTTGAAAAACTTA

TGAACACCAACTTAATATTCATAATGGTTGAGAGCAAAGGGACTTGTCCTTGTGACACACG

ATTGCTCATACAAGCTGAGCAGACTTCTGACGGTCCAGATCCTTGTGATATGGTTAAGCAA

CCCAGATACCGAAAAGGGCCTGATGTCTGTTTTGATAACAATGCCTTGGAGGATTATACCG

ACTGTGGTGGTGTTTCTTGA
```

5 - porcine amino acid sequence alpha2 delta-1

```
MAAGCLLALTLTLFQSLLIGPSSQEPFPSAVTIKSWVDKMQEDLVTLAKTASGVNQLVDIY

EKYQKLYTVEPNNARQLVEIAARDIEKLLSNRSKALVRLALEAEKVQAAHQWREDFASNEV

VYYNAKDDLDPEKNDSEPGSQRIKPVFIDDANFGRQISYQHAAVHIPTDIYEGSTIVLNEL

NWTSALDEVFKKNREEDPSLLWQVFGSATGLARYYPASPWVDNSRTPNKIDLYDVRRRPWY

IQGAASPKDMLILVDVSGSVSGLTLKLIRTSVSEMLETLSDDDFVNVASFNSNAQDVSCFQ

HLVQANVRNKKVLKDAVNNITAKGITDYKKGFSFAFEQLLNYNVSRANCNKIIMLFTDGGE
```

SEQUENCE LISTING

ERAQEIFAKYNKDKKVRVFTFSVGQHNYDRGPIQWMACENKGYYYEIPSIGAIRINTQEYL

DVLGRPMVLAGDKAKQVQWTNVYLDALELGLVITGTLPVFNITGQNENKTNLKNQLILGVM

GVDVSLEDIKRLTPRFTLCPNGYYFAIDPNGYVLLHPNLQPKNPKSQEPVTLDFLDAELEN

DIKVEIRNKMIDGESGEKTFRTLVKSQDERYIDKGNRTYTWTPVNGTDYSLALVLPTYSFY

YIKAKIEETITQARSKKGKMKDSETLKPKNFEESGYTFIAPRDYCNDLKISDNNTEFLLNF

NEFIDRKTPNNPSCNTDLINRVLLDAGFTNELVQNYWSKQKNIKGVKARFVVTDGGITRVY

PKEAGENWQENPETYEDSFYKRSLDNDNYVFTAPYFNKSGPGAYESGIMVSKAVEIYIQGK

LLKPAVVGIKIDVNSWIENFTKTSIRDPCAGPVCDCKRNSDVMDCVILDDGGFLLMANHDD

YTNQIGRFFGEIDPSLMRHLVNISVYAFNKSYDYQSVCEPGAAPKQGAGHRSAYVPSIADI

LHIGWWATAAAWSILQQFLLSLTFPRLLEAVEMEDDDFTASLSKQSCITEQTQYFFDNDSK

SFSGVLDCGNCSRIFHVEKLMNTNLIFIMVESKGTCPCTTRLLIQAEQTSDGPDPCDMVKQ

PRYRKGPDVCFDNNALEDYTDCGGVSGLNPSLWSIFGIQCVLLWLLSGSRHYQL

6 - porcine amino acid sequence

MAAGCLLALTLTLEQSLLIGPSSQEPFPSAVTIKSWVDKMQEDLVTLAKTASGVNQLVDIK

EKYQDLYTVEPNNARQLVEIAARDIEKLLSNRSKALVRLALEAEKVQAAHQWREDFASNEV

VYYNAKDDLDPEKNDSEPGSQRIKPVFIDDANFGRQISYQHAAVHIPTDIYEGSTIVLNEL

NWTSALDEVFKKNREEDPSLLWQVFGSATGLARYYPASPWVDNSRTPNKIDLYDVRRRPWY

IQGAASPKDMLILVDVSGSVSGLTLKLIRTSVSEMLETLSDDDFVNVASFNSNAQDVSCFQ

HLVQANVRNKKVLKDAVNNITAKGITDYKKGFSFAFEQLLNYNVSRANCNKIIMLFTDGGE

ERAQEIFAKYNKDKKVRVFTFSVGQHNYDRGPIQWMACENKGYYYEIPSIGAIRINTQEYL

DVLGRPMVLAGDKAKQVQWTNVYLDALELGLVITGTLPVFNITGQNENKTNLKNQLILGVM

GVDVSLEDIKRLTPRFTLCPNGYYFAIDPNGYVLLHPNLQPKNPKSQEPVTLDFLDAELEN

DIKVEIRNKMIDGESGEKTFRTLVKSQDERYIDKGNRTYTWTPVNGTDYSLALVLPTYSFY

YIKAKIEETITQARSKKGKMKDSETLKPDNFEESGYTFIAPRDYCNDLKISDNNTEFLLNF

NEFIDRKTPNNPSCNTDLINRVLLDAGFTNELVQNYWSKQKNIKGVKARFVVTDGGITRVY

PKEAGENWQENPETYEDSFYKRSLDNDNYVFTAPYFNKSGPGAYESGIMVSKAVEIYIQGK

LLKPAVVGIKIDVNSWIENFTKTSIRDPCAGPVCDCKRNSDVMDCVILDDGGFLLMANHDD

YTNQIGRFFGEIDPSLMRHLVNISVYAFNKSYDYQSVCEPGAAPKQGAGHRSAYVPSIADI

LHIGWWATAAAWSILQQFLLSLTFPRLLEAVEMEDDDFTASLSKQSCITEQTQYFFDNDSK

SFSGVLDCGNCSRIFHVEKLMNTNLIFIMVESKGTCPCDTRL

7 - porcine amino acid sequence

MAAGCLLALTLTLFQSLLIGPSSQEPFPSAVTIKSWVDKMQEDLVTLAKTASGVNQLVDIY

EKYQDLYTVEPNNARQLVEIAARDIEKLLSNRSKALVRLALEAEKVQAAHQWREDFASNEV

VYYNAKDDLDPEKNDSEPGSQRIKPVFIDDANFGRQISYQHAAVHIPTDIYEGSTIVLNEL

NWTSALDEVFKKNREEDPSLLWQVFGSATGLARYYPASPWVDNSRTPNKIDLYDVRRRPWY

IQGAASPKDMLILVDVSGSVSGLTLKLIRTSVSEMLETLSDDDFVNVASFNSNAQDVSCFQ

HLVQANVRNKKVLKDAVNNITAKGITDYKKGFSFAFEQLLNYNVSRANCNKIIMLFTDGGE

ERAQEIFAKYNKDKKVRVFTFSVGQHNYDRGPIQWMACENKGYYYEIPSIGAIRINTQEYL

DVLGRPMVLAGDKAKQVQWTNVYLDALELGLVITGTLPVFNITGQNENKTNLKNQLILGVM

SEQUENCE LISTING

GVDVSLEDIKRLTPRFTLCPNGYYFAIDPNGYVLLHPNLQPKNPKSQEPVTLDFLDAELEN

DIKVEIRNKMIDGESGEKTFRTLVKSQDERYIDKGNRTYTWTPVNGTDYSLALVLPTYSFY

YIKAKIEETITQARSKKGKMKDSETLKPDNFEESGYTFIAPRDYCNDLKISDNNTEFLLNF

NEFIDRKTPNNPSCNTDLINRVLLDAGFTNELVQNYWSKQKNIKGVKARFVVTDGGITRVY

PKEAGENWQENPETYEDSFYKRSLDNDNYVFTAPYFNKSGPGAYESGIMVSKAVEIYIQGK

LLKQAVVGIKIDVNSWIENFTKTSIRDPCAGPVCDCKRNSDVMDCVILDDGGFLLMANHDD

YTNQIGRFFGEIDPSLMRHLVNISVYAFNKSYDYQSVCEPGAAPKQGAGHRSAYVPSIADI

LHIGWWATAAAWSILQQFLLSLTFPRLLEAVEMEDDDFTASLSKQSCITEQTQYFFDNDSK

SFSGVLDCGNCSRIFHVEKIMNTNLIFIMVESKGTCPCDTRLLIQAEQTSDGPDPCDMVK

8 - procine amino acid sequence

MAAGCLLALTLTLFQSLLIGPSSQEPFPSAVTIKSWVDKMQEDLVTLAKTASGVNQLVDIY

EKYQDLYTVEPNNARQLVEIAARDIEKLLSNRSKALVRLALEAEKVQAAHQWREDFASNEV

VYYNAKDDLDPEKNDSEPGSQRIKPVFIDDANFGRQISYQHAAVHIPTDIYEGSTIVLNEL

NWTSALDEVFKKNREEDPSLLWQVFGSATGLARYYPASPWVDNSRTPNKIDLYDVRRRPWY

IQGAASPKDMLILVDVSGSVSGLTLKLIRTSVSEMLETLSDDDFVNVASFNSNAQDVSCFQ

HLVQANVRNKKVLKDAVNNITAKGITDYKKGFSFAFEQLLNYNVSRANCNKIIMLFTDGGE

ERAQEIFAKYNKDKKVRVFTFSVGQHNYDRGPIQWMACENKGYYYEIPSIGAIRINTQEYL

DVLGRPMVLAGDKAKQVQWTNVYLDALELGLVITGTLPVFNITGQNENKTNLKNQLILGVM

GVDVSLEDIKRLTPRFTLCPNGYYFAIDPNGYVLLHPNLQPKNPKSQEPVTLDFLDAELEN

DIKVEIRNKMIDGESGEKTFRTLVKSQDERYIDKGNRTYTWTPVNGTDYSLALVLPTYSFY

YIKAKIEETITQARSKKGKMKDSETLKPDNFEESGYTFIAPRDYCNDLKISDNNTEFLLNF

NEFIDRKTPNNPSCNTDLINRVLLDAGFTNELVQNYWSKQKNIKGVKARFVVTDGGITRVY

PKEAGENWQENPETYEDSFYKRSLDNDNYVFTAPYFNKSGPGAYESGIMVSKAVEIYIQGK

LLKPAVVGIKIDVNSWIENFTKTSIRDPCAGPVCDCKRNSDVMDCVILDDGGFLIMANHDD

YTNQIGRFFGEIDPSLMRHLVNISVYAFNKSYDYQSVCEPGAAPKQGAGHRSAYVPSIADI

LHIGWWATAAAWSILQQFLLSLTFPRLLEAVEMEDDDFTASLSKQSCITEQTQYFFDNDSK

SFSGVLDCGNCSRIFHVEKLMNTNLIFIMVESKGTCPCDTRLLIQAEQTSDGPDPCDMVKQ

PRYRKGPDVCFDNNALEDYTDCGGVS

9 - nucleic acid sequence

GGGGATTGATCTTCGATCGCG

10 - nucleic acid sequence

CTGAGATTTGGGGTTCTTTGG

11 - peptide sequence

VEMEDDDFTASLSKQSC

12 - nucleic acid sequence

TGGCTTATCGAAATTAATACG

SEQUENCE LISTING

13 - nucleic acid sequence

AACTCCGGGGATTGATCTTCG

14 - human amino acid sequence alpha2 delta-1

MAAGCLLALTLTLFQSLLIGPSSEEPFPSAVTIKSWVDKMQEDLVTLAKTASGVNQLVDIY
EKYQDLYTVEPNNARQLVEIAARDIEKLLSNRSKALVSLALEAEKVQAAHQWREDFASNEV
VYYNAKDDLDPEKNDSEPGSQRIKPVFIEDANFGRQISYQHAAVHIPTDIYEGSTIVLNEL
NWTSALDEVFKKNREEDPSLLWQVFGSATGLARYYPASPWVDNSRTPNKIDLYDVRRRPWY
IQGAASPKDMLILVDVSGSVSGLTLKLIRTSVSEMLETLSDDDFVNVASFNSNAQDVSCFQ
HLVQANVRNKKVLKDAVNNITAKGITDYKKGFSFAFEQLLNYNVSRANCNKIIMLFTDGGE
ERAQEIFNKYNKDKKVRVFRFSVGQHNYERGPIQWMACENKGYYYEIPSIGAIRINTQEYL
DVLGRPMVLAGDKAKQVQWTNVYLDALELGLVITGTLPVFNITGQFENKTNLKNQLILGVM
GVDVSLEDIKRLTPRFTLCPNGYYFAIDPNGYVLLHPNLQPKNPKSQEPVTLDFLDAELEN
DIKVEIRNKMIDGESGEKTFRTLVKSQDERYIDKGNRTYTWTPVNGTDYSLALVLPTYSFY
YIKAKLEETITQARSKKGKMKDSETLKPDNFEESGYTFIAPRDYCNDLKISDNNTEFLLNF
NEFIDRKTPNNPSCNADLINRVLLDAGFTNELVQNYWSKQKNIKGVKARFVVTDGGITRVY
PKEAGENWQENPETYEDSFYKRSLDNDNYVFTAPYFNKSGPGAYESGIMVSKAVEIYIQGK
LLKPAVVGIKIDVNSWIENFTKTSIRDPCAGPVCDCKRNSDVMDCVILDDGGFLLMANHDD
YTNQIGRFFGEIDPSLMRHLVNISVYAFNKSYDYQSVCEPGAAPKQGAGHRSAYVPSVADI
LQIGWWATAAAWSILQQFLLSLTFPRLLEAVEMEDDDFTASLSKQSCITEQTQYFFDNDSK
SFSGVLDCGNCSRIFHGEKLMNTNLIFIMVESKGTCPCDTRLLIQAEQTSKGPNPCDMVKQ
PRYRKGPDVCFDNNVLEDYTDCGGVSGLNPSLWYIIGIQFLLLWLVSGSTHRLL

15 - human amino acid sequence alpha2 delta-1

MAAGCLLALTLTLFQSLLIGPSSEEPFPSAVTIKSWVDKMQEDLVTLAKTASGVNQLVDIY
EKYQDLYTVEPNNARQLVEIAARDIEKLLSNRSKALVSLALEAEKVQAAHQWREDFASNEV
VYYNAKDDLDPEKNDSEPGSQRIKPVFIEDANFGRQISYQHAAVHIPTDIYEGSTIVLNEL
NWTSALDEVFKKNREEDPSLLWQVFGSATGLARYYPASPWVDNSRTPNKIDLYDVRRRPWY
IQGAASPKDMLILVDVSGSVSGLTLKLIRTSVSEMLETLSDDDFVNVASFNSNAQDVSCFQ
HLVQANVRNKKVLKDAVNNITAKGITDYKKGFSFAFEQLLNYNVSRANCNKIIMLFTDGGE
ERAQEIFNKYNKDKKVRVFRFSVGQHNYERGPIQWMACENKGYYYEIPSIGAIRINTQEYL
DVLGRPMVLAGDKAKQVQWTNVYLDALELGLVITGTLPVFNITGQFENKTNLKNQLILGVM
GVDVSLEDIKRLTPRFTLCPNGYYFAIDPNGYVLLHPNLQPKNPKSQEPVTLDFLDAELEN
DIKVEIRNEMIDGESGEKTFRTLVKSQDERYIDKGNRTYTWTPVNGTDYSLALVLPTYSFY
YIKAKLEETITQARSKKGKMKDSETLKPDNFEESGYTFIAPRDYCNDLKISDNNTEFLLNF
NEFIDRKTPNNPSCNADLINRVLLDAGFTNELVQNTWSKQKNIKGVKARFVVTDGGITRVY
PKEAGENWQENPETYEDSFYKRSLDNDNYVFTAPYFNKSGPGAYESGIMVSKAVEIYIQGK
LLKPAVVGIKIDVNSWIENFTKTSIRDPCAGPVCDCKRNSDVMDCVILDDGGFLLMANHDD
YTNQIGRFFGEIDPSLMRHLVNISVYAFNKSYDYQSVCEPGAAPKQGAGHRSAYVPSVADI

LQIGWWATAAAWSILQQFLLSLTFPRLLEAVEMEDDDFTASLSKQSCITEQTQYFFDNDSK

SFSGVLDCGNCSRIFHGEKLMNTNLIFIMVESKGTCPCKTRL

16 - human amino acid sequence alpha2 delta-1

MAAGCLLALTLTLFQSLLIGPSSEEPFPSAVTIKSWVDKMQEDLVTLAKTASGVNQLVDIY

EKYQDLYTVEPNNARQLVEIAARDIEKLLSNRSKALVSLALEAEKVQAAHQWREDFASNEV

VYYNAKDDLDPEKNDSEPGSQRIKPVFIEDANFGRQISYQHAAVHIPTDIYEGSTIVLNEL

NWTSALDEVFKKNREEDPSLLWQVFGSATGLARYYPASPWVDNSRTPNKIDLYDVRRRPWY

IQGAASPKDMLILVDVSGSVSGLTLKLIRTSVSEMLETLSDDDFVNVASFNSNAQDVSCFQ

HLVQANVRNKKVLKDAVNNITAKGITDYKKGFSFAFEQLLNYNVSRANCNKIIMLFTDGGE

ERAQEIFNKYNKDKKVRVFRFSVGQHNYERGPIQWMACENKGYYYEIPSIGAIRINTQEYL

DVLGRPMVLAGDKAKQVQWTNVYLDALELGLVITGTLPVFNITGQFENKTNLKNQLILGVM

GVDVSLEDIKRLTPRFTLCPNGYYFAIDPNGYVLLHPNLQPKNPKSQEPVTLDFLDAELEN

DIKVEIRNKMIDGESGEKTFRTLVKSQDERYIDKGNRTYTWTPVNGTDYSLALVLPTYSFY

YIKAKLEETITQARSKKGKMKDSETLKPDNFEESGYTFIAPRDYCNDLKISDNNTEFLLNF

NEFIDRKTPNNPSCNADLINRVLLDAGFTNELVQNYWSKQKNIKGVKARFVVTDGGITRVY

PKEAGENWQENPETYEDSFYKRSLDNDNYVFTAPYFNKSGPGAYESGIMVSKAVEIYIQGK

LLKPAVVGIKIDVNSWIENFTKTSIRDPCAGPVCDCKRNSDVMDCVILDDGGFLLMANHDD

YTNQIGRFFGEIDPSLMRHLVNISVYAFNKSYDYQSVCEPGAAPKQGAGHRSAYVPSVADI

LQIGWWATAAAWSILQQFLLSLTFPRLLEAVEMEDDDFTASLSKQSCITEQTQYFFDNDSK

SFSGVLDCGNCSRIFHGEKLMNTNLIFIMVESKGTCPCDTRLLIQAEQTSDGPNPCDMVK

17 - human amino acid sequence alpha2 delta-1

MAAGCLLALTLTLFQSLLIGPSSEEPFPSAVTIKSWVDKMQEDLVTLAKTASGVNQLVDIY

EKYQDLYTVEPNNARQLVEIAARDIEKLLSNRSKALVSLALEAEKVQAAHQWREDFASNEV

VYYNAKDDLDPEKNDSEPGSQRIKPVFIEDANFGRQISYQHAAVHIPTDIYEGSTIVLNEL

NWTSALDEVFKKNREEDPSLLWQVFGSATGLARYYPASPWVDNSRTPNKIDLYDVRRRPWY

IQGAASPKDMLILVDVSGSVSGLTLKLIRTSVSEMLETLSDDDFVNVASFNSNAQDVSCFQ

HLVQANVRNKKVLKDAVNNITAKGITDYKKGFSFAFEQLLNYNVSRANCNKIIMLFTDGGE

ERAQEIFNKYNKDKKVRVFRFSVGQHNYERGPIQWMACENKGYYYEIPSIGAIRINTQEYL

DVLGRPMVLAGDKAKQVQWTNVYLDALELGLVITGTLPVFNITGQFENKTNLKNQLILGVM

GVDVSLEDIKRLTPRFTLCPNGYYFAIDPNGYVLLHPNLQPKNPKSQEPVTLDFLDAELEN

DIKVEIRNKMIDGESGEKTFRTLVKSQDERYIDKGNRTYTWTPVNGTDYSLALVLPTYSFY

YIKAKLEETITQARSKKGKMKDSETLKPDNFEESGYTFIAPRDYCNDLKISDNNTEFLLNF

NEFIDRKTPNNPSCNADLINRVLLDAGFTNELVQNYWSKQKNIKGVKARFVVTDGGITRVY

PKEAGENWQENPETYEDSFYKRSLDNDNYVFTAPYFNKSGPGAYESGIMVSKAVEIYIQGK

LLKPAVVGIKIDVNSWIENFTKTSIRDPCAGPVCDCKRNSDVMDCVILDDGGFLLMANHDD

YTNQIGRFFGEIDPSLMRHLVNISVYAFNKSYDYQSVCEPGAAPKQGAGHRSAYVPSVADI

LQIGWWATAAAWSILQQFLLSLTFPRLLEAVEMEDDDFTASLSKQSCITEQTQYFFDNDSK

SEQUENCE LISTING

SFSGVLDCGNCSRIFHGEKLMNTNLIFIMVESKGTCPCDTRLLIQAEQTSDGPNPCDMVKQ

PRYRKGPDVCFDNNVLEDYTDCGGVS

18 - human nucleic acid sequence alpha2 delta-1

GCGGGGAGGGGCATTGATCTTCGATCGCGAAGATGGCTGCTGGCTGCCTGCTGGCCTTG

ACTCTGACACTTTTCCAATCTTTGCTCATCGGCCCCTCGTCGGAGGAGCCGTTCCCTTCGG

CCGTCACTATCAAATCATGGGTGGATAAGATGCAAGAAGACCTTGTCACACTGGCAAAAAC

AGCAAGTGGAGTCAATCAGCTTGTTGATATTTATGAGAAATATCAAGATTTGTATACTGTG

GAACCAAATAATGCACGCCAGCTGGTAGAAATTGCAGCCAGGGATATTGAGAAACTTCTGA

GCAACAGATCTAAAGCCCTGGTGAGCCTGGCATTGGAAGCGGAGAAAGTTCAAGCAGCTCA

CCAGTGGAGAGAAGATTTTGCAAGCAATGAAGTTGTCTACTACAATGCAAAGGATGATCTC

GATCCTGAGAAAAATGACAGTGAGCCAGGCAGCCAGAGGATAAAACCTGTTTTCATTGAAG

ATGCTAATTTTGGACGACAAATATCTTATCAGCACGCAGCAGTCCATATTCCTACTGACAT

CTATGAGGGCTCAACAATTGTGTTAAATGAACTCAACTGGACAAGTGCCTTAGATGAAGTT

TTCAAAAAGAATCGCGAGGAAGACCCCTTCATTATTGTGGCAGGTTTTTGGCAGTGCCACTG

GCCTAGCTCGATATTATCCAGCTTCACCATGGGTTGATAATAGTAGAACTCCAAATAAGAT

TGACCTTTATGATGTACGCAGAAGACCATGGTACATCCAAGGAGCTGCATCTCCTAAAGAC

ATGCTTATTCTGGTGGATGTGAGTGGAAGTGTTAGTGGATTGACACTTAAACTGATCCGAA

CATCTGTCTCCGAAATGTTAGAAACCCTCTCAGATGATGATTTCGTGAATGTAGCTTCATT

TAACAGCAATGCTCAGGATGTAAGCTGTTTTCAGCACCTTGTCCAAGCAAATGTAAGAAAT

AAAAAGTGTTGAAAGACGCGGTGAATAATATCACAGCCAAAGGAATTACAGATTATAAGA

AGGGCTTTAGTTTTGCTTTTGAACAGCTGCTTAATTATAATGTTTCCAGAGCAAACTGCAA

TAAGATTATTATGCTATTCACGGATGGAGGAGAAGAGAGAGCCCAGGAGATATTTAACAAA

TACAATAAAGATAAAAAAGTACGTGTATTCAGGTTTTCAGTTGGTCAACACAATTATGAGA

GAGGACCTATTCAGTGGATGGCCTGTGAAAACAAAGGTTATTATTATGAAATTCCTTCCAT

TGGTGCAATAAGAATCAATACTCAGGAATATTTGGATGTTTTGGGAAGACCAATGGTTTTA

GCAGGAGACAAAGCTAAGCAAGTCCAATGGACAAATGTGTACCTGGATGCATTGGAACTGG

GACTTGTCATTACTGGAACTCTTCCGGTCTTCAACATAACCGGCCAATTTGAAAATAAGAC

AAACTTAAAGAACCAGCTGATTCTTGGTGTGATGGGAGTAGATGTGTCTTTGGAAGATATT

AAAAGACTGACACCACGTTTTACACTGTGCCCCAATGGGTATTACTTTGCAATCGATCCTA

ATGGTTATGTTTTATTACATCCAAATCTTCAGCCAAAGAACCCCAAATCTCAGGAGCCAGT

AACATTGGATTTCCTTGATGCAGAGTTAGAGAATGATATTAAAGTGGAGATTCGAAATAAG

ATGATTGATGGGAAAGTGGAGAAAAAACATTCAGAACTCTGGTTAAATCTCAAGATGAGA

GATATATTGACAAAGGAAACAGGACATACACATGGACACCTGTCAATGGCACAGATTACAG

TTTGGCCTTGGTATTACCAACCTACAGTTTTTACTATATAAAAGCCAAACTAGAAGAGACA

ATAACTCAGGCCAGATCAAAAAAGGGCAAAATGAAGGATTCGGAAACCCTGAAGCCAGATA

ATTTTGAAGAATCTGGCTATACATTCATAGCACCAAGAGATTACTGCAATGACCTGAAAAT

ATCGGATAATAACACTGAATTTCTTTTAAATTTCAACGAGTTTATTGATAGAAAAACTCCA

AACAACCCATCATGTAACGCGGATTTGATTAATAGAGTCTTGCTTGATGCAGGCTTTACAA

ATGAACTTGTCCAAAATTACTGGAGTAAGCAGAAAAATATCAAGGGAGTGAAAGCACGATT
TGTTGTGACTGATGGTGGGATTACCAGAGTTTATCCCAAAGAGGCTGGAGAAAATTGGCAA
GAAAACCCAGAGACATATGAGGACAGCTTCTATAAAAGGAGCCTAGATAATGATAACTATG
TTTTCACTGCTCCCTACTTTAACAAAAGTGGACCTGGTGCCTATGAATCGGGCATTATGGT
AAGCAAAGCTGTAGAAATATATATTCAAGGGAAACTTCTTAAACCTGCAGTTGTTGGAATT
AAAATTGATGTAAATTCCTGGATAGAGAATTTCACCAAAACCTCAATCAGAGATCCGTGTG
CTGGTCCAGTTTGTGACTGCAAAAGAAACAGTGACGTAATGGATTGTGTGATTCTGGATGA
TGGTGGGTTTCTTCTGATGGCAAATCATGATGATTATACTAATCAGATTGGAAGATTTTTT
GGAGAGATTGATCCCAGCTTGATGAGACACCTGGTTAATATATCAGTTTATGCTTTTAACA
AATCTTATGATTATCAGTCAGTATGTGAGCCCGGTGCTGCACCAAAACAAGGAGCAGGACA
TCGCTCAGCATATGTGCCATCAGTAGCAGACATATTACAAATTGGCTGGTGGGCCACTGCT
GCTGCCTGGTCTATTCTACAGCAGTTTCTCTTGAGTTTGACCTTTCCACGACTCCTTGAGG
CAGTTGAGATGGAGGATGATGACTTCACGGCCTCCCTGTCCAAGCAGAGCTGCATTACTGA
ACAAACCCAGTATTTCTTCGATAACGACAGTAAATCATTCAGTGGTGTATTAGACTGTGGA
AACTGTTCCAGAATCTTTCATGGAGAAAAGCTTATGAACACCAACTTAATATTCATAATGG
TTGAGAGCAAAGGGACATGTCCATGTGACACACGACTGCTCATACAAGCGGAGCAGACTTC
TGACGGTCCAAATCCTTGTGACATGGTTAAGCAACCTAGATACCGAAAAGGGCCTGATGTC
TGCTTTGATAACAATGTCTTGGAGGATTATACTGACTGTGGTGGTGTTTCTGGATTAAATC
CCTCCCTGTGGTATATCATTGGAATCCAGTTTCTACTACTTTGGCTGGTATCTGGCAGCAC
ACACCGGCTGTTATGACCTTCTAAAAACCAAATCTGCATAGTTAAACTCCAGACCCTGCCA
AAACATGAGCCCTGCCCTCAATTACAGTAACGTAGGGTCAGCTATAAAATCAGACAAACAT
TAGCTGGGCCTGTTCCATGGCATAACACTAAGGCGCAGACTCCTAAGGCACCCACTGGCTG
CATGTCAGGGTGTCAGATCCTTAAACGTGTGTGAATGCTGCATCATCTATGTGTAACATCA
AAGCAAAATCCTATACGTGTCCTCTATTGGAAAATTTGGGCGTTTGTTGTTGCATTGTTGG
T

19 - human amino acid sequence alpha2 delta-1

ATGGCTGCTGGCTGCCTGCTGGCCTTGACTCTGACACTTTTCCAATCTTTGCTCATCGGCC
CCTCGTCGGAGGAGCCGTTCCCTTCGGCCGTCACTATCAAATCATGGGTGGATAAGATGCA
AGAAGACCTTGTCACACTGGCAAAAACAGCAAGTGGAGTCAATCAGCTTGTTGATATTTAT
GAGAAATATCAAGATTTGTATACTGTGGAACCAAATAATGCACGCCAGCTGGTAGAAATTG
CAGCCAGGGATATTGAGAAACTTCTGAGCAACAGATCTAAAGCCCTGGTGAGCCTGGCATT
GGAAGCGGAGAAAGTTCAAGCAGCTCACCAGTGGAGAGAAGATTTTGCAAGCAATGAAGTT
GTCTACTACAATGCAAAGGATGATCTCGATCCTGAGAAAAATGACAGTGAGCCAGGCAGCC
AGAGGATAAAACCTGTTTTCATTGAAGATGCTAATTTTGGACGACAAATATCTTATCAGCA
CGCAGCAGTCCATATTCCTACTGACATCTATGAGGGCTCAACAATTGTGTTAAATGAACTC
AACTGGACAAGTGCCTTAGATGAAGTTTTCAAAAAGAATCGCGAGGAAGACCCTTCATTAT
TGTGGCAGGTTTTTGGCAGTGCCACTGGCCTAGCTCGATATTATCCAGCTTCACCATGGGT
TGATAATAGTAGAACTCCAAATAAGATTGACCTTTATGATGTACGCAGAAGACCATGGTAC
ATCCAAGGAGCTGCATCTCCTAAAGACATGCTTATTCTGGTGGATGTGAGTGGAAGTGTTA

-continued

SEQUENCE LISTING

```
GTGGATTGACACTTAAACTGATCCGAACATCTGTCTCCGAAATGTTAGAAACCCTCTCAGA

TGATGATTTCGTGAATGTAGCTTCATTTAACAGCAATGCTCAGGATGTAAGCTGTTTTCAG

CACCTTGTCCAAGCAAATGTAAGAAATAAAAAAGTGTTGAAAGACGCGGTGAATAATATCA

CAGCCAAAGGAATTACAGATTATAAGAAGGGCTTTAGTTTTGCTTTTGAACAGCTGCTTAA

TTATAATGTTTCCAGAGCAAACTGCAATAAGATTATTATGCTATTCACGGATGGAGGAGAA

GAGAGAGCCCAGGAGATATTTAACAAATACAATAAAGATAAAAAAGTACGTGTATTCAGGT

TTTCAGTTGGTCAACACAATTATGAGAGAGGACCTATTCAGTGGATGGCCTGTGAAAACAA

AGGTTATTATTATGAAATTCCTTCCATTGGTGCAATAAGAATCAATACTCAGGAATATTTG

GATGTTTTGGGAAGACCAATGGTTTTAGCAGGAGACAAAGCTAAGCAAGTCCAATGGACAA

ATGTGTACCTGGATGCATTGGAACTGGGACTTGTCATTACTGGAACTCTTCCGGTCTTCAA

CATAACCGGCCAATTTGAAAATAAGACAAACTTAAAGAACCAGCTGATTCTTGGTGTGATG

GGAGTAGATGTGTCTTTGGAAGATATTAAAAGACTGACACCACGTTTTACACTGTGCCCCA

ATGGGTATTACTTTGCAATCGATCCTAATGGTTATGTTTTATTACATCCAAATCTTCAGCC

AAAGAACCCCAAATCTCAGGAGCCAGTAACATTGGATTTCCTTGATGCAGAGTTAGAGAAT

GATATTAAAGTGGAGATTCGAAATAAGATGATTGATGGGAAAGTGGAGAAAAAACATTCA

GAACTCTGGTTAAATCTCAAGATGAGAGATATATTGACAAAGGAAACAGGACATACACATG

GACACCTGTCAATGGCACAGATTACAGTTTGGCCTTGGTATTACCAACCTACAGTTTTTAC

TATATAAAAGCCAAACTAGAAGAGACAATAACTCAGGCCAGATCAAAAAAGGGCAAAATGA

AGGATTCGGAAACCCTGAAGCCAGATAATTTTGAAGAATCTGGCTATACATTCATAGCACC

AAGAGATTACTGCAATGACCTGAAAATATCGGATAATAACACTGAATTTCTTTTAAATTTC

AACGAGTTTATTGATAGAAAAACTCCAAACAACCCATCATGTAACGCGGATTTGATTAATA

GAGTCTTGCTTGATGCAGGCTTTACAAATGAACTTGTCCAAAATTACTGGAGTAAGCAGAA

AAATATCAAGGGAGTGAAAGCACGATTTGTTGTGACTGATGGTGGGATTACCATAGTTTAT

CCCAAAGAGGCTGGAGAAAATTGGCAAGAAACCCAGAGACATATGAGGACAGCTTCTATA

AAAGGAGCCTAGATAATGATAACTATGTTTTCACTGCTCCCTACTTTAACAAAAGTGGACC

TGGTGCCTATGAATCGGGCATTATGGTAAGCAAAGCTGTAGAAATATATATTCAAGGGAAA

CTTCTTAAACCTGCAGTTGTTGGAATTAAAATTGATGTAAATTCCTGGATAGAGAATTTCA

CCAAAACCTCAATCAGAGATCCGTGTGCTGGTCCAGTTTGTGACTGCAAAAGAAACAGTGA

CGTAATGGATTGTGTGATTCTGGATGATGGTGGGTTTCTTCTGATGGCAAATCATGATGAT

TATACTAATCAGATTGGAAGATTTTTTGGAGAGATTGATCCCAGCTTGATGAGACACCTGG

TTAATATATCAGTTTATGCTTTTAACAAATCTTATGATTATCAGTCAGTATGTGAGCCCGG

TGCTGCACCAAAACAAGGAGCAGGACATCGCTCAGCATATGTGCCATCAGTAGCAGACATA

TTACAAATTGGCTGGTGGGCCACTGCTGCTGCCTGGTCTATTCTACAGCAGTTTCTCTTGA

GTTTGACCTTTCCACGACTCCTTGAGGCAGTTGAGATGGAGGATGATGACTTCACGGCCTC

CCTGTCCAAGCAGAGCTGCATTACTGAACAAACCCAGTATTTCTTCGATAACGACAGTAAA

TCATTCAGTGGTGTATTAGACTGTGGAAACTGTTCCAGAATCTTTCATGGAGAAAAGCTTA

TGAACACCAACTTAATATTCATAATGGTTGAGAGCAAAGGGACATGTCCATGTGACACACG

ACTGC
```

-continued

SEQUENCE LISTING

20 - human amino acid sequence alpha2 delta-1

ATGGCTGCTGGCTGCCTGCTGGCCTTGACTCTGACACTTTTCCAATCTTTGCTCATCGGCC

CCTCGTCGGAGGAGCCGTTCCCTTCGGCCGTCACTATCAAATCATGGGTGGATAAGATGCA

AGAAGACCTTGTCACACTGGCAAAAACAGCAAGTGGAGTCAATCAGCTTGTTGATATTTAT

GAGAAATATCAAGATTTGTATACTGTGGAACCAAATAATGCACGCCAGCTGGTAGAAATTG

CAGCCAGGGATATTGAGAAACTTCTGAGCAACAGATCTAAAGCCCTGGTGAGCCTGGCATT

GGAAGCGGAGAAAGTTCAAGCAGCTCACCAGTGGAGAGAAGATTTTGCAAGCAATGAAGTT

GTCTACTACAATGCAAAGGATGATCTCGATCCTGAGAAAAATGACAGTGAGCCAGGCAGCC

AGAGGATAAAACCTGTTTTCATTGAAGATGCTAATTTTGGACGACAAATATCTTATCAGCA

CGCAGCAGTCCATATTCCTACTGACATCTATGAGGGCTCAACAATTGTGTTAAATGAACTC

AACTGGACAAGTGCCTTAGATGAAGTTTTCAAAAAGAATCGCGAGGAAGACCCTTCATTAT

TGTGGCAGGTTTTTGGCAGTGCCACTGGCCTAGCTCGATATTATCCAGCTTCACCATGGGT

TGATAATAGTAGAACTCCAAATAAGATTGACCTTTATGATGTACGCAGAAGACCATGGTAC

ATCCAAGGAGCTGCATCTCCTAAAGACATGCTTATTCTGGTGGATGTGAGTGGAAGTGTTA

GTGGATTGACACTTAAACTGATCCGAACATCTGTCTCCGAAATGTTAGAAACCCTCTCAGA

TGATGATTTCGTGAATGTAGCTTCATTTAACAGCAATGCTCAGGATGTAAGCTGTTTTCAG

CACCTTGTCCAAGCAAATGTAAGAAATAAAAAAGTGTTGAAAGACGCGGTGAATAATATCA

CAGCCAAAGGAATTACAGATTATAAGAAGGGCTTTAGTTTTGCTTTTGAACAGCTGCTTAA

TTATAATGTTTCCAGAGCAAACTGCAATAAGATTATTATGCTATTCACGGATGGAGGAGAA

GAGAGAGCCCAGGAGATATTTAACAAATACAATAAAGATAAAAAAGTACGTGTATTCAGGT

TTTCAGTTGGTCAACACAATTATGAGAGAGGACCTATTCAGTGGATGGCCTGTGAAAACAA

AGGTTATTATTATGAAATTCCTTCCATTGGTGCAATAAGAATCAATACTCAGGAATATTTG

GATGTTTTGGGAAGACCAATGGTTTTAGCAGGAGACAAAGCTAAGCAAGTCCAATGGACAA

ATGTGTACCTGGATGCATTGGAACTGGGACTTGTCATTACTGGAACTCTTCCGGTCTTCAA

CATAACCGGCCAATTTGAAAATAAGACAAACTTAAAGAACCAGCTGATTCTTGGTGTGATG

GGAGTAGATGTGTCTTTGGAAGATATTAAAAGACTGACACCACGTTTTACACTGTGCCCCA

ATGGGTATTACTTTGCAATCGATCCTAATGGTTATGTTTTATTACATCCAAATCTTCAGCC

AAAGAACCCCAAATCTCAGGAGCCAGTAACATTGGATTTCCTTGATGCAGAGTTAGAGAAT

GATATTAAAGTGGAGATTCGAAATAAGATGATTGATGGGGAAAGTGGAGAAAAAACATTCA

GAACTCTGGTTAAATCTCAAGATGAGAGATATATTGACAAAGGAAACAGGACATACACATG

GACACCTGTCAATGGCACAGATTACAGTTTGGCCTTGGTATTACCAACCTACAGTTTTTAC

TATATAAAAGCCAAACTAGAAGAGACAATAACTCAGGCCAGATCAAAAAAGGGCAAAATGA

AGGATTCGGAAACCCTGAAGCCAGATAATTTTGAAGAATCTGGCTATACATTCATAGCACC

AAGAGATTACTGCAATGACCTGAAAATATCGGATAATAACACTGAATTTCTTTTAAATTTC

AACGAGTTTATTGATAGAAAAACTCCAAACAACCCATCATGTAACGCGGATTTGATTAATA

GAGTCTTGCTTGATGCAGGCTTTACAAATGAACTTGTCCAAAATTACTGGAGTAAGCAGAA

AAATATCAAGGGAGTGAAAGCACGATTTGTTGTGACTGATGGTGGGATTACCAGAGTTTAT

CCCAAAGAGGCTGGAGAAAATTGGCAAGAAAACCCAGAGACATATGAGGACAGCTTCTATA

AAAGGAGCCTAGATAATGATAACTATGTTTTCACTGCTCCCTACTTTAACAAAAGTGGACC

```
TGGTGCCTATGAATCGGGCATTATGGTAAGCAAAGCTGTAGAAATATATATTCAAGGGAAA

CTTCTTAAACCTGCAGTTGTTGGAATTAAAATTGATGTAAATTCCTGGATAGAGAATTTCA

CCAAAACCTCAATCAGAGATCCGTGTGCTGGTCCAGTTTGTGACTGCAAAAGAAACAGTGA

CGTAATGGATTGTGTGATTCTGGATGATGGTGGGTTTCTTCTGATGGCAAATCATGATGAT

TATACTAATCAGATTGGAAGATTTTTTGGAGAGATTGATCCCAGCTTGATGAGACACCTGG

TTAATATATCAGTTTATGCTTTTAACAAATCTTATGATTATCAGTCAGTATGTGAGCCCGG

TGCTGCACCAAAACAAGGAGCAGGACATCGCTCAGCATATGTGCCATCAGTAGCAGACATA

TTACAAATTGGCTGGTGGGCCACTGCTGCTGCCTGGTCTATTCTACAGCAGTTTCTCTTGA

GTTTGACCTTTCCACGACTCCTTGAGGCAGTTGAGATGGAGGATGATGACTTCACGGCCTC

CCTGTCCAAGCAGAGCTGCATTACTGAACAAACCCAGTATTTCTTCGATAACGCACAGTAAA

TCATTCAGTGGTGTATTAGACTGTGGAAACTGTTCCAGAATCTTTCATGGAGAAAAGCTTA

TGAACACCAACTTAATATTCATAATGGTTGAGAGCAAAGGGACATGTCCATGTGACACACG

ACTGCTCATACAAGCGGAGCAGACTTCTGACGGTCCAAATCCTTGTGACATGGTTAAGC
```

21 - human nucleic acid sequence alpha2 delta-1

```
ATGGCTGCTGGCTGCCTGCTGGCCTTGACTCTGACACTTTTCCAATCTTTGCTCATCGGCC

CCTCGTCGGAGGAGCCGTTCCCTTCGGCCGTCACTATCAAATCATGGGTGGATAAGATGCA

AGAAGACCTTGTCACACTGGCAAAAACAGCAAGTGGAGTCAATCAGCTTGTTGATATTTAT

GAGAAATATCAAGATTTGTATACTGTGGAACCAAATAATGCACGCCAGCTGGTAGAAATTG

CAGCCAGGGATATTGAGAAACTTCTGAGCAACAGATCTAAAGCCCTGGTGAGCCTGGCATT

GGAAGCGGAGAAAGTTCAAGCAGCTCACCAGTGGAGAGAAGATTTTGCAAGCAATGAAGTT

GTCTACTACAATGCAAAGGATGATCTCGATCCTGAGAAAAATGACAGTGAGCCAGGCAGCC

AGAGGATAAAACCTGTTTTCATTGAAGATGCTAATTTTGGACGACAAATATCTTATCAGCA

CGCAGCAGTCCATATTCCTACTGACATCTATGAGGGCTCAACAATTGTGTTAAATGAACTC

AACTGGACAAGTGCCTTAGATGAAGTTTTCAAAAAGAATCGCGAGGAAGACCCTTCATTAT

TGTGGCAGGTTTTTGGCAGTGCCACTGGCCTAGCTCGATATTATCCAGCTTCACCATGGGT

TGATAATAGTAGAACTCCAAATAAGATTGACCTTTATGATGTACGCAGAAGACCATGGTAC

ATCCAAGGAGCTGCATCTCCTAAAGACATGCTTATTCTGGTGGATGTGAGTGGAAGTGTTA

GTGGATTGACACTTAAACTGATCCGAACATCTGTCTCCGAAATGTTAGAAACCCTCTCAGA

TGATGATTTCGTGAATGTAGCTTCATTTAACAGCAATGCTCAGGATGTAAGCTGTTTTCAG

CACCTTGTCCAAGCAAATGTAAGAAATAAAAAAGTGTTGAAAGACGCGGTGAATAATATCA

CAGCCAAAGGAATTACAGATTATAAGAAGGGCTTTAGTTTTGCTTTTGAACAGCTGCTTAA

TTATAATGTTTCCAGAGCAAACTGCAATAAGATTATTATGCTATTCACGGATGGAGGAGAA

GAGAGAGCCCAGGAGATATTTAACAAATACAATAAAGATAAAAAAGTACGTGTATTCAGGT

TTTCAGTTGGTCAACACAATTATGAGAGAGGACCTATTCAGTGGATGGCCTGTGAAAACAA

AGGTTATTATTATGAAATTCCTTCCATTGGTGCAATAAGAATCAATACTCAGGAATATTTG

GATGTTTTGGGAAGACCAATGGTTTTAGCAGGAGACAAAGCTAAGCAAGTCCAATGGACAA

ATGTGTACCTGGATGCATTGGAACTGGGACTTGTCATTACTGGAACTCTTCCGGTCTTCAA

CATAACCGGCCAATTTGAAAATAAGACAAACTTAAAGAACCAGCTGATTCTTGGTGTGATG
```

-continued

SEQUENCE LISTING

```
GGAGTAGATGTGTCTTTGGAAGATATTAAAAGACTGACACCACGTTTTACACTGTGCCCCA
ATGGGTATTACTTTGCAATCGATCCTAATGGTTATGTTTTATTACATCCAAATCTTCAGCC
AAAGAACCCCAAATCTCAGGAGCCAGTAACATTGGATTTCCTTGATGCAGAGTTAGAGAAT
GATATTAAAGTGGAGATTCGAAATAAGATGATTGATGGGGAAAGTGGAGAAAAAACATTCA
GAACTCTGGTTAAATCTCAAGATGAGAGATATATTGACAAAGGAAACAGGACATACACATG
GACACCTGTCAATGGCACAGATTACAGTTTGGCCTTGGTATTACCAACCTACAGTTTTTAC
TATATAAAAGCCAAACTAGAAGAGACAATAACTCAGGCCAGATCAAAAAAGGGCAAAATGA
AGGATTCGGAAACCCTGAAGCCAGATAATTTTGAAGAATCTGGCTATACATTCATAGCACC
AAGAGATTACTGCAATGACCTGAAAATATCGGATAATAACACTGAATTTCTTTTAAATTTC
AACGAGTTTATTGATAGAAAAACTCCAAACAACCCATCATGTAACGCGGATTTGATTAATA
GAGTCTTGCTTGATGCAGGCTTTACAAATGAACTTGTCCAAAATTACTGGAGTAAGCAGAA
AAATATCAAGGGAGTGAAAGCACGATTTGTTGTGACTGATGGTGGGATTACCAGAGTTTAT
CCCAAAGAGGCTGGAGAAAATTGGCAAGAAAACCCAGAGACATATGAGGACAGCTTCTATA
AAAGGAGCCTAGATAATGATAACTATGTTTTCACTGCTCCCTACTTTAACAAAGTGGACC
TGGTGCCTATGAATCGGGCATTATGGTAAGCAAAGCTGTAGAAATATATATTCAAGGGAAA
CTTCTTAAACCTGCAGTTGTTGGAATTAAAATTGATGTAAATTCCTGGATAGAGAATTTCA
CCAAAACCTCAATCAGAGATCCGTGTGCTGGTCCAGTTTGTGACTGCAAAAGAAACAGTGA
CGTAATGGATTGTGTGATTCTGGATGATGGTGGGTTTCTTCTGATGGCAAATCATGATGAT
TATACTAATCAGATTGGAAGATTTTTTGGAGAGATTGATCCCAGCTTGATGAGACACCTGG
TTAATATATCAGTTTATGCTTTTAACAAATCTTATGATTATCAGTCAGTATGTGAGCCCGG
TGCTGCACCAAAACAAGGAGCAGGACATCGCTCAGCATATGTGCCATCAGTAGCAGACATA
TTACAAATTGGCTGGTGGGCCACTGCTGCTGCCTGGTCTATTCTACAGCAGTTTCTCTTGA
GTTTGACCTTTCCACGACTCCTTGAGGCAGTTGAGATGGAGGATGATGACTTCACGGCCTC
CCTGTCCAAGCAGAGCTGCATTACTGAACAAACCCAGTATTTCTTCGATAACGACAGTAAA
TCATTCAGTGGTGTATTAGACTGTGGAAACTGTTCCAGAATCTTTCATGGAGAAAAGCTTA
TGAACACCAACTTAATATTCATAATGGTTGAGAGCAAAGGGACATGTCCATGTGACACACG
ACTGCTCATACAAGCGGAGCAGACTTCTGACGGTCCAAATCCTTGTGACATGGTTAAGCAA
CCTAGATACCGAAAAGGGCCTGATGTCTGCTTTGATAACAATGTCTTGGAGGATTATACTG
ACTGTGGTGGTGTTTCTG
```

22 - nucleotide sequence

```
GCAGATTTGGTTTTAGAAGGG
```

23 - nucleotide sequence

```
CAGAATTCCTCATCAAGAAACACCACCACAGTCGGT
```

24 - nucleotide sequence

```
TTCTCTAATTCTGCATCAAGG
```

-continued

SEQUENCE LISTING

25 - nucleotide sequence

TTTGGATGTAATAAAACATAG

26 - nucleotide sequence

CUACUACUACUAGGCCACGCGTCGACTAGTAC

What is claimed is:

1. A purified or isolated recombinant polypeptide consisting of a secreted soluble $\alpha_2\delta$-1 subunit polypeptide and a tag, wherein the amino acid sequence of said secreted soluble $\alpha_2\delta$-1 polypeptide consists of an amino acid sequence selected from the group consisting of SEQ ID NO:15; SEQ ID NO:16; and SEQ ID NO: 17.

2. A purified or isolated recombinant polypeptide consisting of a soluble secreted $\alpha_2\delta$-1 subunit polypeptide, wherein the amino acid sequence of said polypeptide consists of an amino acid sequence selected from the group consisting of SEQ ID NO:15; SEQ ID NO: 16; and SEQ ID NO: 17.

3. A purified or isolated recombinant polypeptide consisting of a soluble secreted $\alpha_2\delta$-1 subunit polypeptide, wherein the amino acid sequence of said polypeptide consists of an amino acid sequence set forth in SEQ ID NO:15.

4. A purified or isolated recombinant polypeptide consisting of a soluble secreted $\alpha_2\delta$-1 subunit polypeptide, wherein the amino acid sequence of said polypeptide consists of an amino acid sequence set forth in SEQ ID NO:16.

5. A purified or isolated recombinant polypeptide consisting of a soluble secreted $\alpha_2\delta$-1 subunit polypeptide, wherein the amino acid sequence of said polypeptide consists of amino acid sequence set forth in SEQ ID NO:17.

* * * * *

SEQUENCE LISTING

<160> NUMBER OF SEQ ID NOS: 25

<210> SEQ ID NO 1
<211> LENGTH: 3842
<212> TYPE: DNA
<213> ORGANISM: Sus scrofa

<400> SEQUENCE: 1

| | | | | | | |
|---|---|---|---|---|---|---|
| gggattgat | cttcgatcgc | gaagatggct | gctggctgcc | tgctggcctt | gactctgaca | 60 |
| cttttccaat | ctttgctgat | cggtccctca | tcgcaggagc | cgttcccgtc | ggccgtcact | 120 |
| atcaagtcat | gggtggataa | aatgcaagaa | gaccttgtca | ccctggcaaa | aacagcaagt | 180 |
| ggagtcaatc | agcttgtcga | tatttatgaa | aaataccaag | atttgtatac | tgtggaacca | 240 |
| aataatgcac | gccagctggt | ggaaattgca | gccagggata | ttgagaaact | tctgagcaac | 300 |
| agatctaaag | ccctggtgcg | cctagctttg | gaagcagaga | aggttcaagc | agcccaccag | 360 |
| tggagagagg | attttgcaag | caatgaagtt | gtctactaca | atgcaaagga | tgatctcgat | 420 |
| cctgaaaaaa | atgacagtga | gccaggcagc | cagaggataa | aacctgtttt | tattgatgat | 480 |
| gctaattttg | ggcgacagat | atcttatcag | catgcagcag | tccatattcc | caccgacatc | 540 |
| tatgagggct | caacaattgt | gttaaatgaa | ctgaactgga | caagtgcctt | agatgaagtt | 600 |
| ttcaagaaaa | atcgagagga | agatccctca | ttattgtggc | aggtgtttgg | cagtgccaca | 660 |
| ggcctggccc | ggtattatcc | agcttctcca | tgggttgata | acagtagaac | tccaaacaag | 720 |
| attgaccttt | atgatgtacg | aaggagacca | tggtacatcc | aaggagctgc | atctcctaaa | 780 |
| gatatgctta | ttctggtcga | cgtgagtgga | agtgttagtg | gtttgacgct | taaactgatc | 840 |
| cgaacatctg | tctctgaaat | gttggaaacc | ctctcagatg | acgattttgt | gaatgtagct | 900 |
| tcatttaaca | gcaatgccca | ggatgtaagc | tgttttcaac | accttgtcca | agcaaatgta | 960 |
| agaaataaga | aagtgctgaa | agatgcagtt | aataatatca | cagcaaaagg | aatcacagat | 1020 |
| tacaagaagg | gctttagttt | tgcttttgaa | caactgctta | attataacgt | ttctagagcc | 1080 |
| aactgcaata | agattatcat | gttgttcacc | gatggaggag | aagagagagc | tcaggagata | 1140 |
| tttgccaaat | acaacaaaga | caaaaaagta | cgtgtattca | cattttcagt | tggtcaacat | 1200 |
| aattatgaca | gaggacctat | tcagtggatg | gcctgtgaaa | ataaaggtta | ttattatgaa | 1260 |
| attccttcca | ttggagcaat | cagaatcaat | actcaggaat | atttggatgt | tctgggaaga | 1320 |
| ccaatggttt | tagcaggaga | caaagctaag | caagtccagt | ggacaaacgt | gtacctggat | 1380 |
| gcactggaac | tgggacttgt | cattactgga | actcttccgg | tcttcaacat | aaccggccaa | 1440 |
| aatgaaaata | agacgaactt | aaagaaccag | ctgattcttg | gtgtgatggg | agttgatgta | 1500 |
| tctttggaag | atattaaaag | actgacacca | cgttttacac | tgtgccccaa | tggctattac | 1560 |

```
tttgcaattg atcctaatgg ctatgtttta ttacatccaa atcttcagcc aaagaacccc   1620
aaatctcagg agccagtaac cttggatttc cttgatgcag aattagagaa tgatattaaa   1680
gtggagatcc gaaataaaat gatagatgga gaaagtggga aaaaaacatt cagaactctg   1740
gttaaatctc aagatgagag atatattgac aaaggaaaca ggacatatac atggactcct   1800
gtcaatggca cagattacag tttggccttg gtattaccaa cctacagttt ttactatata   1860
aaagccaaaa tagaagagac aataactcag gccagatcaa aaagggcaa atgaaggat    1920
tcagaaacac tgaagcctga taattttgaa gaatctggct atacattcat agcaccaaga   1980
gactactgca atgaccttaa aatatcagat aataataccg aatttctttt aaactttaat   2040
gagtttattg atagaaaaac tccaaacaac ccgtcatgca acacagattt gattaataga   2100
gtcttgctgg atgcgggctt tacaaatgaa cttgtccaaa attactggag taagcagaaa   2160
aacatcaagg gagtgaaagc acggtttgtt gtaactgatg gagggattac cagagtttat   2220
cccaaagagg ctggagaaaa ttggcaagaa acccagaaaa catatgagga cagcttctat   2280
aaaagaagtc tagataacga taactatgtt ttcactgctc cctactttaa caaaagtgga   2340
cctggtgctt atgaatcagg catcatggta agcaaagctg tagaaatata catccaagga   2400
aaacttctta aacctgcagt tgttggaatt aaaattgatg taaattcctg gatagagaat   2460
ttcaccaaaa catcaatcag ggatccgtgt gctggtccag tttgtgattg taaaagaaac   2520
agtgatgtaa tggattgtgt gattctagat gatggtgggt ttcttttgat ggcaaatcat   2580
gatgattata ctaaccagat tggaaggttt tttggagaga ttgacccaag tttgatgaga   2640
cacctggtta atatatcagt ttatgctttt aacaaatctt acgattatca gtcagtgtgt   2700
gagcctggtg ctgcaccaaa acaaggagca ggacatcgct cagcatatgt gccatcaata   2760
gcagacatct tacacattgg ctggtgggcc actgcagctg catggtctat tctacagcag   2820
tttctcttga gtttgacctt tccacgactt cttgaagcag ttgagatgga agatgatgac   2880
tttaccgcct ctctgtcaaa gcagagttgc attactgaac aaacccagta tttctttgat   2940
aatgatagca aatccttcag tggggtcttg gactgtggta actgttccag aatcttttcac  3000
gttgaaaaac ttatgaacac caacttaata ttcataatgg ttgagagcaa agggacttgt   3060
ccttgtgaca cacgattgct catacaagct gagcagactt ctgacggtcc agatccttgt   3120
gatatggtta agcaacccag ataccgaaaa gggcctgatg tctgttttga taacaatgcc   3180
ttggaggatt ataccgactg tggtggtgtt tctggattaa atccctccct gtggtccatc   3240
ttcggaatcc agtgtgttt actttggctt ttatctggca gcagacacta ccagttatga   3300
ccctctaaa accaaatctg catattaaac ttcagaccct gccagaatag gagccctcaa   3360
ttgcattaaa atagggtaaa ctgcagaatc agcagaactc tagctgggcc catcccatgg   3420
catcaatctc agactcataa ggcacccact ggctgcatgt cagggtgtca gatcctgaaa   3480
cttgtgtgaa tgctgcatca tctatgtata acatcagagc aaaattctat acctattcta   3540
ttggaaaatt tgagaatttg ttgttgcatt gttggtgatt acatgtaaaa gggctcccca   3600
cacagttgtg tatgaatcac gcaaattgtc ttgattttga cttgctgcaa tccttgtcct   3660
tttaccaaga aaatctctag agggaaaaaa aaagtctttt ttttccttca ctaattctgc   3720
tacaaattat ttcctgcttg gagtagttat tattaaaaaa tatatatata gagagagaga   3780
gagagaatta acattggtgt aatctgtcaa aatagaaata atggcttatt ttctacaaaa   3840
aa                                                                  3842
```

-continued

<210> SEQ ID NO 2
<211> LENGTH: 3057
<212> TYPE: DNA
<213> ORGANISM: Sus scrofa

<400> SEQUENCE: 2

| | | | | | |
|---|---|---|---|---|---|
| atggctgctg | gctgcctgct | ggccttgact | ctgacacttt | tccaatcttt | gctgatcggt | 60 |
| ccctcatcgc | aggagccgtt | cccgtcggcc | gtcactatca | agtcatgggt | ggataaaatg | 120 |
| caagaagacc | ttgtcaccct | ggcaaaaaca | gcaagtggag | tcaatcagct | tgtcgatatt | 180 |
| tatgaaaaat | accaagattt | gtatactgtg | aaccaaata | atgcacgcca | gctggtggaa | 240 |
| attgcagcca | gggatattga | gaaacttctg | agcaacagat | ctaaagccct | ggtgcgccta | 300 |
| gctttggaag | cagagaaggt | tcaagcagcc | caccagtgga | gagaggattt | tgcaagcaat | 360 |
| gaagttgtct | actacaatgc | aaaggatgat | ctcgatcctg | aaaaaaatga | cagtgagcca | 420 |
| ggcagccaga | ggataaaacc | tgttttttatt | gatgatgcta | attttgggcg | acagatatct | 480 |
| tatcagcatg | cagcagtcca | tattcccacc | gacatctatg | agggctcaac | aattgtgtta | 540 |
| aatgaactga | actggacaag | tgccttagat | gaagttttca | agaaaaatcg | agaggaagat | 600 |
| ccctcattat | tgtggcaggt | gtttggcagt | gccacaggcc | tggcccggta | ttatccagct | 660 |
| tctccatggg | ttgataacag | tagaactcca | acaagattg | acctttatga | tgtacgaagg | 720 |
| agaccatggt | acatccaagg | agctgcatct | cctaaagata | tgcttattct | ggtcgacgtg | 780 |
| agtggaagtg | ttagtggttt | gacgcttaaa | ctgatccgaa | catctgtctc | tgaaatgttg | 840 |
| gaaaccctct | cagatgacga | ttttgtgaat | gtagcttcat | ttaacagcaa | tgcccaggat | 900 |
| gtaagctgtt | tcaacaccct | tgtccaagca | aatgtaagaa | ataagaaagt | gctgaaagat | 960 |
| gcagttaata | atatcacagc | aaaaggaatc | acagattaca | agaagggctt | tagttttgct | 1020 |
| tttgaacaac | tgcttaatta | taacgttttct | agagccaact | gcaataagat | tatcatgttg | 1080 |
| ttcaccgatg | aggagaaga | gagagctcag | gagatatttg | ccaaatacaa | caaagacaaa | 1140 |
| aaagtacgtg | tattcacatt | ttcagttggt | caacataatt | atgacagagg | acctattcag | 1200 |
| tggatggcct | gtgaaaataa | aggttattat | tatgaaattc | cttccattgg | agcaatcaga | 1260 |
| atcaatactc | aggaatattt | ggatgttctg | ggaagaccaa | tggttttagc | aggagacaaa | 1320 |
| gctaagcaag | tccagtggac | aaacgtgtac | ctggatgcac | tggaactggg | acttgtcatt | 1380 |
| actggaactc | ttccggtctt | caacataacc | ggccaaaatg | aaaataagac | gaacttaaag | 1440 |
| aaccagctga | ttcttggtgt | gatgggagtt | gatgtatctt | tggaagatat | taaaagactg | 1500 |
| acaccacgtt | ttacactgtg | ccccaatggc | tattactttg | caattgatcc | taatggctat | 1560 |
| gttttattac | atccaaatct | tcagccaaag | aaccccaaat | ctcaggagcc | agtaaccttg | 1620 |
| gatttccttg | atgcagaatt | agagaatgat | attaaagtgg | agatccgaaa | taaaatgata | 1680 |
| gatggagaaa | gtggagaaaa | acattcaga | actctggtta | aatctcaaga | tgagagatat | 1740 |
| attgacaaag | gaaacaggac | atatacatgg | actcctgtca | atggcacaga | ttacagtttg | 1800 |
| gccttggtat | taccaaccta | cagttttttac | tatataaaag | ccaaaataga | agagacaata | 1860 |
| actcaggcca | gatcaaaaaa | gggcaaaatg | aaggattcag | aaacactgaa | gcctgataat | 1920 |
| tttgaagaat | ctggctatac | attcatagca | ccaagagact | actgcaatga | ccttaaaata | 1980 |
| tcagataata | ataccgaatt | tcttttaaac | tttaatgagt | ttattgatag | aaaaactcca | 2040 |
| aacaacccgt | catgcaacac | agatttgatt | aatagagtct | tgctggatgc | gggctttaca | 2100 |
| aatgaacttg | tccaaaatta | ctggagtaag | cagaaaaaca | tcaagggagt | gaaagcacgg | 2160 |

-continued

```
tttgttgtaa ctgatggagg gattaccaga gtttatccca aagaggctgg agaaaattgg      2220
caagaaaacc cagaaacata tgaggacagc ttctataaaa gaagtctaga taacgataac      2280
tatgttttca ctgctcccta ctttaacaaa agtggacctg gtgcttatga atcaggcatc      2340
atggtaagca aagctgtaga aatatacatc caaggaaaac ttcttaaacc tgcagttgtt      2400
ggaattaaaa ttgatgtaaa ttcctggata gagaatttca ccaaaacatc aatcagggat      2460
ccgtgtgctg gtccagtttg tgattgtaaa agaaacagtg atgtaatgga ttgtgtgatt      2520
ctagatgatg gtgggtttct tttgatggca aatcatgatg attatactaa ccagattgga      2580
aggttttttg gagagattga cccaagtttg atgagacacc tggttaatat atcagtttat      2640
gcttttaaca aatcttacga ttatcagtca gtgtgtgagc ctggtgctgc accaaaacaa      2700
ggagcaggac atcgctcagc atatgtgcca tcaatagcag acatcttaca cattggctgg      2760
tgggccactg cagctgcatg gtctattcta cagcagtttc tcttgagttt gacctttcca      2820
cgacttcttg aagcagttga gatggaagat gatgacttta ccgcctctct gtcaaagcag      2880
agttgcatta ctgaacaaac ccagtatttc tttgataatg atagcaaatc cttcagtggg      2940
gtcttggact gtggtaactg ttccagaatc tttcacgttg aaaaacttat gaacaccaac      3000
ttaatattca taatggttga gagcaaaggg acttgtcctt gtgacacacg attgtga        3057
```

<210> SEQ ID NO 3
<211> LENGTH: 3111
<212> TYPE: DNA
<213> ORGANISM: Sus scrofa

<400> SEQUENCE: 3

```
atggctgctg gctgcctgct ggccttgact ctgacacttt tccaatcttt gctgatcggt        60
ccctcatcgc aggagccgtt cccgtcggcc gtcactatca agtcatgggt ggataaaatg       120
caagaagacc ttgtcaccct ggcaaaaaca gcaagtggag tcaatcagct tgtcgatatt       180
tatgaaaaat accaagattt gtatactgtg gaaccaaata atgcacgcca gctggtggaa       240
attgcagcca gggatattga gaaacttctg agcaacagat ctaaagccct ggtgcgccta       300
gctttggaag cagagaaggt tcaagcagcc caccagtgga gagaggattt tgcaagcaat       360
gaagttgtct actacaatgc aaaggatgat ctcgatcctg aaaaaaatga cagtgagcca       420
ggcagccaga ggataaaacc tgttttatt gatgatgcta attttgggcg acagatatct       480
tatcagcatg cagcagtcca tattcccacc gacatctatg agggctcaac aattgtgtta       540
aatgaactga actggacaag tgccttagat gaagttttca agaaaaatcg agaggaagat       600
ccctcattat tgtggcaggt gtttggcagt gccacaggcc tggcccggta ttatccagct       660
tctccatggg ttgataacag tagaactcca acaagattg acctttatga tgtacgaagg       720
agaccatggt acatccaagg agctgcatct cctaaagata tgcttattct ggtcgacgtg       780
agtggaagtg ttagtggttt gacgcttaaa ctgatccgaa catctgtctc tgaaatgttg       840
gaaaccctct cagatgacga ttttgtgaat gtagcttcat ttaacagcaa tgcccaggat       900
gtaagctgtt tcaacaccct tgtccaagca aatgtaagaa ataagaaagt gctgaaagat       960
gcagttaata atatcacagc aaaaggaatc acagattaca agaagggctt tagtttttgct      1020 tttgaacaac tgcttaatta taacgtttct agagccaact gcaataagat tatcatgttg      1080
ttcaccgatg gaggagaaga gagagctcag gagatatttg ccaaatacaa caaagacaaa      1140
aaagtacgtg tattcacatt ttcagttggt caacataatt atgacagagg acctattcag      1200
```

```
tggatggcct gtgaaaataa aggttattat tatgaaattc cttccattgg agcaatcaga   1260
atcaatactc aggaatattt ggatgttctg ggaagaccaa tggttttagc aggagacaaa   1320
gctaagcaag tccagtggac aaacgtgtac ctggatgcac tggaactggg acttgtcatt   1380
actggaactc ttccggtctt caacataacc ggccaaaatg aaaataagac gaacttaaag   1440
aaccagctga ttcttggtgt gatgggagtt gatgtatctt tggaagatat taaaagactg   1500
acaccacgtt ttacactgtg ccccaatggc tattactttg caattgatcc taatggctat   1560
gttttattac atccaaatct tcagccaaag aaccccaaat ctcaggagcc agtaaccttg   1620
gatttccttg atgcagaatt agagaatgat attaaagtgg agatccgaaa taaaatgata   1680
gatggagaaa gtggagaaaa acattcaga actctggtta aatctcaaga tgagagatat   1740
attgacaaag gaaacaggac atatacatgg actcctgtca atggcacaga ttacagtttg   1800
gccttggtat taccaaccta cagttttac tatataaaag ccaaaataga agagacaata   1860
actcaggcca gatcaaaaaa gggcaaaatg aaggattcag aaacactgaa gcctgataat   1920
tttgaagaat ctggctatac attcatagca ccaagagact actgcaatga ccttaaaata   1980
tcagataata taccgaatt tcttttaaac tttaatgagt ttattgatag aaaaactcca   2040
aacaacccgt catgcaacac agatttgatt aatagagtct tgctggatgc gggctttaca   2100
aatgaacttg tccaaaatta ctggagtaag cagaaaaaca tcaagggagt gaaagcacgg   2160
tttgttgtaa ctgatggagg gattaccaga gtttatccca agaggctgg agaaaattgg   2220 caagaaaacc cagaaacata tgaggacagc ttctataaaa gaagtctaga taacgataac   2280
tatgttttca ctgctcccta ctttaacaaa agtggacctg gtgcttatga atcaggcatc   2340
atggtaagca aagctgtaga aatatacatc caaggaaaac ttcttaaacc tgcagttgtt   2400
ggaattaaaa ttgatgtaaa ttcctggata gagaatttca ccaaaacatc aatcagggat   2460
ccgtgtgctg gtccagtttg tgattgtaaa agaaacagtg atgtaatgga ttgtgtgatt   2520
ctagatgatg gtgggtttct tttgatggca aatcatgatg attatactaa ccagattgga   2580 aggtttttg gagagattga cccaagtttg atgagacacc tggttaatat atcagtttat   2640
gcttttaaca aatcttacga ttatcagtca gtgtgtgagc ctggtgctgc accaaaacaa   2700
ggagcaggac atcgctcagc atatgtgcca tcaatagcag acatcttaca cattggctgg   2760
tgggccactg cagctgcatg gtctattcta cagcagtttc tcttgagttt gacctttcca   2820
cgacttcttg aagcagttga gatggaagat gatgacttta ccgcctctct gtcaaagcag   2880
agttgcatta ctgaacaaac ccagtatttc tttgataatg atagcaaatc cttcagtggg   2940
gtcttggact gtggtaactg ttccagaatc tttcacgttg aaaaacttat gaacaccaac   3000
ttaatattca taatggttga gagcaaaggg acttgtcctt gtgacacacg attgctcata   3060
caagctgagc agacttctga cggtccagat ccttgtgata tggttaagtg a            3111
```

<210> SEQ ID NO 4
<211> LENGTH: 3192
<212> TYPE: DNA
<213> ORGANISM: Sus scrofa

<400> SEQUENCE: 4

```
atggctgctg gctgcctgct ggccttgact ctgacacttt tccaatcttt gctgatcggt     60
ccctcatcgc aggagccgtt cccgtcggcc gtcactatca agtcatgggt ggataaaatg    120
caagaagacc ttgtcaccct ggcaaaaaca gcaagtggag tcaatcagct tgtcgatatt    180
tatgaaaaat accaagattt gtatactgtg gaaccaaata atgcacgcca gctggtggaa    240
```

-continued

| | |
|---|---|
| attgcagcca gggatattga gaaacttctg agcaacagat ctaaagccct ggtgcgccta | 300 |
| gctttggaag cagagaaggt tcaagcagcc caccagtgga gagaggattt tgcaagcaat | 360 |
| gaagttgtct actacaatgc aaaggatgat ctcgatcctg aaaaaaatga cagtgagcca | 420 |
| ggcagccaga ggataaaacc tgttttatt gatgatgcta attttgggcg acagatatct | 480 |
| tatcagcatg cagcagtcca tattcccacc gacatctatg agggctcaac aattgtgtta | 540 |
| aatgaactga actggacaag tgccttagat gaagttttca gaaaaatcg agaggaagat | 600 |
| ccctcattat tgtggcaggt gtttggcagt gccacaggcc tgcccggta ttatccagct | 660 |
| tctccatggg ttgataacag tagaactcca acaagattg accttatga tgtacgaagg | 720 |
| agaccatggt acatccaagg agctgcatct cctaaagata tgcttattct ggtcgacgtg | 780 |
| agtggaagtg ttagtggttt gacgcttaaa ctgatccgaa catctgtctc tgaaatgttg | 840 |
| gaaaccctct cagatgacga ttttgtgaat gtagcttcat taacagcaa tgcccaggat | 900 |
| gtaagctgtt ttcaacacct tgtccaagca aatgtaagaa ataagaaagt gctgaaagat | 960 |
| gcagttaata atatcacagc aaaaggaatc acagattaca agaagggctt tagtttgct | 1020 |
| tttgaacaac tgcttaatta taacgtttct agagccaact gcaataagat tatcatgttg | 1080 |
| ttcaccgatg gaggagaaga gagagctcag gagatatttg ccaaatacaa caaagacaaa | 1140 |
| aaagtacgtg tattcacatt ttcagttggt caacataatt atgacagagg acctattcag | 1200 |
| tggatggcct gtgaaaataa aggttattat tatgaaattc cttccattgg agcaatcaga | 1260 |
| atcaatactc aggaatattt ggatgttctg gaagaccaa tggttttagc aggagacaaa | 1320 |
| gctaagcaag tccagtggac aaacgtgtac ctggatgcac tggaactggg acttgtcatt | 1380 |
| actggaactc ttccggtctt caacataacc ggccaaaatg aaaataagac gaacttaaag | 1440 |
| aaccagctga ttcttggtgt gatgggagtt gatgtatctt tggaagatat aaaagactg | 1500 |
| acaccacgtt ttacactgtg ccccaatggc tattactttg caattgatcc taatggctat | 1560 |
| gttttattac atccaaatct tcagccaaag aaccccaaat ctcaggagcc agtaaccttg | 1620 |
| gatttccttg atgcagaatt agagaatgat attaaagtgg agatccgaaa taaaatgata | 1680 |
| gatggagaaa gtggagaaaa aacattcaga actctggtta aatctcaaga tgagagatat | 1740 |
| attgacaaag gaaacaggac atatacatgg actcctgtca atggcacaga ttacagtttg | 1800 |
| gccttggtat taccaaccta cagttttttac tatataaaag ccaaaataga agagacaata | 1860 |
| actcaggcca gatcaaaaaa gggcaaaatg aaggattcag aaacactgaa gcctgataat | 1920 |
| tttgaagaat ctggctatac attcatagca ccaagagact actgcaatga ccttaaaata | 1980 |
| tcagataata taccgaatt tctttttaaac tttaatgagt ttattgatag aaaaactcca | 2040 |
| aacaacccgt catgcaacac agatttgatt aatagagtct tgctggatgc gggctttaca | 2100 |
| aatgaacttg tccaaaatta ctggagtaag cagaaaaaca tcaagggagt gaaagcacgg | 2160 |
| tttgttgtaa ctgatggagg gattaccaga gtttatccca agaggctgg agaaaattgg | 2220 |
| caagaaaacc cagaaacata tgaggacagc ttctataaaa gaagtctaga taacgataac | 2280 |
| tatgttttca ctgctcccta ctttaacaaa agtggacctg gtgcttatga atcaggcatc | 2340 |
| atggtaagca agctgtaga aatatacatc caaggaaaac ttcttaaacc tgcagttgtt | 2400 |
| ggaattaaaa ttgatgtaaa ttcctggata gagaatttca ccaaaacatc aatcagggat | 2460 |
| ccgtgtgctg gtccagtttg tgattgtaaa agaaacagtg atgtaatgga ttgtgtgatt | 2520 |
| ctagatgatg gtgggtttct tttgatggca aatcatgatg attatactaa ccagattgga | 2580 |

-continued

```
aggtttttg gagagattga cccaagtttg atgagacacc tggttaatat atcagtttat   2640
gcttttaaca aatcttacga ttatcagtca gtgtgtgagc ctggtgctgc accaaaacaa   2700
ggagcaggac atcgctcagc atatgtgcca tcaatagcag acatcttaca cattggctgg   2760
tgggccactg cagctgcatg gtctattcta cagcagtttc tcttgagttt gacctttcca   2820
cgacttcttg aagcagttga gatggaagat gatgacttta ccgcctctct gtcaaagcag   2880
agttgcatta ctgaacaaac ccagtatttc tttgataatg atagcaaatc cttcagtggg   2940
gtcttggact gtggtaactg ttccagaatc tttcacgttg aaaaacttat gaacaccaac   3000
ttaatattca taatggttga gagcaaaggg acttgtcctt gtgacacacg attgctcata   3060
caagctgagc agacttctga cggtccagat ccttgtgata tggttaagca acccagatac   3120
cgaaaagggc ctgatgtctg ttttgataac aatgccttgg aggattatac cgactgtggt   3180
ggtgtttctt ga                                                       3192
```

<210> SEQ ID NO 5
<211> LENGTH: 1091
<212> TYPE: PRT
<213> ORGANISM: Sus scrofa

<400> SEQUENCE: 5

```
Met Ala Ala Gly Cys Leu Leu Ala Leu Thr Leu Thr Leu Phe Gln Ser
  1               5                  10                  15

Leu Leu Ile Gly Pro Ser Ser Gln Glu Pro Phe Pro Ser Ala Val Thr
             20                  25                  30

Ile Lys Ser Trp Val Asp Lys Met Gln Glu Asp Leu Val Thr Leu Ala
         35                  40                  45

Lys Thr Ala Ser Gly Val Asn Gln Leu Val Asp Ile Tyr Glu Lys Tyr
     50                  55                  60

Gln Asp Leu Tyr Thr Val Glu Pro Asn Asn Ala Arg Gln Leu Val Glu
 65                  70                  75                  80

Ile Ala Ala Arg Asp Ile Glu Lys Leu Leu Ser Asn Arg Ser Lys Ala
                 85                  90                  95

Leu Val Arg Leu Ala Leu Glu Ala Glu Lys Val Gln Ala Ala His Gln
            100                 105                 110

Trp Arg Glu Asp Phe Ala Ser Asn Glu Val Val Tyr Tyr Asn Ala Lys
        115                 120                 125

Asp Asp Leu Asp Pro Glu Lys Asn Asp Ser Glu Pro Gly Ser Gln Arg
    130                 135                 140

Ile Lys Pro Val Phe Ile Asp Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
            180                 185                 190

Phe Lys Lys Asn Arg Glu Glu Asp Pro Ser Leu Leu Trp Gln Val Phe
        195                 200                 205

Gly Ser Ala Thr Gly Leu Ala Arg Tyr Tyr Pro Ala Ser Pro Trp Val
    210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
```

```
            260                 265                 270
Arg Thr Ser Val Ser Glu Met Leu Glu Thr Leu Ser Asp Asp Phe
    275                 280                 285
Val Asn Val Ala Ser Phe Asn Ser Asn Ala Gln Asp Val Ser Cys Phe
290                 295                 300
Gln His Leu Val Gln Ala Asn Val Arg Asn Lys Lys Val Leu Lys Asp
305                 310                 315                 320
Ala Val Asn Asn Ile Thr Ala Lys Gly Ile Thr Asp Tyr Lys Lys Gly
                325                 330                 335
Phe Ser Phe Ala Phe Glu Gln Leu Leu Asn Tyr Asn Val Ser Arg Ala
                340                 345                 350
Asn Cys Asn Lys Ile Ile Met Leu Phe Thr Asp Gly Gly Glu Glu Arg
                355                 360                 365
Ala Gln Glu Ile Phe Ala Lys Tyr Asn Lys Asp Lys Lys Val Arg Val
                370                 375                 380
Phe Thr Phe Ser Val Gly Gln His Asn Tyr Asp Arg Gly Pro Ile Gln
385                 390                 395                 400
Trp Met Ala Cys Glu Asn Lys Gly Tyr Tyr Tyr Glu Ile Pro Ser Ile
                405                 410                 415
Gly Ala Ile Arg Ile Asn Thr Gln Glu Tyr Leu Asp Val Leu Gly Arg
                420                 425                 430
Pro Met Val Leu Ala Gly Asp Lys Ala Lys Gln Val Gln Trp Thr Asn
                435                 440                 445
Val Tyr Leu Asp Ala Leu Glu Leu Gly Leu Val Ile Thr Gly Thr Leu
    450                 455                 460
Pro Val Phe Asn Ile Thr Gly Gln Asn Glu Asn Lys Thr Asn Leu Lys
465                 470                 475                 480
Asn Gln Leu Ile Leu Gly Val Met Gly Val Asp Val Ser Leu Glu Asp
                485                 490                 495
Ile Lys Arg Leu Thr Pro Arg Phe Thr Leu Cys Pro Asn Gly Tyr Tyr
                500                 505                 510
Phe Ala Ile Asp Pro Asn Gly Tyr Val Leu Leu His Pro Asn Leu Gln
                515                 520                 525
Pro Lys Asn Pro Lys Ser Gln Glu Pro Val Thr Leu Asp Phe Leu Asp
    530                 535                 540
Ala Glu Leu Glu Asn Asp Ile Lys Val Glu Ile Arg Asn Lys Met Ile
545                 550                 555                 560
Asp Gly Glu Ser Gly Lys Thr Phe Arg Thr Leu Val Lys Ser Gln
                565                 570                 575
Asp Glu Arg Tyr Ile Asp Lys Gly Asn Arg Thr Tyr Thr Trp Thr Pro
                580                 585                 590
Val Asn Gly Thr Asp Tyr Ser Leu Ala Leu Val Leu Pro Thr Tyr Ser
                595                 600                 605
Phe Tyr Tyr Ile Lys Ala Lys Ile Glu Glu Thr Ile Thr Gln Ala Arg
                610                 615                 620
Ser Lys Lys Gly Lys Met Lys Asp Ser Glu Thr Leu Lys Pro Asp Asn
625                 630                 635                 640
Phe Glu Glu Ser Gly Tyr Thr Phe Ile Ala Pro Arg Asp Tyr Cys Asn
                645                 650                 655
Asp Leu Lys Ile Ser Asp Asn Asn Thr Glu Phe Leu Leu Asn Phe Asn
                660                 665                 670
Glu Phe Ile Asp Arg Lys Thr Pro Asn Asn Pro Ser Cys Asn Thr Asp
                675                 680                 685
```

-continued

```
Leu Ile Asn Arg Val Leu Leu Asp Ala Gly Phe Thr Asn Glu Leu Val
    690             695                 700
Gln Asn Tyr Trp Ser Lys Gln Lys Asn Ile Lys Gly Val Lys Ala Arg
705             710                 715                 720
Phe Val Thr Asp Gly Gly Ile Thr Arg Val Tyr Pro Lys Glu Ala
            725                 730                 735
Gly Glu Asn Trp Gln Glu Asn Pro Glu Thr Tyr Glu Asp Ser Phe Tyr
            740                 745                 750
Lys Arg Ser Leu Asp Asn Asp Asn Tyr Val Phe Thr Ala Pro Tyr Phe
        755                 760                 765
Asn Lys Ser Gly Pro Gly Ala Tyr Glu Ser Gly Ile Met Val Ser Lys
    770                 775                 780
Ala Val Glu Ile Tyr Ile Gln Gly Lys Leu Leu Lys Pro Ala Val Val
785                 790                 795                 800
Gly Ile Lys Ile Asp Val Asn Ser Trp Ile Glu Asn Phe Thr Lys Thr
                805                 810                 815
Ser Ile Arg Asp Pro Cys Ala Gly Pro Val Cys Asp Cys Lys Arg Asn
            820                 825                 830
Ser Asp Val Met Asp Cys Val Ile Leu Asp Asp Gly Gly Phe Leu Leu
        835                 840                 845
Met Ala Asn His Asp Asp Tyr Thr Asn Gln Ile Gly Arg Phe Phe Gly
    850                 855                 860
Glu Ile Asp Pro Ser Leu Met Arg His Leu Val Asn Ile Ser Val Tyr
865                 870                 875                 880
Ala Phe Asn Lys Ser Tyr Asp Tyr Gln Ser Val Cys Glu Pro Gly Ala
                885                 890                 895
Ala Pro Lys Gln Gly Ala Gly His Arg Ser Ala Tyr Val Pro Ser Ile
            900                 905                 910
Ala Asp Ile Leu His Ile Gly Trp Trp Ala Thr Ala Ala Ala Trp Ser
        915                 920                 925
Ile Leu Gln Gln Phe Leu Leu Ser Leu Thr Phe Pro Arg Leu Leu Glu
    930                 935                 940
Ala Val Glu Met Glu Asp Asp Asp Phe Thr Ala Ser Leu Ser Lys Gln
945                 950                 955                 960
Ser Cys Ile Thr Glu Gln Thr Gln Tyr Phe Phe Asp Asn Asp Ser Lys
                965                 970                 975
Ser Phe Ser Gly Val Leu Asp Cys Gly Asn Cys Ser Arg Ile Phe His
            980                 985                 990
Val Glu Lys Leu Met Asn Thr Asn Leu Ile Phe Ile Met Val Glu Ser
        995                 1000                1005
Lys Gly Thr Cys Pro Cys Asp Thr Arg Leu Leu Ile Gln Ala Glu Gln
    1010                1015                1020
Thr Ser Asp Gly Pro Asp Pro Cys Asp Met Val Lys Gln Pro Arg Tyr
1025                1030                1035                1040
Arg Lys Gly Pro Asp Val Cys Phe Asp Asn Asn Ala Leu Glu Asp Tyr
                1045                1050                1055
Thr Asp Cys Gly Gly Val Ser Gly Leu Asn Pro Ser Leu Trp Ser Ile
            1060                1065                1070
Phe Gly Ile Gln Cys Val Leu Leu Trp Leu Leu Ser Gly Ser Arg His
        1075                1080                1085
Tyr Gln Leu
    1090
```

-continued

```
<210> SEQ ID NO 6
<211> LENGTH: 1018
<212> TYPE: PRT
<213> ORGANISM: Sus scrofa

<400> SEQUENCE: 6
```

| Met | Ala | Ala | Gly | Cys | Leu | Leu | Ala | Leu | Thr | Leu | Thr | Leu | Phe | Gln | Ser |
|---|---|---|---|---|---|---|---|---|---|---|---|---|---|---|---|
| 1 | | | | 5 | | | | | 10 | | | | | 15 | |

| Leu | Leu | Ile | Gly | Pro | Ser | Ser | Gln | Glu | Pro | Phe | Pro | Ser | Ala | Val | Thr |
|---|---|---|---|---|---|---|---|---|---|---|---|---|---|---|---|
| | | | 20 | | | | | 25 | | | | | 30 | | |

| Ile | Lys | Ser | Trp | Val | Asp | Lys | Met | Gln | Glu | Asp | Leu | Val | Thr | Leu | Ala |
|---|---|---|---|---|---|---|---|---|---|---|---|---|---|---|---|
| | | 35 | | | | | 40 | | | | | 45 | | | |

| Lys | Thr | Ala | Ser | Gly | Val | Asn | Gln | Leu | Val | Asp | Ile | Tyr | Glu | Lys | Tyr |
|---|---|---|---|---|---|---|---|---|---|---|---|---|---|---|---|
| | 50 | | | | | 55 | | | | | 60 | | | | |

| Gln | Asp | Leu | Tyr | Thr | Val | Glu | Pro | Asn | Asn | Ala | Arg | Gln | Leu | Val | Glu |
|---|---|---|---|---|---|---|---|---|---|---|---|---|---|---|---|
| 65 | | | | | 70 | | | | | 75 | | | | | 80 |

| Ile | Ala | Ala | Arg | Asp | Ile | Glu | Lys | Leu | Leu | Ser | Asn | Arg | Ser | Lys | Ala |
|---|---|---|---|---|---|---|---|---|---|---|---|---|---|---|---|
| | | | | 85 | | | | | 90 | | | | | 95 | |

| Leu | Val | Arg | Leu | Ala | Leu | Glu | Ala | Glu | Lys | Val | Gln | Ala | Ala | His | Gln |
|---|---|---|---|---|---|---|---|---|---|---|---|---|---|---|---|
| | | | 100 | | | | | 105 | | | | | 110 | | |

| Trp | Arg | Glu | Asp | Phe | Ala | Ser | Asn | Glu | Val | Val | Tyr | Tyr | Asn | Ala | Lys |
|---|---|---|---|---|---|---|---|---|---|---|---|---|---|---|---|
| | | 115 | | | | | 120 | | | | | 125 | | | |

| Asp | Asp | Leu | Asp | Pro | Glu | Lys | Asn | Asp | Ser | Glu | Pro | Gly | Ser | Gln | Arg |
|---|---|---|---|---|---|---|---|---|---|---|---|---|---|---|---|
| | 130 | | | | | 135 | | | | | 140 | | | | |

| Ile | Lys | Pro | Val | Phe | Ile | Asp | Asp | Ala | Asn | Phe | Gly | Arg | Gln | Ile | Ser |
|---|---|---|---|---|---|---|---|---|---|---|---|---|---|---|---|
| 145 | | | | | 150 | | | | | 155 | | | | | 160 |

| Tyr | Gln | His | Ala | Ala | Val | His | Ile | Pro | Thr | Asp | Ile | Tyr | Glu | Gly | Ser |
|---|---|---|---|---|---|---|---|---|---|---|---|---|---|---|---|
| | | | | 165 | | | | | 170 | | | | | 175 | |

| Thr | Ile | Val | Leu | Asn | Glu | Leu | Asn | Trp | Thr | Ser | Ala | Leu | Asp | Glu | Val |
|---|---|---|---|---|---|---|---|---|---|---|---|---|---|---|---|
| | | | 180 | | | | | 185 | | | | | 190 | | |

| Phe | Lys | Lys | Asn | Arg | Glu | Glu | Asp | Pro | Ser | Leu | Leu | Trp | Gln | Val | Phe |
|---|---|---|---|---|---|---|---|---|---|---|---|---|---|---|---|
| | | 195 | | | | | 200 | | | | | 205 | | | |

| Gly | Ser | Ala | Thr | Gly | Leu | Ala | Arg | Tyr | Tyr | Pro | Ala | Ser | Pro | Trp | Val |
|---|---|---|---|---|---|---|---|---|---|---|---|---|---|---|---|
| | 210 | | | | | 215 | | | | | 220 | | | | |

| Asp | Asn | Ser | Arg | Thr | Pro | Asn | Lys | Ile | Asp | Leu | Tyr | Asp | Val | Arg | Arg |
|---|---|---|---|---|---|---|---|---|---|---|---|---|---|---|---|
| 225 | | | | | 230 | | | | | 235 | | | | | 240 |

| Arg | Pro | Trp | Tyr | Ile | Gln | Gly | Ala | Ala | Ser | Pro | Lys | Asp | Met | Leu | Ile |
|---|---|---|---|---|---|---|---|---|---|---|---|---|---|---|---|
| | | | | 245 | | | | | 250 | | | | | 255 | |

| Leu | Val | Asp | Val | Ser | Gly | Ser | Val | Ser | Gly | Leu | Thr | Leu | Lys | Leu | Ile |
|---|---|---|---|---|---|---|---|---|---|---|---|---|---|---|---|
| | | | 260 | | | | | 265 | | | | | 270 | | |

| Arg | Thr | Ser | Val | Ser | Glu | Met | Leu | Glu | Thr | Leu | Ser | Asp | Asp | Asp | Phe |
|---|---|---|---|---|---|---|---|---|---|---|---|---|---|---|---|
| | | 275 | | | | | 280 | | | | | 285 | | | |

| Val | Asn | Val | Ala | Ser | Phe | Asn | Ser | Asn | Ala | Gln | Asp | Val | Ser | Cys | Phe |
|---|---|---|---|---|---|---|---|---|---|---|---|---|---|---|---|
| | 290 | | | | | 295 | | | | | 300 | | | | |

| Gln | His | Leu | Val | Gln | Ala | Asn | Val | Arg | Asn | Lys | Lys | Val | Leu | Lys | Asp |
|---|---|---|---|---|---|---|---|---|---|---|---|---|---|---|---|
| 305 | | | | | 310 | | | | | 315 | | | | | 320 |

| Ala | Val | Asn | Asn | Ile | Thr | Ala | Lys | Gly | Ile | Thr | Asp | Tyr | Lys | Lys | Gly |
|---|---|---|---|---|---|---|---|---|---|---|---|---|---|---|---|
| | | | | 325 | | | | | 330 | | | | | 335 | |

| Phe | Ser | Phe | Ala | Phe | Glu | Gln | Leu | Leu | Asn | Tyr | Asn | Val | Ser | Arg | Ala |
|---|---|---|---|---|---|---|---|---|---|---|---|---|---|---|---|
| | | | 340 | | | | | 345 | | | | | 350 | | |

| Asn | Cys | Asn | Lys | Ile | Ile | Met | Leu | Phe | Thr | Asp | Gly | Gly | Glu | Glu | Arg |
|---|---|---|---|---|---|---|---|---|---|---|---|---|---|---|---|
| | | 355 | | | | | 360 | | | | | 365 | | | |

| Ala | Gln | Glu | Ile | Phe | Ala | Lys | Tyr | Asn | Lys | Asp | Lys | Lys | Val | Arg | Val |
|---|---|---|---|---|---|---|---|---|---|---|---|---|---|---|---|
| | 370 | | | | | 375 | | | | | 380 | | | | |

-continued

```
Phe Thr Phe Ser Val Gly Gln His Asn Tyr Asp Arg Gly Pro Ile Gln
385                 390                 395                 400

Trp Met Ala Cys Glu Asn Lys Gly Tyr Tyr Glu Ile Pro Ser Ile
                405                 410                 415

Gly Ala Ile Arg Ile Asn Thr Gln Glu Tyr Leu Asp Val Leu Gly Arg
                420                 425                 430

Pro Met Val Leu Ala Gly Asp Lys Ala Lys Gln Val Gln Trp Thr Asn
            435                 440                 445

Val Tyr Leu Asp Ala Leu Glu Leu Gly Leu Val Ile Thr Gly Thr Leu
    450                 455                 460

Pro Val Phe Asn Ile Thr Gly Gln Asn Glu Asn Lys Thr Asn Leu Lys
465                 470                 475                 480

Asn Gln Leu Ile Leu Gly Val Met Gly Val Asp Val Ser Leu Glu Asp
                    485                 490                 495

Ile Lys Arg Leu Thr Pro Arg Phe Thr Leu Cys Pro Asn Gly Tyr Tyr
                500                 505                 510

Phe Ala Ile Asp Pro Asn Gly Tyr Val Leu Leu His Pro Asn Leu Gln
                515                 520                 525

Pro Lys Asn Pro Lys Ser Gln Glu Pro Val Thr Leu Asp Phe Leu Asp
            530                 535                 540

Ala Glu Leu Glu Asn Asp Ile Lys Val Glu Ile Arg Asn Lys Met Ile
545                 550                 555                 560

Asp Gly Glu Ser Gly Glu Lys Thr Phe Arg Thr Leu Val Lys Ser Gln
                565                 570                 575

Asp Glu Arg Tyr Ile Asp Lys Gly Asn Arg Thr Tyr Thr Trp Thr Pro
            580                 585                 590

Val Asn Gly Thr Asp Tyr Ser Leu Ala Leu Val Leu Pro Thr Tyr Ser
        595                 600                 605

Phe Tyr Tyr Ile Lys Ala Lys Ile Glu Thr Ile Thr Gln Ala Arg
            610                 615                 620

Ser Lys Lys Gly Lys Met Lys Asp Ser Glu Thr Leu Lys Pro Asp Asn
625                 630                 635                 640

Phe Glu Glu Ser Gly Tyr Thr Phe Ile Ala Pro Arg Asp Tyr Cys Asn
                645                 650                 655

Asp Leu Lys Ile Ser Asp Asn Asn Thr Glu Phe Leu Leu Asn Phe Asn
            660                 665                 670

Glu Phe Ile Asp Arg Lys Thr Pro Asn Asn Pro Ser Cys Asn Thr Asp
        675                 680                 685

Leu Ile Asn Arg Val Leu Leu Asp Ala Gly Phe Thr Asn Glu Leu Val
690                 695                 700

Gln Asn Tyr Trp Ser Lys Gln Lys Asn Ile Lys Gly Val Lys Ala Arg
705                 710                 715                 720

Phe Val Val Thr Asp Gly Gly Ile Thr Arg Val Tyr Pro Lys Glu Ala
                725                 730                 735

Gly Glu Asn Trp Gln Glu Asn Pro Glu Thr Tyr Glu Asp Ser Phe Tyr
            740                 745                 750

Lys Arg Ser Leu Asp Asn Asp Asn Tyr Val Phe Thr Ala Pro Tyr Phe
        755                 760                 765

Asn Lys Ser Gly Pro Gly Ala Tyr Glu Ser Gly Ile Met Val Ser Lys
        770                 775                 780

Ala Val Glu Ile Tyr Ile Gln Gly Lys Leu Leu Lys Pro Ala Val Val
785                 790                 795                 800
```

-continued

```
Gly Ile Lys Ile Asp Val Asn Ser Trp Ile Glu Asn Phe Thr Lys Thr
                805                 810                 815

Ser Ile Arg Asp Pro Cys Ala Gly Pro Val Cys Asp Cys Lys Arg Asn
            820                 825                 830

Ser Asp Val Met Asp Cys Val Ile Leu Asp Asp Gly Gly Phe Leu Leu
        835                 840                 845

Met Ala Asn His Asp Asp Tyr Thr Asn Gln Ile Gly Arg Phe Phe Gly
    850                 855                 860

Glu Ile Asp Pro Ser Leu Met Arg His Leu Val Asn Ile Ser Val Tyr
865                 870                 875                 880

Ala Phe Asn Lys Ser Tyr Asp Tyr Gln Ser Val Cys Glu Pro Gly Ala
                885                 890                 895

Ala Pro Lys Gln Gly Ala Gly His Arg Ser Ala Tyr Val Pro Ser Ile
            900                 905                 910

Ala Asp Ile Leu His Ile Gly Trp Trp Ala Thr Ala Ala Ala Trp Ser
        915                 920                 925

Ile Leu Gln Gln Phe Leu Leu Ser Leu Thr Phe Pro Arg Leu Leu Glu
    930                 935                 940

Ala Val Glu Met Glu Asp Asp Phe Thr Ala Ser Leu Ser Lys Gln
945                 950                 955                 960

Ser Cys Ile Thr Glu Gln Thr Gln Tyr Phe Phe Asp Asn Asp Ser Lys
                965                 970                 975

Ser Phe Ser Gly Val Leu Asp Cys Gly Asn Cys Ser Arg Ile Phe His
            980                 985                 990

Val Glu Lys Leu Met Asn Thr Asn Leu Ile Phe Ile Met Val Glu Ser
        995                 1000                1005

Lys Gly Thr Cys Pro Cys Asp Thr Arg Leu
    1010                1015
```

<210> SEQ ID NO 7
<211> LENGTH: 1036
<212> TYPE: PRT
<213> ORGANISM: Sus scrofa

<400> SEQUENCE: 7

```
Met Ala Ala Gly Cys Leu Leu Ala Leu Thr Leu Thr Leu Phe Gln Ser
1               5                   10                  15

Leu Leu Ile Gly Pro Ser Ser Gln Glu Pro Phe Pro Ser Ala Val Thr
            20                  25                  30

Ile Lys Ser Trp Val Asp Lys Met Gln Glu Asp Leu Val Thr Leu Ala
        35                  40                  45

Lys Thr Ala Ser Gly Val Asn Gln Leu Val Asp Ile Tyr Glu Lys Tyr
    50                  55                  60

Gln Asp Leu Tyr Thr Val Glu Pro Asn Asn Ala Arg Gln Leu Val Glu
65                  70                  75                  80

Ile Ala Ala Arg Asp Ile Glu Lys Leu Leu Ser Asn Arg Ser Lys Ala
                85                  90                  95

Leu Val Arg Leu Ala Leu Glu Ala Glu Lys Val Gln Ala Ala His Gln
            100                 105                 110

Trp Arg Glu Asp Phe Ala Ser Asn Glu Val Val Tyr Tyr Asn Ala Lys
        115                 120                 125

Asp Asp Leu Asp Pro Glu Lys Asn Asp Ser Glu Pro Gly Ser Gln Arg
    130                 135                 140

Ile Lys Pro Val Phe Ile Asp Asp Ala Asn Phe Gly Arg Gln Ile Ser
145                 150                 155                 160
```

```
Tyr Gln His Ala Ala Val His Ile Pro Thr Asp Ile Tyr Glu Gly Ser
                165                 170                 175
Thr Ile Val Leu Asn Glu Leu Asn Trp Thr Ser Ala Leu Asp Glu Val
                180                 185                 190
Phe Lys Lys Asn Arg Glu Glu Asp Pro Ser Leu Leu Trp Gln Val Phe
                195                 200                 205
Gly Ser Ala Thr Gly Leu Ala Arg Tyr Tyr Pro Ala Ser Pro Trp Val
        210                 215                 220
Asp Asn Ser Arg Thr Pro Asn Lys Ile Asp Leu Tyr Asp Val Arg Arg
225                 230                 235                 240
Arg Pro Trp Tyr Ile Gln Gly Ala Ala Ser Pro Lys Asp Met Leu Ile
                245                 250                 255
Leu Val Asp Val Ser Gly Ser Val Ser Gly Leu Thr Leu Lys Leu Ile
                260                 265                 270
Arg Thr Ser Val Ser Glu Met Leu Glu Thr Leu Ser Asp Asp Asp Phe
        275                 280                 285
Val Asn Val Ala Ser Phe Asn Ser Asn Ala Gln Asp Val Ser Cys Phe
        290                 295                 300
Gln His Leu Val Gln Ala Asn Val Arg Asn Lys Lys Val Leu Lys Asp
305                 310                 315                 320
Ala Val Asn Asn Ile Thr Ala Lys Gly Ile Thr Asp Tyr Lys Lys Gly
                325                 330                 335
Phe Ser Phe Ala Phe Glu Gln Leu Leu Asn Tyr Asn Val Ser Arg Ala
                340                 345                 350
Asn Cys Asn Lys Ile Ile Met Leu Phe Thr Asp Gly Gly Glu Glu Arg
        355                 360                 365
Ala Gln Glu Ile Phe Ala Lys Tyr Asn Lys Asp Lys Lys Val Arg Val
        370                 375                 380
Phe Thr Phe Ser Val Gly Gln His Asn Tyr Asp Arg Gly Pro Ile Gln
385                 390                 395                 400
Trp Met Ala Cys Glu Asn Lys Gly Tyr Tyr Tyr Glu Ile Pro Ser Ile
                405                 410                 415
Gly Ala Ile Arg Ile Asn Thr Gln Glu Tyr Leu Asp Val Leu Gly Arg
                420                 425                 430
Pro Met Val Leu Ala Gly Asp Lys Ala Lys Gln Val Gln Trp Thr Asn
        435                 440                 445
Val Tyr Leu Asp Ala Leu Glu Leu Gly Leu Val Ile Thr Gly Thr Leu
        450                 455                 460
Pro Val Phe Asn Ile Thr Gly Gln Asn Glu Asn Lys Thr Asn Leu Lys
465                 470                 475                 480
Asn Gln Leu Ile Leu Gly Val Met Gly Val Asp Val Ser Leu Glu Asp
                485                 490                 495
Ile Lys Arg Leu Thr Pro Arg Phe Thr Leu Cys Pro Asn Gly Tyr Tyr
                500                 505                 510
Phe Ala Ile Asp Pro Asn Gly Tyr Val Leu Leu His Pro Asn Leu Gln
        515                 520                 525
Pro Lys Asn Pro Lys Ser Gln Glu Pro Val Thr Leu Asp Phe Leu Asp
530                 535                 540
Ala Glu Leu Glu Asn Asp Ile Lys Val Glu Ile Arg Asn Lys Met Ile
545                 550                 555                 560
Asp Gly Glu Ser Gly Glu Lys Thr Phe Arg Thr Leu Val Lys Ser Gln
                565                 570                 575
```

```
Asp Glu Arg Tyr Ile Asp Lys Gly Asn Arg Thr Tyr Thr Trp Thr Pro
            580                 585                 590
Val Asn Gly Thr Asp Tyr Ser Leu Ala Leu Val Leu Pro Thr Tyr Ser
            595                 600                 605
Phe Tyr Tyr Ile Lys Ala Lys Ile Glu Thr Ile Thr Gln Ala Arg
    610                 615                 620
Ser Lys Lys Gly Lys Met Lys Asp Ser Glu Thr Leu Lys Pro Asp Asn
625                 630                 635                 640
Phe Glu Glu Ser Gly Tyr Thr Phe Ile Ala Pro Arg Asp Tyr Cys Asn
                645                 650                 655
Asp Leu Lys Ile Ser Asp Asn Asn Thr Glu Phe Leu Leu Asn Phe Asn
            660                 665                 670
Glu Phe Ile Asp Arg Lys Thr Pro Asn Asn Pro Ser Cys Asn Thr Asp
        675                 680                 685
Leu Ile Asn Arg Val Leu Leu Asp Ala Gly Phe Thr Asn Glu Leu Val
        690                 695                 700
Gln Asn Tyr Trp Ser Lys Gln Lys Asn Ile Lys Gly Val Lys Ala Arg
705                 710                 715                 720
Phe Val Val Thr Asp Gly Gly Ile Thr Arg Val Tyr Pro Lys Glu Ala
                725                 730                 735
Gly Glu Asn Trp Gln Glu Asn Pro Glu Thr Tyr Glu Asp Ser Phe Tyr
            740                 745                 750
Lys Arg Ser Leu Asp Asn Asp Asn Tyr Val Phe Thr Ala Pro Tyr Phe
        755                 760                 765
Asn Lys Ser Gly Pro Gly Ala Tyr Glu Ser Gly Ile Met Val Ser Lys
        770                 775                 780
Ala Val Glu Ile Tyr Ile Gln Gly Lys Leu Leu Lys Pro Ala Val Val
785                 790                 795                 800
Gly Ile Lys Ile Asp Val Asn Ser Trp Ile Glu Asn Phe Thr Lys Thr
                805                 810                 815
Ser Ile Arg Asp Pro Cys Ala Gly Pro Val Cys Asp Cys Lys Arg Asn
            820                 825                 830
Ser Asp Val Met Asp Cys Val Ile Leu Asp Asp Gly Gly Phe Leu Leu
            835                 840                 845
Met Ala Asn His Asp Asp Tyr Thr Asn Gln Ile Gly Arg Phe Phe Gly
850                 855                 860
Glu Ile Asp Pro Ser Leu Met Arg His Leu Val Asn Ile Ser Val Tyr
865                 870                 875                 880
Ala Phe Asn Lys Ser Tyr Asp Tyr Gln Ser Val Cys Glu Pro Gly Ala
                885                 890                 895
Ala Pro Lys Gln Gly Ala Gly His Arg Ser Ala Tyr Val Pro Ser Ile
            900                 905                 910
Ala Asp Ile Leu His Ile Gly Trp Trp Ala Thr Ala Ala Trp Ser
        915                 920                 925
Ile Leu Gln Gln Phe Leu Leu Ser Leu Thr Phe Pro Arg Leu Leu Glu
        930                 935                 940
Ala Val Glu Met Glu Asp Asp Phe Thr Ala Ser Leu Ser Lys Gln
945                 950                 955                 960
Ser Cys Ile Thr Glu Gln Thr Gln Tyr Phe Asp Asn Asp Ser Lys
                965                 970                 975
Ser Phe Ser Gly Val Leu Asp Cys Gly Asn Cys Ser Arg Ile Phe His
            980                 985                 990
Val Glu Lys Leu Met Asn Thr Asn Leu Ile Phe Ile Met Val Glu Ser
```

-continued

```
                995                 1000                1005
Lys Gly Thr Cys Pro Cys Asp Thr Arg Leu Leu Ile Gln Ala Glu Gln
       1010                1015                1020

Thr Ser Asp Gly Pro Asp Pro Cys Asp Met Val Lys
1025                1030                1035

<210> SEQ ID NO 8
<211> LENGTH: 1063
<212> TYPE: PRT
<213> ORGANISM: Sus scrofa

<400> SEQUENCE: 8

Met Ala Ala Gly Cys Leu Leu Ala Leu Thr Leu Thr Leu Phe Gln Ser
  1               5                  10                  15

Leu Leu Ile Gly Pro Ser Ser Gln Glu Pro Phe Pro Ser Ala Val Thr
             20                  25                  30

Ile Lys Ser Trp Val Asp Lys Met Gln Glu Asp Leu Val Thr Leu Ala
         35                  40                  45

Lys Thr Ala Ser Gly Val Asn Gln Leu Val Asp Ile Tyr Glu Lys Tyr
     50                  55                  60

Gln Asp Leu Tyr Thr Val Glu Pro Asn Asn Ala Arg Gln Leu Val Glu
 65                  70                  75                  80

Ile Ala Ala Arg Asp Ile Glu Lys Leu Leu Ser Asn Arg Ser Lys Ala
                 85                  90                  95

Leu Val Arg Leu Ala Leu Glu Ala Glu Lys Val Gln Ala Ala His Gln
            100                 105                 110

Trp Arg Glu Asp Phe Ala Ser Asn Glu Val Val Tyr Tyr Asn Ala Lys
        115                 120                 125

Asp Asp Leu Asp Pro Glu Lys Asn Asp Ser Glu Pro Gly Ser Gln Arg
    130                 135                 140

Ile Lys Pro Val Phe Ile Asp Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
            180                 185                 190

Phe Lys Lys Asn Arg Glu Glu Asp Pro Ser Leu Leu Trp Gln Val Phe
        195                 200                 205

Gly Ser Ala Thr Gly Leu Ala Arg Tyr Tyr Pro Ala Ser Pro Trp Val
    210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
            260                 265                 270

Arg Thr Ser Val Ser Glu Met Leu Glu Thr Leu Ser Asp Asp Asp Phe
        275                 280                 285

Val Asn Val Ala Ser Phe Asn Ser Asn Ala Gln Asp Val Ser Cys Phe
    290                 295                 300

Gln His Leu Val Gln Ala Asn Val Arg Asn Lys Lys Val Leu Lys Asp
305                 310                 315                 320

Ala Val Asn Asn Ile Thr Ala Lys Gly Ile Thr Asp Tyr Lys Lys Gly
                325                 330                 335
```

```
Phe Ser Phe Ala Phe Glu Gln Leu Leu Asn Tyr Asn Val Ser Arg Ala
            340                 345                 350

Asn Cys Asn Lys Ile Ile Met Leu Phe Thr Asp Gly Gly Glu Glu Arg
            355                 360                 365

Ala Gln Glu Ile Phe Ala Lys Tyr Asn Lys Asp Lys Lys Val Arg Val
    370                 375                 380

Phe Thr Phe Ser Val Gly Gln His Asn Tyr Asp Arg Gly Pro Ile Gln
385                 390                 395                 400

Trp Met Ala Cys Glu Asn Lys Gly Tyr Tyr Glu Ile Pro Ser Ile
                405                 410                 415

Gly Ala Ile Arg Ile Asn Thr Gln Glu Tyr Leu Asp Val Leu Gly Arg
            420                 425                 430

Pro Met Val Leu Ala Gly Asp Lys Ala Lys Gln Val Gln Trp Thr Asn
            435                 440                 445

Val Tyr Leu Asp Ala Leu Glu Leu Gly Leu Val Ile Thr Gly Thr Leu
    450                 455                 460

Pro Val Phe Asn Ile Thr Gly Gln Asn Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
            500                 505                 510

Phe Ala Ile Asp Pro Asn Gly Tyr Val Leu Leu His Pro Asn Leu Gln
            515                 520                 525

Pro Lys Asn Pro Lys Ser Gln Glu Pro Val Thr Leu Asp Phe Leu Asp
            530                 535                 540

Ala Glu Leu Glu Asn Asp Ile Lys Val Glu Ile Arg Asn Lys Met Ile
545                 550                 555                 560

Asp Gly Glu Ser Gly Glu Lys Thr Phe Arg Thr Leu Val Lys Ser Gln
                565                 570                 575

Asp Glu Arg Tyr Ile Asp Lys Gly Asn Arg Thr Tyr Thr Trp Thr Pro
            580                 585                 590

Val Asn Gly Thr Asp Tyr Ser Leu Ala Leu Val Leu Pro Thr Tyr Ser
            595                 600                 605

Phe Tyr Tyr Ile Lys Ala Lys Ile Glu Glu Thr Ile Thr Gln Ala Arg
            610                 615                 620

Ser Lys Lys Gly Lys Met Lys Asp Ser Glu Thr Leu Lys Pro Asp Asn
625                 630                 635                 640

Phe Glu Glu Ser Gly Tyr Thr Phe Ile Ala Pro Arg Asp Tyr Cys Asn
                645                 650                 655

Asp Leu Lys Ile Ser Asp Asn Asn Thr Glu Phe Leu Leu Asn Phe Asn
            660                 665                 670

Glu Phe Ile Asp Arg Lys Thr Pro Asn Asn Pro Ser Cys Asn Thr Asp
            675                 680                 685

Leu Ile Asn Arg Val Leu Leu Asp Ala Gly Phe Thr Asn Glu Leu Val
    690                 695                 700

Gln Asn Tyr Trp Ser Lys Gln Lys Asn Ile Lys Gly Val Lys Ala Arg
705                 710                 715                 720

Phe Val Val Thr Asp Gly Gly Ile Thr Arg Val Tyr Pro Lys Glu Ala
                725                 730                 735

Gly Glu Asn Trp Gln Glu Asn Pro Glu Thr Tyr Glu Asp Ser Phe Tyr
            740                 745                 750

Lys Arg Ser Leu Asp Asn Asp Asn Tyr Val Phe Thr Ala Pro Tyr Phe
```

-continued

```
                755                 760                 765
Asn Lys Ser Gly Pro Gly Ala Tyr Glu Ser Gly Ile Met Val Ser Lys
    770                 775                 780

Ala Val Glu Ile Tyr Ile Gln Gly Lys Leu Leu Lys Pro Ala Val Val
785                 790                 795                 800

Gly Ile Lys Ile Asp Val Asn Ser Trp Ile Glu Asn Phe Thr Lys Thr
                805                 810                 815

Ser Ile Arg Asp Pro Cys Ala Gly Pro Val Cys Asp Cys Lys Arg Asn
            820                 825                 830

Ser Asp Val Met Asp Cys Val Ile Leu Asp Asp Gly Gly Phe Leu Leu
            835                 840                 845

Met Ala Asn His Asp Asp Tyr Thr Asn Gln Ile Gly Arg Phe Phe Gly
850                 855                 860

Glu Ile Asp Pro Ser Leu Met Arg His Leu Val Asn Ile Ser Val Tyr
865                 870                 875                 880

Ala Phe Asn Lys Ser Tyr Asp Tyr Gln Ser Val Cys Glu Pro Gly Ala
                885                 890                 895

Ala Pro Lys Gln Gly Ala Gly His Arg Ser Ala Tyr Val Pro Ser Ile
            900                 905                 910

Ala Asp Ile Leu His Ile Gly Trp Trp Ala Thr Ala Ala Ala Trp Ser
            915                 920                 925

Ile Leu Gln Gln Phe Leu Leu Ser Leu Thr Phe Pro Arg Leu Leu Glu
        930                 935                 940

Ala Val Glu Met Glu Asp Asp Phe Thr Ala Ser Leu Ser Lys Gln
945                 950                 955                 960

Ser Cys Ile Thr Glu Gln Thr Gln Tyr Phe Phe Asp Asn Asp Ser Lys
                965                 970                 975

Ser Phe Ser Gly Val Leu Asp Cys Gly Asn Cys Ser Arg Ile Phe His
            980                 985                 990

Val Glu Lys Leu Met Asn Thr Asn Leu Ile Phe Ile Met Val Glu Ser
            995                 1000                1005

Lys Gly Thr Cys Pro Cys Asp Thr Arg Leu Leu Ile Gln Ala Glu Gln
    1010                1015                1020

Thr Ser Asp Gly Pro Asp Pro Cys Asp Met Val Lys Gln Pro Arg Tyr
1025                1030                1035                1040

Arg Lys Gly Pro Asp Val Cys Phe Asp Asn Asn Ala Leu Glu Asp Tyr
                1045                1050                1055

Thr Asp Cys Gly Gly Val Ser
            1060
```

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 9
ggggattgat cttcgatcgc g                                      21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:primer -continued

```
<400> SEQUENCE: 10
ctgagatttg gggttctttg g                                              21

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence:peptide

<400> SEQUENCE: 11
```

Val Glu Met Glu Asp Asp Asp Phe Thr Ala Ser Leu Ser Lys Gln Ser
 1               5                  10                  15

Cys

```
<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 12
tggcttatcg aaattaatac g                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 13
aactccgggg attgatcttc g                                              21

<210> SEQ ID NO 14
<211> LENGTH: 1091
<212> TYPE: PRT
<213> ORGANISM: Homo sapiens

<400> SEQUENCE: 14
```

Met Ala Ala Gly Cys Leu Leu Ala Leu Thr Leu Thr Leu Phe Gln Ser
 1               5                  10                  15

Leu Leu Ile Gly Pro Ser Ser Glu Glu Pro Phe Pro Ser Ala Val Thr
                20                  25                  30

Ile Lys Ser Trp Val Asp Lys Met Gln Glu Asp Leu Val Thr Leu Ala
            35                  40                  45

Lys Thr Ala Ser Gly Val Asn Gln Leu Val Asp Ile Tyr Glu Lys Tyr
        50                  55                  60

Gln Asp Leu Tyr Thr Val Glu Pro Asn Asn Ala Arg Gln Leu Val Glu
65                  70                  75                  80

Ile Ala Ala Arg Asp Ile Glu Lys Leu Leu Ser Asn Arg Ser Lys Ala
                85                  90                  95

Leu Val Ser Leu Ala Leu Glu Ala Glu Lys Val Gln Ala Ala His Gln
            100                 105                 110

Trp Arg Glu Asp Phe Ala Ser Asn Glu Val Val Tyr Tyr Asn Ala Lys
        115                 120                 125

Asp Asp Leu Asp Pro Glu Lys Asn Asp Ser Glu Pro Gly Ser Gln Arg
    130                 135                 140

Ile Lys Pro Val Phe Ile Glu Asp Ala Asn Phe Gly Arg Gln Ile Ser

```
            145                 150                 155                 160
Tyr Gln His Ala Ala Val His Ile Pro Thr Asp Ile Tyr Glu Gly Ser
                    165                 170                 175

Thr Ile Val Leu Asn Glu Leu Asn Trp Thr Ser Ala Leu Asp Glu Val
                180                 185                 190

Phe Lys Lys Asn Arg Glu Glu Asp Pro Ser Leu Leu Trp Gln Val Phe
            195                 200                 205

Gly Ser Ala Thr Gly Leu Ala Arg Tyr Tyr Pro Ala Ser Pro Trp Val
        210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
                260                 265                 270

Arg Thr Ser Val Ser Glu Met Leu Glu Thr Leu Ser Asp Asp Asp Phe
                275                 280                 285

Val Asn Val Ala Ser Phe Asn Ser Asn Ala Gln Asp Val Ser Cys Phe
    290                 295                 300

Gln His Leu Val Gln Ala Asn Val Arg Asn Lys Lys Val Leu Lys Asp
305                 310                 315                 320

Ala Val Asn Asn Ile Thr Ala Lys Gly Ile Thr Asp Tyr Lys Lys Gly
                325                 330                 335

Phe Ser Phe Ala Phe Glu Gln Leu Leu Asn Tyr Asn Val Ser Arg Ala
                340                 345                 350

Asn Cys Asn Lys Ile Ile Met Leu Phe Thr Asp Gly Gly Glu Glu Arg
                355                 360                 365

Ala Gln Glu Ile Phe Asn Lys Tyr Asn Lys Asp Lys Lys Val Arg Val
        370                 375                 380

Phe Arg Phe Ser Val Gly Gln His Asn Tyr Glu Arg Gly Pro Ile Gln
385                 390                 395                 400

Trp Met Ala Cys Glu Asn Lys Gly Tyr Tyr Tyr Glu Ile Pro Ser Ile
                405                 410                 415

Gly Ala Ile Arg Ile Asn Thr Gln Glu Tyr Leu Asp Val Leu Gly Arg
                420                 425                 430

Pro Met Val Leu Ala Gly Asp Lys Ala Lys Gln Val Gln Trp Thr Asn
            435                 440                 445

Val Tyr Leu Asp Ala Leu Glu Leu Gly Leu Val Ile Thr Gly Thr Leu
    450                 455                 460

Pro Val Phe Asn Ile Thr Gly Gln Phe Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
                500                 505                 510

Phe Ala Ile Asp Pro Asn Gly Tyr Val Leu Leu His Pro Asn Leu Gln
                515                 520                 525

Pro Lys Asn Pro Lys Ser Gln Glu Pro Val Thr Leu Asp Phe Leu Asp
            530                 535                 540

Ala Glu Leu Glu Asn Asp Ile Lys Val Glu Ile Arg Asn Lys Met Ile
545                 550                 555                 560

Asp Gly Glu Ser Gly Glu Lys Thr Phe Arg Thr Leu Val Lys Ser Gln
                565                 570                 575
```

```
Asp Glu Arg Tyr Ile Asp Lys Gly Asn Arg Thr Tyr Thr Trp Thr Pro
            580                 585                 590

Val Asn Gly Thr Asp Tyr Ser Leu Ala Leu Val Leu Pro Thr Tyr Ser
            595                 600                 605

Phe Tyr Tyr Ile Lys Ala Lys Leu Glu Glu Thr Ile Thr Gln Ala Arg
            610                 615                 620

Ser Lys Lys Gly Lys Met Lys Asp Ser Glu Thr Leu Lys Pro Asp Asn
625                 630                 635                 640

Phe Glu Glu Ser Gly Tyr Thr Phe Ile Ala Pro Arg Asp Tyr Cys Asn
                    645                 650                 655

Asp Leu Lys Ile Ser Asp Asn Thr Glu Phe Leu Leu Asn Phe Asn
            660                 665                 670

Glu Phe Ile Asp Arg Lys Thr Pro Asn Asn Pro Ser Cys Asn Ala Asp
            675                 680                 685

Leu Ile Asn Arg Val Leu Leu Asp Ala Gly Phe Thr Asn Glu Leu Val
            690                 695                 700

Gln Asn Tyr Trp Ser Lys Gln Lys Asn Ile Lys Gly Val Lys Ala Arg
705                 710                 715                 720

Phe Val Val Thr Asp Gly Gly Ile Thr Arg Val Tyr Pro Lys Glu Ala
                    725                 730                 735

Gly Glu Asn Trp Gln Glu Asn Pro Glu Thr Tyr Glu Asp Ser Phe Tyr
            740                 745                 750

Lys Arg Ser Leu Asp Asn Asp Asn Tyr Val Phe Thr Ala Pro Tyr Phe
            755                 760                 765

Asn Lys Ser Gly Pro Gly Ala Tyr Glu Ser Gly Ile Met Val Ser Lys
770                 775                 780

Ala Val Glu Ile Tyr Ile Gln Gly Lys Leu Leu Lys Pro Ala Val Val
785                 790                 795                 800

Gly Ile Lys Ile Asp Val Asn Ser Trp Ile Glu Asn Phe Thr Lys Thr
                    805                 810                 815

Ser Ile Arg Asp Pro Cys Ala Gly Pro Val Cys Asp Cys Lys Arg Asn
            820                 825                 830

Ser Asp Val Met Asp Cys Val Ile Leu Asp Asp Gly Gly Phe Leu Leu
            835                 840                 845

Met Ala Asn His Asp Asp Tyr Thr Asn Gln Ile Gly Arg Phe Phe Gly
            850                 855                 860

Glu Ile Asp Pro Ser Leu Met Arg His Leu Val Asn Ile Ser Val Tyr
865                 870                 875                 880

Ala Phe Asn Lys Ser Tyr Asp Tyr Gln Ser Val Cys Glu Pro Gly Ala
                    885                 890                 895

Ala Pro Lys Gln Gly Ala Gly His Arg Ser Ala Tyr Val Pro Ser Val
            900                 905                 910

Ala Asp Ile Leu Gln Ile Gly Trp Trp Ala Thr Ala Ala Ala Trp Ser
            915                 920                 925

Ile Leu Gln Gln Phe Leu Leu Ser Leu Thr Phe Pro Arg Leu Leu Glu
            930                 935                 940

Ala Val Glu Met Glu Asp Asp Asp Phe Thr Ala Ser Leu Ser Lys Gln
945                 950                 955                 960

Ser Cys Ile Thr Glu Gln Thr Gln Tyr Phe Phe Asp Asn Asp Ser Lys
                    965                 970                 975

Ser Phe Ser Gly Val Leu Asp Cys Gly Asn Cys Ser Arg Ile Phe His
            980                 985                 990
```

-continued

Gly Glu Lys Leu Met Asn Thr Asn Leu Ile Phe Ile Met Val Glu Ser
        995                 1000                1005

Lys Gly Thr Cys Pro Cys Asp Thr Arg Leu Leu Ile Gln Ala Glu Gln
    1010                1015                1020

Thr Ser Asp Gly Pro Asn Pro Cys Asp Met Val Lys Gln Pro Arg Tyr
1025                1030                1035                1040

Arg Lys Gly Pro Asp Val Cys Phe Asp Asn Asn Val Leu Glu Asp Tyr
                1045                1050                1055

Thr Asp Cys Gly Gly Val Ser Gly Leu Asn Pro Ser Leu Trp Tyr Ile
            1060                1065                1070

Ile Gly Ile Gln Phe Leu Leu Leu Trp Leu Val Ser Gly Ser Thr His
        1075                1080                1085

Arg Leu Leu
    1090

<210> SEQ ID NO 15
<211> LENGTH: 1018
<212> TYPE: PRT
<213> ORGANISM: Homo sapiens

<400> SEQUENCE: 15

Met Ala Ala Gly Cys Leu Leu Ala Leu Thr Leu Thr Leu Phe Gln Ser
1               5                   10                  15

Leu Leu Ile Gly Pro Ser Ser Glu Glu Pro Phe Pro Ser Ala Val Thr
            20                  25                  30

Ile Lys Ser Trp Val Asp Lys Met Gln Glu Asp Leu Val Thr Leu Ala
        35                  40                  45

Lys Thr Ala Ser Gly Val Asn Gln Leu Val Asp Ile Tyr Glu Lys Tyr
    50                  55                  60

Gln Asp Leu Tyr Thr Val Glu Pro Asn Asn Ala Arg Gln Leu Val Glu
65                  70                  75                  80

Ile Ala Ala Arg Asp Ile Glu Lys Leu Leu Ser Asn Arg Ser Lys Ala
                85                  90                  95

Leu Val Ser Leu Ala Leu Glu Ala Glu Lys Val Gln Ala Ala His Gln
            100                 105                 110

Trp Arg Glu Asp Phe Ala Ser Asn Glu Val Val Tyr Tyr Asn Ala Lys
        115                 120                 125

Asp Asp Leu Asp Pro Glu Lys Asn Asp Ser Glu Pro Gly Ser Gln Arg
    130                 135                 140

Ile Lys Pro Val Phe Ile Glu Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
            180                 185                 190

Phe Lys Lys Asn Arg Glu Glu Asp Pro Ser Leu Leu Trp Gln Val Phe
        195                 200                 205

Gly Ser Ala Thr Gly Leu Ala Arg Tyr Tyr Pro Ala Ser Pro Trp Val
    210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
            260                 265                 270

```
Arg Thr Ser Val Ser Glu Met Leu Glu Thr Leu Ser Asp Asp Phe
        275                 280                 285

Val Asn Val Ala Ser Phe Asn Ser Asn Ala Gln Asp Val Ser Cys Phe
        290                 295                 300

Gln His Leu Val Gln Ala Asn Val Arg Asn Lys Lys Val Leu Lys Asp
305                 310                 315                 320

Ala Val Asn Asn Ile Thr Ala Lys Gly Ile Thr Asp Tyr Lys Lys Gly
                325                 330                 335

Phe Ser Phe Ala Phe Glu Gln Leu Leu Asn Tyr Asn Val Ser Arg Ala
                340                 345                 350

Asn Cys Asn Lys Ile Ile Met Leu Phe Thr Asp Gly Gly Glu Glu Arg
        355                 360                 365

Ala Gln Glu Ile Phe Asn Lys Tyr Asn Lys Asp Lys Lys Val Arg Val
        370                 375                 380

Phe Arg Phe Ser Val Gly Gln His Asn Tyr Glu Arg Gly Pro Ile Gln
385                 390                 395                 400

Trp Met Ala Cys Glu Asn Lys Gly Tyr Tyr Tyr Glu Ile Pro Ser Ile
                405                 410                 415

Gly Ala Ile Arg Ile Asn Thr Gln Glu Tyr Leu Asp Val Leu Gly Arg
                420                 425                 430

Pro Met Val Leu Ala Gly Asp Lys Ala Lys Gln Val Gln Trp Thr Asn
        435                 440                 445

Val Tyr Leu Asp Ala Leu Glu Leu Gly Leu Val Ile Thr Gly Thr Leu
        450                 455                 460

Pro Val Phe Asn Ile Thr Gly Gln Phe Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
                500                 505                 510

Phe Ala Ile Asp Pro Asn Gly Tyr Val Leu Leu His Pro Asn Leu Gln
        515                 520                 525

Pro Lys Asn Pro Lys Ser Gln Glu Pro Val Thr Leu Asp Phe Leu Asp
        530                 535                 540

Ala Glu Leu Glu Asn Asp Ile Lys Val Glu Ile Arg Asn Lys Met Ile
545                 550                 555                 560

Asp Gly Glu Ser Gly Glu Lys Thr Phe Arg Thr Leu Val Lys Ser Gln
                565                 570                 575

Asp Glu Arg Tyr Ile Asp Lys Gly Asn Arg Thr Tyr Thr Trp Thr Pro
                580                 585                 590

Val Asn Gly Thr Asp Tyr Ser Leu Ala Leu Val Leu Pro Thr Tyr Ser
        595                 600                 605

Phe Tyr Tyr Ile Lys Ala Lys Leu Glu Glu Thr Ile Thr Gln Ala Arg
        610                 615                 620

Ser Lys Lys Gly Lys Met Lys Asp Ser Glu Thr Leu Lys Pro Asp Asn
625                 630                 635                 640

Phe Glu Glu Ser Gly Tyr Thr Phe Ile Ala Pro Arg Asp Tyr Cys Asn
                645                 650                 655

Asp Leu Lys Ile Ser Asp Asn Asn Thr Glu Phe Leu Leu Asn Phe Asn
                660                 665                 670

Glu Phe Ile Asp Arg Lys Thr Pro Asn Asn Pro Ser Cys Asn Ala Asp
        675                 680                 685
```

-continued

```
Leu Ile Asn Arg Val Leu Leu Asp Ala Gly Phe Thr Asn Glu Leu Val
    690                 695                 700

Gln Asn Tyr Trp Ser Lys Gln Lys Asn Ile Lys Gly Val Lys Ala Arg
705                 710                 715                 720

Phe Val Val Thr Asp Gly Gly Ile Thr Arg Val Tyr Pro Lys Glu Ala
                725                 730                 735

Gly Glu Asn Trp Gln Glu Asn Pro Glu Thr Tyr Glu Asp Ser Phe Tyr
            740                 745                 750

Lys Arg Ser Leu Asp Asn Asp Asn Tyr Val Phe Thr Ala Pro Tyr Phe
        755                 760                 765

Asn Lys Ser Gly Pro Gly Ala Tyr Glu Ser Gly Ile Met Val Ser Lys
    770                 775                 780

Ala Val Glu Ile Tyr Ile Gln Gly Lys Leu Leu Lys Pro Ala Val Val
785                 790                 795                 800

Gly Ile Lys Ile Asp Val Asn Ser Trp Ile Glu Asn Phe Thr Lys Thr
                805                 810                 815

Ser Ile Arg Asp Pro Cys Ala Gly Pro Val Cys Asp Cys Lys Arg Asn
            820                 825                 830

Ser Asp Val Met Asp Cys Val Ile Leu Asp Asp Gly Gly Phe Leu Leu
        835                 840                 845

Met Ala Asn His Asp Asp Tyr Thr Asn Gln Ile Gly Arg Phe Phe Gly
    850                 855                 860

Glu Ile Asp Pro Ser Leu Met Arg His Leu Val Asn Ile Ser Val Tyr
865                 870                 875                 880

Ala Phe Asn Lys Ser Tyr Asp Tyr Gln Ser Val Cys Glu Pro Gly Ala
                885                 890                 895

Ala Pro Lys Gln Gly Ala Gly His Arg Ser Ala Tyr Val Pro Ser Val
            900                 905                 910

Ala Asp Ile Leu Gln Ile Gly Trp Trp Ala Thr Ala Ala Ala Trp Ser
        915                 920                 925

Ile Leu Gln Gln Phe Leu Leu Ser Leu Thr Phe Pro Arg Leu Leu Glu
    930                 935                 940

Ala Val Glu Met Glu Asp Asp Phe Thr Ala Ser Leu Ser Lys Gln
945                 950                 955                 960

Ser Cys Ile Thr Glu Gln Thr Gln Tyr Phe Phe Asp Asn Asp Ser Lys
                965                 970                 975

Ser Phe Ser Gly Val Leu Asp Cys Gly Asn Cys Ser Arg Ile Phe His
            980                 985                 990

Gly Glu Lys Leu Met Asn Thr Asn Leu Ile Phe Ile Met Val Glu Ser
        995                 1000                1005

Lys Gly Thr Cys Pro Cys Asp Thr Arg Leu
    1010                1015
```

<210> SEQ ID NO 16
<211> LENGTH: 1036
<212> TYPE: PRT
<213> ORGANISM: Homo sapiens

<400> SEQUENCE: 16

```
Met Ala Ala Gly Cys Leu Leu Ala Leu Thr Leu Thr Leu Phe Gln Ser
1               5                   10                  15

Leu Leu Ile Gly Pro Ser Ser Glu Glu Pro Phe Pro Ser Ala Val Thr
            20                  25                  30

Ile Lys Ser Trp Val Asp Lys Met Gln Glu Asp Leu Val Thr Leu Ala
        35                  40                  45
```

```
Lys Thr Ala Ser Gly Val Asn Gln Leu Val Asp Ile Tyr Glu Lys Tyr
     50                  55                  60

Gln Asp Leu Tyr Thr Val Glu Pro Asn Asn Ala Arg Gln Leu Val Glu
 65                  70                  75                  80

Ile Ala Ala Arg Asp Ile Glu Lys Leu Leu Ser Asn Arg Ser Lys Ala
                 85                  90                  95

Leu Val Ser Leu Ala Leu Glu Ala Glu Lys Val Gln Ala Ala His Gln
            100                 105                 110

Trp Arg Glu Asp Phe Ala Ser Asn Glu Val Val Tyr Tyr Asn Ala Lys
        115                 120                 125

Asp Asp Leu Asp Pro Glu Lys Asn Asp Ser Glu Pro Gly Ser Gln Arg
130                 135                 140

Ile Lys Pro Val Phe Ile Glu Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
            180                 185                 190

Phe Lys Lys Asn Arg Glu Glu Asp Pro Ser Leu Leu Trp Gln Val Phe
        195                 200                 205

Gly Ser Ala Thr Gly Leu Ala Arg Tyr Tyr Pro Ala Ser Pro Trp Val
210                 215                 220

Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
            260                 265                 270

Arg Thr Ser Val Ser Glu Met Leu Glu Thr Leu Ser Asp Asp Asp Phe
        275                 280                 285

Val Asn Val Ala Ser Phe Asn Ser Asn Ala Gln Asp Val Ser Cys Phe
290                 295                 300

Gln His Leu Val Gln Ala Asn Val Arg Asn Lys Lys Val Leu Lys Asp
305                 310                 315                 320

Ala Val Asn Asn Ile Thr Ala Lys Gly Ile Thr Asp Tyr Lys Lys Gly
                325                 330                 335

Phe Ser Phe Ala Phe Glu Gln Leu Leu Asn Tyr Asn Val Ser Arg Ala
            340                 345                 350

Asn Cys Asn Lys Ile Ile Met Leu Phe Thr Asp Gly Gly Glu Glu Arg
        355                 360                 365

Ala Gln Glu Ile Phe Asn Lys Tyr Asn Lys Asp Lys Lys Val Arg Val
370                 375                 380

Phe Arg Phe Ser Val Gly Gln His Asn Tyr Glu Arg Gly Pro Ile Gln
385                 390                 395                 400

Trp Met Ala Cys Glu Asn Lys Gly Tyr Tyr Glu Ile Pro Ser Ile
                405                 410                 415

Gly Ala Ile Arg Ile Asn Thr Gln Glu Tyr Leu Asp Val Leu Gly Arg
            420                 425                 430

Pro Met Val Leu Ala Gly Asp Lys Ala Lys Gln Val Gln Trp Thr Asn
        435                 440                 445

Val Tyr Leu Asp Ala Leu Glu Leu Gly Leu Val Ile Thr Gly Thr Leu
450                 455                 460
```

```
Pro Val Phe Asn Ile Thr Gly Gln Phe Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
            500                 505                 510

Phe Ala Ile Asp Pro Asn Gly Tyr Val Leu Leu His Pro Asn Leu Gln
            515                 520                 525

Pro Lys Asn Pro Lys Ser Gln Glu Pro Val Thr Leu Asp Phe Leu Asp
            530                 535                 540

Ala Glu Leu Glu Asn Asp Ile Lys Val Glu Ile Arg Asn Lys Met Ile
545                 550                 555                 560

Asp Gly Glu Ser Gly Glu Lys Thr Phe Arg Thr Leu Val Lys Ser Gln
                565                 570                 575

Asp Glu Arg Tyr Ile Asp Lys Gly Asn Arg Thr Tyr Thr Trp Thr Pro
            580                 585                 590

Val Asn Gly Thr Asp Tyr Ser Leu Ala Leu Val Leu Pro Thr Tyr Ser
            595                 600                 605

Phe Tyr Tyr Ile Lys Ala Lys Leu Glu Glu Thr Ile Thr Gln Ala Arg
            610                 615                 620

Ser Lys Lys Gly Lys Met Lys Asp Ser Glu Thr Leu Lys Pro Asp Asn
625                 630                 635                 640

Phe Glu Glu Ser Gly Tyr Thr Phe Ile Ala Pro Arg Asp Tyr Cys Asn
                645                 650                 655

Asp Leu Lys Ile Ser Asp Asn Asn Thr Glu Phe Leu Leu Asn Phe Asn
            660                 665                 670

Glu Phe Ile Asp Arg Lys Thr Pro Asn Asn Pro Ser Cys Asn Ala Asp
            675                 680                 685

Leu Ile Asn Arg Val Leu Leu Asp Ala Gly Phe Thr Asn Glu Leu Val
            690                 695                 700

Gln Asn Tyr Trp Ser Lys Gln Lys Asn Ile Lys Gly Val Lys Ala Arg
705                 710                 715                 720

Phe Val Val Thr Asp Gly Gly Ile Thr Arg Val Tyr Pro Lys Glu Ala
                725                 730                 735

Gly Glu Asn Trp Gln Glu Asn Pro Glu Thr Tyr Glu Asp Ser Phe Tyr
            740                 745                 750

Lys Arg Ser Leu Asp Asn Asp Asn Tyr Val Phe Thr Ala Pro Tyr Phe
            755                 760                 765

Asn Lys Ser Gly Pro Gly Ala Tyr Glu Ser Gly Ile Met Val Ser Lys
            770                 775                 780

Ala Val Glu Ile Tyr Ile Gln Gly Lys Leu Leu Lys Pro Ala Val Val
785                 790                 795                 800

Gly Ile Lys Ile Asp Val Asn Ser Trp Ile Glu Asn Phe Thr Lys Thr
                805                 810                 815

Ser Ile Arg Asp Pro Cys Ala Gly Pro Val Cys Asp Cys Lys Arg Asn
            820                 825                 830

Ser Asp Val Met Asp Cys Val Ile Leu Asp Asp Gly Gly Phe Leu Leu
            835                 840                 845

Met Ala Asn His Asp Asp Tyr Thr Asn Gln Ile Gly Arg Phe Phe Gly
850                 855                 860

Glu Ile Asp Pro Ser Leu Met Arg His Leu Val Asn Ile Ser Val Tyr
865                 870                 875                 880

Ala Phe Asn Lys Ser Tyr Asp Tyr Gln Ser Val Cys Glu Pro Gly Ala
```

-continued

```
                    885                 890                 895
Ala Pro Lys Gln Gly Ala Gly His Arg Ser Ala Tyr Val Pro Ser Val
                900                 905                 910

Ala Asp Ile Leu Gln Ile Gly Trp Trp Ala Thr Ala Ala Ala Trp Ser
            915                 920                 925

Ile Leu Gln Gln Phe Leu Leu Ser Leu Thr Phe Pro Arg Leu Leu Glu
        930                 935                 940

Ala Val Glu Met Glu Asp Asp Phe Thr Ala Ser Leu Ser Lys Gln
945                 950                 955                 960

Ser Cys Ile Thr Glu Gln Thr Gln Tyr Phe Phe Asp Asn Asp Ser Lys
                965                 970                 975

Ser Phe Ser Gly Val Leu Asp Cys Gly Asn Cys Ser Arg Ile Phe His
            980                 985                 990

Gly Glu Lys Leu Met Asn Thr Asn Leu Ile Phe Ile Met Val Glu Ser
        995                 1000                1005

Lys Gly Thr Cys Pro Cys Asp Thr Arg Leu Leu Ile Gln Ala Glu Gln
    1010                1015                1020

Thr Ser Asp Gly Pro Asn Pro Cys Asp Met Val Lys
1025                1030                1035

<210> SEQ ID NO 17
<211> LENGTH: 1063
<212> TYPE: PRT
<213> ORGANISM: Homo sapiens

<400> SEQUENCE: 17

Met Ala Ala Gly Cys Leu Leu Ala Leu Thr Leu Thr Leu Phe Gln Ser
1               5                   10                  15

Leu Leu Ile Gly Pro Ser Ser Glu Glu Pro Phe Pro Ser Ala Val Thr
                20                  25                  30

Ile Lys Ser Trp Val Asp Lys Met Gln Glu Asp Leu Val Thr Leu Ala
            35                  40                  45

Lys Thr Ala Ser Gly Val Asn Gln Leu Val Asp Ile Tyr Glu Lys Tyr
        50                  55                  60

Gln Asp Leu Tyr Thr Val Glu Pro Asn Asn Ala Arg Gln Leu Val Glu
65                  70                  75                  80

Ile Ala Ala Arg Asp Ile Glu Lys Leu Leu Ser Asn Arg Ser Lys Ala
                85                  90                  95

Leu Val Ser Leu Ala Leu Glu Ala Glu Lys Val Gln Ala Ala His Gln
                100                 105                 110

Trp Arg Glu Asp Phe Ala Ser Asn Glu Val Val Tyr Tyr Asn Ala Lys
            115                 120                 125

Asp Asp Leu Asp Pro Glu Lys Asn Asp Ser Glu Pro Gly Ser Gln Arg
        130                 135                 140

Ile Lys Pro Val Phe Ile Glu Asp Ala Asn Phe Gly Arg Gln Ile Ser
145                 150                 155                 160

Tyr Gln His Ala Ala Val His Ile Pro Thr Asp Ile Tyr Glu Gly Ser
                165                 170                 175

Thr Ile Val Leu Asn Glu Leu Asn Trp Thr Ser Ala Leu Asp Glu Val
            180                 185                 190

Phe Lys Lys Asn Arg Glu Glu Asp Pro Ser Leu Leu Trp Gln Val Phe
        195                 200                 205

Gly Ser Ala Thr Gly Leu Ala Arg Tyr Tyr Pro Ala Ser Pro Trp Val
    210                 215                 220
```

-continued

```
Asp Asn Ser Arg Thr Pro Asn Lys Ile Asp Leu Tyr Asp Val Arg Arg
225                 230                 235                 240

Arg Pro Trp Tyr Ile Gln Gly Ala Ala Ser Pro Lys Asp Met Leu Ile
                245                 250                 255

Leu Val Asp Val Ser Gly Ser Val Ser Gly Leu Thr Leu Lys Leu Ile
            260                 265                 270

Arg Thr Ser Val Ser Glu Met Leu Glu Thr Leu Ser Asp Asp Asp Phe
        275                 280                 285

Val Asn Val Ala Ser Phe Asn Ser Asn Ala Gln Asp Val Ser Cys Phe
    290                 295                 300

Gln His Leu Val Gln Ala Asn Val Arg Asn Lys Val Leu Lys Asp
305                 310                 315                 320

Ala Val Asn Asn Ile Thr Ala Lys Gly Ile Thr Asp Tyr Lys Lys Gly
                325                 330                 335

Phe Ser Phe Ala Phe Glu Gln Leu Leu Asn Tyr Asn Val Ser Arg Ala
                340                 345                 350

Asn Cys Asn Lys Ile Ile Met Leu Phe Thr Asp Gly Gly Glu Glu Arg
        355                 360                 365

Ala Gln Glu Ile Phe Asn Lys Tyr Asn Lys Asp Lys Lys Val Arg Val
370                 375                 380

Phe Arg Phe Ser Val Gly Gln His Asn Tyr Glu Arg Gly Pro Ile Gln
385                 390                 395                 400

Trp Met Ala Cys Glu Asn Lys Gly Tyr Tyr Glu Ile Pro Ser Ile
                405                 410                 415

Gly Ala Ile Arg Ile Asn Thr Gln Glu Tyr Leu Asp Val Leu Gly Arg
                420                 425                 430

Pro Met Val Leu Ala Gly Asp Lys Ala Lys Gln Val Gln Trp Thr Asn
            435                 440                 445

Val Tyr Leu Asp Ala Leu Glu Leu Gly Leu Val Ile Thr Gly Thr Leu
    450                 455                 460

Pro Val Phe Asn Ile Thr Gly Gln Phe Glu Asn Lys Thr Asn Leu Lys
465                 470                 475                 480

Asn Gln Leu Ile Leu Gly Val Met Gly Val Asp Val Ser Leu Glu Asp
                485                 490                 495

Ile Lys Arg Leu Thr Pro Arg Phe Thr Leu Cys Pro Asn Gly Tyr Tyr
            500                 505                 510

Phe Ala Ile Asp Pro Asn Gly Tyr Val Leu Leu His Pro Asn Leu Gln
        515                 520                 525

Pro Lys Asn Pro Lys Ser Gln Glu Pro Val Thr Leu Asp Phe Leu Asp
530                 535                 540

Ala Glu Leu Glu Asn Asp Ile Lys Val Glu Ile Arg Asn Lys Met Ile
545                 550                 555                 560

Asp Gly Glu Ser Gly Glu Lys Thr Phe Arg Thr Leu Val Lys Ser Gln
                565                 570                 575

Asp Glu Arg Tyr Ile Asp Lys Gly Asn Arg Thr Tyr Thr Trp Thr Pro
            580                 585                 590

Val Asn Gly Thr Asp Tyr Ser Leu Ala Leu Val Leu Pro Thr Tyr Ser
        595                 600                 605

Phe Tyr Tyr Ile Lys Ala Lys Leu Glu Glu Thr Ile Thr Gln Ala Arg
        610                 615                 620

Ser Lys Lys Gly Lys Met Lys Asp Ser Glu Thr Leu Lys Pro Asp Asn
625                 630                 635                 640

Phe Glu Glu Ser Gly Tyr Thr Phe Ile Ala Pro Arg Asp Tyr Cys Asn
```

-continued

```
                645                 650                 655
Asp Leu Lys Ile Ser Asp Asn Asn Thr Glu Phe Leu Leu Asn Phe Asn
            660                 665                 670
Glu Phe Ile Asp Arg Lys Thr Pro Asn Asn Pro Ser Cys Asn Ala Asp
            675                 680             685
Leu Ile Asn Arg Val Leu Leu Asp Ala Gly Phe Thr Asn Glu Leu Val
            690             695                 700
Gln Asn Tyr Trp Ser Lys Gln Lys Asn Ile Lys Gly Val Lys Ala Arg
705                 710                 715                 720
Phe Val Val Thr Asp Gly Gly Ile Thr Arg Val Tyr Pro Lys Glu Ala
                725                 730                 735
Gly Glu Asn Trp Gln Glu Asn Pro Glu Thr Tyr Glu Asp Ser Phe Tyr
            740                 745                 750
Lys Arg Ser Leu Asp Asn Asp Asn Tyr Val Phe Thr Ala Pro Tyr Phe
            755                 760                 765
Asn Lys Ser Gly Pro Gly Ala Tyr Glu Ser Gly Ile Met Val Ser Lys
            770                 775                 780
Ala Val Glu Ile Tyr Ile Gln Gly Lys Leu Leu Lys Pro Ala Val Val
785                 790                 795                 800
Gly Ile Lys Ile Asp Val Asn Ser Trp Ile Glu Asn Phe Thr Lys Thr
                805                 810                 815
Ser Ile Arg Asp Pro Cys Ala Gly Pro Val Cys Asp Cys Lys Arg Asn
            820                 825                 830
Ser Asp Val Met Asp Cys Val Ile Leu Asp Asp Gly Gly Phe Leu Leu
            835                 840                 845
Met Ala Asn His Asp Asp Tyr Thr Asn Gln Ile Gly Arg Phe Phe Gly
850                 855                 860
Glu Ile Asp Pro Ser Leu Met Arg His Leu Val Asn Ile Ser Val Tyr
865                 870                 875                 880
Ala Phe Asn Lys Ser Tyr Asp Tyr Gln Ser Val Cys Glu Pro Gly Ala
                885                 890                 895
Ala Pro Lys Gln Gly Ala Gly His Arg Ser Ala Tyr Val Pro Ser Val
                900                 905                 910
Ala Asp Ile Leu Gln Ile Gly Trp Trp Ala Thr Ala Ala Trp Ser
                915                 920                 925
Ile Leu Gln Gln Phe Leu Leu Ser Leu Thr Phe Pro Arg Leu Leu Glu
            930                 935                 940
Ala Val Glu Met Glu Asp Asp Phe Thr Ala Ser Leu Ser Lys Gln
945                 950                 955                 960
Ser Cys Ile Thr Glu Gln Thr Gln Tyr Phe Phe Asp Asn Asp Ser Lys
                965                 970                 975
Ser Phe Ser Gly Val Leu Asp Cys Gly Asn Cys Ser Arg Ile Phe His
            980                 985                 990
Gly Glu Lys Leu Met Asn Thr Asn Leu Ile Phe Ile Met Val Glu Ser
                995                 1000                1005
Lys Gly Thr Cys Pro Cys Asp Thr Arg Leu Leu Ile Gln Ala Glu Gln
    1010                1015                1020
Thr Ser Asp Gly Pro Asn Pro Cys Asp Met Val Lys Gln Pro Arg Tyr
1025                1030                1035                1040
Arg Lys Gly Pro Asp Val Cys Phe Asp Asn Asn Val Leu Glu Asp Tyr
            1045                1050                1055
Thr Asp Cys Gly Gly Val Ser
            1060
```

<210> SEQ ID NO 18
<211> LENGTH: 3600
<212> TYPE: DNA
<213> ORGANISM: Homo sapiens

<400> SEQUENCE: 18

| | | | | | |
|---|---|---|---|---|---|
| gcggggagg | gggcattgat | cttcgatcgc | gaagatggct | gctggctgcc | tgctggcctt | 60 |
| gactctgaca | cttttccaat | ctttgctcat | cggcccctcg | tcggaggagc | cgttcccttc | 120 |
| ggccgtcact | atcaaatcat | gggtggataa | gatgcaagaa | gaccttgtca | cactggcaaa | 180 |
| aacagcaagt | ggagtcaatc | agcttgttga | tatttatgag | aaatatcaag | atttgtatac | 240 |
| tgtggaacca | aataatgcac | gccagctggt | agaaattgca | gccagggata | ttgagaaact | 300 |
| tctgagcaac | agatctaaag | ccctggtgag | cctggcattg | gaagcggaga | agttcaagc | 360 |
| agctcaccag | tggagagaag | attttgcaag | caatgaagtt | gtctactaca | atgcaaagga | 420 |
| tgatctcgat | cctgagaaaa | atgacagtga | gccaggcagc | cagaggataa | aacctgtttt | 480 |
| cattgaagat | gctaattttg | gacgacaaat | atcttatcag | cacgcagcag | tccatattcc | 540 |
| tactgacatc | tatgagggct | caacaattgt | gttaaatgaa | ctcaactgga | caagtgcctt | 600 |
| agatgaagtt | ttcaaaaaga | atcgcgagga | agacccttca | ttattgtggc | aggttttttgg | 660 |
| cagtgccact | ggcctagctc | gatattatcc | agcttcacca | tgggttgata | atagtagaac | 720 |
| tccaaataag | attgaccttt | atgatgtacg | cagaagacca | tggtacatcc | aaggagctgc | 780 |
| atctcctaaa | gacatgctta | ttctggtgga | tgtgagtgga | agtgttagtg | gattgacact | 840 |
| taaactgatc | cgaacatctg | tctccgaaat | gttagaaacc | ctctcagatg | atgatttcgt | 900 |
| gaatgtagct | tcatttaaca | gcaatgctca | ggatgtaagc | tgttttcagc | accttgtcca | 960 |
| agcaaatgta | agaaataaaa | aagtgttgaa | agacgcggtg | aataatatca | cagccaaagg | 1020 |
| aattacagat | tataagaagg | gctttagttt | tgcttttgaa | cagctgctta | attataatgt | 1080 |
| ttccagagca | aactgcaata | agattattat | gctattcacg | gatggaggag | aagagagagc | 1140 |
| ccaggagata | tttaacaaat | acaataaaga | taaaaagta | cgtgtattca | ggttttcagt | 1200 |
| tggtcaacac | aattatgaga | gaggacctat | tcagtggatg | gcctgtgaaa | acaaaggtta | 1260 |
| ttattatgaa | attccttcca | ttggtgcaat | aagaatcaat | actcaggaat | atttggatgt | 1320 |
| tttgggaaga | ccaatggttt | tagcaggaga | caaagctaag | caagtccaat | ggacaaatgt | 1380 |
| gtacctggat | gcattggaac | tgggacttgt | cattactgga | actcttccgg | tcttcaacat | 1440 |
| aaccggccaa | tttgaaaata | agacaaactt | aaagaaccag | ctgattcttg | gtgtgatggg | 1500 |
| agtagatgtg | tcttttggaag | atattaaaag | actgacacca | cgttttacac | tgtgccccaa | 1560 |
| tgggtattac | tttgcaatcg | atcctaatgg | ttatgtttta | ttacatccaa | atcttcagcc | 1620 |
| aaagaaccc | aaatctcagg | agccagtaac | attggatttc | cttgatgcag | agttagagaa | 1680 |
| tgatattaaa | gtggagattc | gaataagat | gattgatggg | gaaagtggag | aaaaaacatt | 1740 |
| cagaactctg | gttaaatctc | aagatgagag | atatattgac | aaaggaaaca | ggacatacac | 1800 |
| atggacacct | gtcaatggca | cagattacag | tttggccttg | gtattaccaa | cctacagttt | 1860 |
| ttactatata | aaagccaaac | tagaagagac | aataactcag | gccagatcaa | aaagggcaa | 1920 |
| aatgaaggat | tcggaaaccc | tgaagccaga | taattttgaa | gaatctggct | atacattcat | 1980 |
| agcaccaaga | gattactgca | atgacctgaa | aaatatcggat | aataaactg | aatttctttt | 2040 |
| aaatttcaac | gagtttattg | atagaaaaac | tccaaacaac | ccatcatgta | acgcggattt | 2100 |

-continued

```
gattaatagc gtcttgcttg atgcaggctt tacaaatgaa cttgtccaaa attactggag    2160
taagcagaaa aatatcaagg gagtgaaagc acgatttgtt gtgactgatg gtgggattac    2220
cagagtttat cccaaagagg ctggagaaaa ttggcaagaa acccagaga catatgagga    2280 cagcttctat aaaaggagcc tagataatga taactatgtt ttcactgctc cctactttaa    2340
caaaagtgga cctggtgcct atgaatcggg cattatggta agcaaagctg tagaaatata    2400
tattcaaggg aaacttctta aacctgcagt tgttggaatt aaaattgatg taaattcctg    2460
gatagagaat tcaccaaaa cctcaatcag agatccgtgt gctggtccag tttgtgactg    2520
caaaagaaac agtgacgtaa tggattgtgt gattctggat gatggtgggt tcttctgat    2580 ggcaaatcat gatgattata ctaatcagat tggaagattt tttggagaga ttgatcccag    2640
cttgatgaga cacctggtta atatatcagt ttatgctttt aacaaatctt atgattatca    2700
gtcagtatgt gagcccggtg ctgcaccaaa acaaggagca ggacatcgct cagcatatgt    2760
gccatcagta gcagacatat acaaattggc tggtgggcc actgctgctg cctggtctat    2820
tctacagcag tttctcttga gtttgacctt tccacgactc cttgaggcag ttgagatgga    2880
ggatgatgac ttcacggcct ccctgtccaa gcagagctgc attactgaac aaacccagta    2940
tttcttcgat aacgacagta aatcattcag tggtgtatta gactgtggaa actgttccag    3000
aatctttcat ggagaaaagc ttatgaacac caacttaata ttcataatgg ttgagagcaa    3060
agggacatgt ccatgtgaca cacgactgct catacaagcg gagcagactt ctgacggtcc    3120
aaatccttgt gacatggtta agcaacctag ataccgaaaa gggcctgatg tctgctttga    3180
taacaatgtc ttggaggatt atactgactg tggtggtgtt tctggattaa atccctccct    3240
gtggtatatc attggaatcc agtttctact actttggctg gtatctggca gcacacaccg    3300
gctgttatga ccttctaaaa accaaatctg catagttaaa ctccagaccc tgccaaaaca    3360
tgagccctgc cctcaattac agtaacgtag ggtcagctat aaaatcagac aaacattagc    3420
tgggcctgtt ccatggcata acactaaggc gcagactcct aaggcaccca ctggctgcat    3480
gtcagggtgt cagatcctta aacgtgtgtg aatgctgcat catctatgtg taacatcaaa    3540
gcaaaatcct atacgtgtcc tctattggaa aatttgggcg tttgttgttg cattgttggt    3600
```

```
<210> SEQ ID NO 19
<211> LENGTH: 3055
<212> TYPE: DNA
<213> ORGANISM: Homo sapiens

<400> SEQUENCE: 19
```

```
atggctgctg gctgcctgct ggccttgact ctgacacttt tccaatcttt gctcatcggc     60
ccctcgtcgg aggagccgtt cccttcggcc gtcactatca aatcatgggt ggataagatg    120
caagaagacc ttgtcacact ggcaaaaaca gcaagtggag tcaatcagct tgttgatatt    180
tatgagaaat atcaagattt gtatactgtg aaccaaaata tgcacgcca gctggtagaa    240 attgcagcca gggatattga gaaacttctg agcaacagat ctaaagccct ggtgagcctg    300
gcattggaag cggagaaagt tcaagcagct caccagtgga gagaagattt tgcaagcaat    360
gaagttgtct actacaatgc aaaggatgat ctcgatcctg agaaaaatga cagtgagcca    420
ggcagccaga ggataaaacc tgttttcatt gaagatgcta attttggacg acaaatatct    480
tatcagcacg cagcagtcca tattcctact gacatctatg agggctcaac aattgtgtta    540
aatgaactca actggacaag tgccttagat gaagttttca aaaagaatcg cgaggaagac    600
ccttcattat tgtggcaggt ttttggcagt gccactggcc tagctcgata ttatccagct    660
```

-continued

```
tcaccatggg ttgataatag tagaactcca aataagattg acctttatga tgtacgcaga      720
agaccatggt acatccaagg agctgcatct cctaaagaca tgcttattct ggtggatgtg      780
agtggaagtg ttagtggatt gacacttaaa ctgatccgaa catctgtctc cgaaatgtta      840
gaaaccctct cagatgatga tttcgtgaat gtagcttcat ttaacagcaa tgctcaggat      900
gtaagctgtt ttcagcacct tgtccaagca aatgtaagaa ataaaaaagt gttgaaagac      960
gcggtgaata atatcacagc caaggaatt acagattata agaagggctt tagttttgct     1020
tttgaacagc tgcttaatta taatgttttcc agagcaaact gcaataagat tattatgcta     1080
ttcacggatg gaggagaaga gagagcccag gagatattta caaatacaa taaagataaa      1140
aaagtacgtg tattcaggtt ttcagttggt caacacaatt atgagagagg acctattcag      1200
tggatggcct gtgaaaacaa aggttattat tatgaaattc cttccattgg tgcaataaga      1260
atcaatactc aggaatattt ggatgttttg gaagaccaa tggttttagc aggagacaaa      1320
gctaagcaag tccaatggac aaatgtgtac ctggatgcat tggaactggg acttgtcatt      1380
actggaactc ttccggtctt caacataacc ggccaatttg aaaataagac aaacttaaag      1440
aaccagctga ttcttggtgt gatgggagta gatgtgtctt tggaagatat taaaagactg      1500
acaccacgtt ttacactgtg ccccaatggg tattactttg caatcgatcc taatggttat      1560
gttttattac atccaaatct tcagccaaag aaccccaaat ctcaggagcc agtaacattg      1620
gatttccttg atgcagagtt agagaatgat attaaagtgg agattcgaaa taagatgatt      1680
gatggggaaa gtggagaaaa aacattcaga actctggtta aatctcaaga tgagagatat      1740
attgacaaag gaaacaggac atacacatgg acacctgtca atggcacaga ttacagtttg      1800
gccttggtat taccaaccta cagtttttac tatataaaag ccaaactaga agagacaata      1860
actcaggcca gatcaaaaaa gggcaaaatg aaggattcgg aaaccctgaa gccagataat      1920
tttgaagaat ctggctatac attcatagca ccaagagatt actgcaatga cctgaaaata      1980
tcggataata acactgaatt tcttttaaat ttcaacgagt ttattgatag aaaaactcca      2040
aacaacccat catgtaacgc ggatttgatt aatagagtct tgcttgatgc aggctttaca      2100
aatgaacttg tccaaaatta ctggagtaag cagaaaaata tcaagggagt gaaagcacga      2160
tttgttgtga ctgatggtgg gattaccaga gtttatccca agaggctgg agaaaattgg       2220
caagaaaaacc cagagacata tgaggacagc ttctataaaa ggagcctaga taatgataac      2280
tatgttttca ctgctcccta ctttaacaaa agtggacctg gtgcctatga atcgggcatt      2340
atggtaagca agctgtaga aatatatatt caagggaaac ttcttaaacc tgcagttgtt      2400
ggaattaaaa ttgatgtaaa ttcctggata gagaatttca ccaaaacctc aatcagagat      2460
ccgtgtgctg gtccagtttg tgactgcaaa agaaacagtg acgtaatgga ttgtgtgatt      2520
ctggatgatg tgggtttct tctgatggca aatcatgatg attatactaa tcagattgga      2580
agattttttg gagagattga tcccagcttg atgagacacc tggttaatat atcagtttat      2640
gcttttaaca aatcttatga ttatcagtca gtatgtgagc ccggtgctgc accaaaacaa      2700
ggagcaggac atcgctcagc atatgtgcca tcagtagcag acatattaca aattggctgg      2760
tgggccactg ctgctgcctg gtctattcta cagcagtttc tcttgagttt gacctttcca      2820
cgactccttg aggcagttga gatggaggat gatgacttca cggcctccct gtccaagcag      2880
agctgcatta ctgaacaaac ccagtatttc ttcgataacg acagtaaatc attcagtggt      2940
gtattagact gtggaaactg ttccagaatc tttcatggag aaaagcttat gaacaccaac      3000
```

-continued

| | |
|---|---:|
| ttaatattca taatggttga gagcaaaggg acatgtccat gtgacacacg actgc | 3055 |

<210> SEQ ID NO 20
<211> LENGTH: 3109
<212> TYPE: DNA
<213> ORGANISM: Homo sapiens

<400> SEQUENCE: 20

| | |
|---|---:|
| atggctgctg gctgcctgct ggccttgact ctgacactt tccaatcttt gctcatcggc | 60 |
| ccctcgtcgg aggagccgtt cccttcggcc gtcactatca aatcatgggt ggataagatg | 120 |
| caagaagacc ttgtcacact ggcaaaaaca gcaagtggag tcaatcagct tgttgatatt | 180 |
| tatgagaaat atcaagattt gtatactgtg aaccaaata atgcacgcca gctggtagaa | 240 |
| attgcagcca gggatattga aaacttctg agcaacagat ctaaagccct ggtgagcctg | 300 |
| gcattggaag cggagaaagt tcaagcagct caccagtgga gagaagattt tgcaagcaat | 360 |
| gaagttgtct actacaatgc aaaggatgat ctcgatcctg agaaaaatga cagtgagcca | 420 |
| ggcagccaga ggataaaacc tgttttcatt gaagatgcta attttggacg acaaatatct | 480 |
| tatcagcacg cagcagtcca tattcctact gacatctatg agggctcaac aattgtgtta | 540 |
| aatgaactca actggacaag tgccttagat gaagttttca aaagaatcg cgaggaagac | 600 |
| ccttcattat tgtggcaggt ttttggcagt gccactggcc tagctcgata ttatccagct | 660 |
| tcaccatggg ttgataatag tagaactcca aataagattg acctttatga tgtacgcaga | 720 |
| agaccatggt acatccaagg agctgcatct cctaaagaca tgcttattct ggtggatgtg | 780 |
| agtggaagtg ttagtggatt gacacttaaa ctgatccgaa catctgtctc gaaatgtta | 840 |
| gaaaccctct cagatgatga tttcgtgaat gtagcttcat taacagcaa tgctcaggat | 900 |
| gtaagctgtt ttcagcacct tgtccaagca aatgtaagaa ataaaaagt gttgaaagac | 960 |
| gcggtgaata tatcacagc caaggaatt acagattata gaagggctt tagttttgct | 1020 |
| tttgaacagc tgcttaatta taatgtttcc agagcaaact gcaataagat tattatgcta | 1080 |
| ttcacggatg gaggagaaga gagagcccag gagatattta caaatacaa taagataaaa | 1140 |
| aaagtacgtg tattcaggtt ttcagttggt caacacaatt atgagagagg acctattcag | 1200 |
| tggatggcct gtgaaaacaa aggttattat tatgaaattc cttccattgg tgcaataaga | 1260 |
| atcaatactc aggaatattt ggatgttttg ggaagaccaa tggttttagc aggagacaaa | 1320 |
| gctaagcaag tccaatggac aaatgtgtac ctggatgcat tggaactggg acttgtcatt | 1380 |
| actggaactc ttccggtctt caacataacc ggccaatttg aaaataagac aaacttaaag | 1440 |
| aaccagctga ttcttggtgt gatgggagta gatgtgtctt ggaagatat aaaagactg | 1500 |
| acaccacgtt ttcactgtg ccccaatggg tattacttg caatcgatcc taatggttat | 1560 |
| gttttattac atccaaatct tcagccaaag aaccccaaat ctcaggagcc agtaacattg | 1620 |
| gatttccttg atgcagagtt agaaatgat attaaagtgg agattcgaaa taagatgatt | 1680 |
| gatgggaaa gtggagaaa acattcaga actctggtta aatctcaaga tgagagatat | 1740 |
| attgacaaag aaacaggac atacacatgg acacctgtca atggcacaga ttacagtttg | 1800 |
| gccttggtat taccaaccta cagttttta tatataaaag ccaaactaga agagacaata | 1860 |
| actcaggcca gatcaaaaaa gggcaaaatg aaggattcgg aaaccctgaa gccagataat | 1920 |
| tttgaagaat ctggctatac attcatagca ccaagagatt actgcaatga cctgaaaata | 1980 |
| tcggataata acactgaatt tcttttaaat ttcaacgagt ttattgatag aaaaactcca | 2040 |
| aacaacccat catgtaacgc ggatttgatt aatagagtct tgcttgatgc aggctttaca | 2100 |

-continued

| | |
|---|---|
| aatgaacttg tccaaaatta ctggagtaag cagaaaaata tcaagggagt gaaagcacga | 2160 |
| tttgttgtga ctgatggtgg gattaccaga gtttatccca agaggctgg agaaaattgg | 2220 |
| caagaaaacc cagagacata tgaggacagc ttctataaaa ggagcctaga taatgataac | 2280 |
| tatgttttca ctgctcccta ctttaacaaa agtggacctg gtgcctatga atcgggcatt | 2340 |
| atggtaagca aagctgtaga aatatatatt caagggaaac ttcttaaacc tgcagttgtt | 2400 |
| ggaattaaaa ttgatgtaaa ttcctggata gagaatttca ccaaaacctc aatcagagat | 2460 |
| ccgtgtgctg gtccagtttg tgactgcaaa agaaacagtg acgtaatgga ttgtgtgatt | 2520 |
| ctggatgatg gtgggtttct tctgatggca aatcatgatg attatactaa tcagattgga | 2580 |
| agatttttg gagagattga tcccagcttg atgagacacc tggttaatat atcagtttat | 2640 |
| gcttttaaca aatcttatga ttatcagtca gtatgtgagc ccggtgctgc accaaaacaa | 2700 |
| ggagcaggac atcgctcagc atatgtgcca tcagtagcag acatattaca aattggctgg | 2760 |
| tgggccactg ctgctgcctg gtctattcta cagcagtttc tcttgagttt gacctttcca | 2820 |
| cgactccttg aggcagttga gatggaggat gatgacttca cggcctccct gtccaagcag | 2880 |
| agctgcatta ctgaacaaac ccagtatttc ttcgataacg acagtaaatc attcagtggt | 2940 |
| gtattagact gtggaaactg ttccagaatc tttcatggag aaaagcttat gaacaccaac | 3000 |
| ttaatattca taatggttga gagcaaaggg acatgtccat gtgacacacg actgctcata | 3060 |
| caagcggagc agacttctga cggtccaaat ccttgtgaca tggttaagc | 3109 |

<210> SEQ ID NO 21
<211> LENGTH: 3190
<212> TYPE: DNA
<213> ORGANISM: Homo sapiens

<400> SEQUENCE: 21

| | |
|---|---|
| atggctgctg gctgcctgct ggccttgact ctgacacttt tccaatcttt gctcatcggc | 60 |
| ccctcgtcgg aggagccgtt cccttcggcc gtcactatca aatcatgggt ggataagatg | 120 |
| caagaagacc ttgtcacact ggcaaaaaca gcaagtggag tcaatcagct tgttgatatt | 180 |
| tatgagaaat atcaagattt gtatactgtg gaaccaaata atgcacgcca gctggtagaa | 240 |
| attgcagcca gggatattga gaaacttctg agcaacagat ctaaagccct ggtgagcctg | 300 |
| gcattggaag cggagaaagt tcaagcagct caccagtgga gagaagattt tgcaagcaat | 360 |
| gaagttgtct actacaatgc aaaggatgat ctcgatcctg agaaaatga cagtgagcca | 420 |
| ggcagccaga ggataaaacc tgttttcatt gaagatgcta atttggacg acaaatatct | 480 |
| tatcagcacg cagcagtcca tattcctact gacatctatg agggctcaac aattgtgtta | 540 |
| aatgaactca actggacaag tgccttagat gaagttttca aaaagaatcg cgaggaagac | 600 |
| ccttcattat tgtggcaggt ttttggcagt gccactggcc tagctcgata ttatccagct | 660 |
| tcaccatggg ttgataatag tagaactcca aataagattg acctttatga tgtacgcaga | 720 |
| agaccatggt acatccaagg agctgcatct ccctaaagaca tgcttattct ggtggatgtg | 780 |
| agtggaagtg ttagtggatt gacacttaaa ctgatccgaa catctgtctc cgaaatgtta | 840 |
| gaaaccctct cagatgatga tttcgtgaat gtagcttcat ttaacagcaa tgctcaggat | 900 |
| gtaagctgtt ttcagcacct tgtccaagca aatgtaagaa ataaaaaagt gttgaaagac | 960 |
| gcggtgaata atatcacagc caaaggaatt acagattata gaagggctt tagttttgct | 1020 |
| tttgaacagc tgcttaatta taatgttttcc agagcaaact gcaataagat tattatgcta | 1080 |

-continued

```
ttcacggatg gaggagaaga gagagcccag gagatattta acaaatacaa taaagataaa    1140
aaagtacgtg tattcaggtt ttcagttggt caacacaatt atgagagagg acctattcag    1200
tggatggcct gtgaaaacaa aggttattat tatgaaattc cttccattgg tgcaataaga    1260
atcaatactc aggaatattt ggatgttttg ggaagaccaa tggttttagc aggagacaaa    1320
gctaagcaag tccaatggac aaatgtgtac ctggatgcat tggaactggg acttgtcatt    1380
actggaactc ttccggtctt caacataacc ggccaatttg aaaataagac aaacttaaag    1440
aaccagctga ttcttggtgt gatgggagta gatgtgtctt tggaagatat taaaagactg    1500
acaccacgtt ttacactgtg ccccaatggg tattactttg caatcgatcc taatggttat    1560
gttttattac atccaaatct tcagccaaag aaccccaaat ctcaggagcc agtaacattg    1620
gatttccttg atgcagagtt agagaatgat attaaagtgg agattcgaaa taagatgatt    1680
gatggggaaa gtggagaaaa aacattcaga actctggtta aatctcaaga tgagagatat    1740
attgacaaag gaaacaggac atacacatgg acacctgtca atggcacaga ttacagtttg    1800
gccttggtat taccaaccta cagttttac tatataaaag ccaaactaga agagacaata    1860
actcaggcca gatcaaaaaa gggcaaaatg aaggattcgg aaaccctgaa gccagataat    1920
tttgaagaat ctggctatac attcatagca ccaagagatt actgcaatga cctgaaaata    1980
tcggataata acactgaatt tcttttaaat ttcaacgagt ttattgatag aaaaactcca    2040
aacaacccat catgtaacgc ggatttgatt aatagagtct tgcttgatgc aggctttaca    2100
aatgaacttg tccaaaatta ctggagtaag cagaaaaata tcaagggagt gaaagcacga    2160
tttgttgtga ctgatggtgg gattaccaga gtttatccca agaggctgg agaaaattgg    2220 caagaaaacc cagagacata tgaggacagc ttctataaaa ggagcctaga taatgataac    2280
tatgttttca ctgctcccta ctttaacaaa agtggacctg gtgcctatga atcgggcatt    2340
atggtaagca aagctgtaga aatatatatt caagggaaac ttcttaaacc tgcagttgtt    2400
ggaattaaaa ttgatgtaaa ttcctggata gagaatttca ccaaaacctc aatcagagat    2460
ccgtgtgctg gtccagtttg tgactgcaaa agaaacagtg acgtaatgga ttgtgtgatt    2520
ctggatgatg gtgggtttct tctgatggca aatcatgatg attatactaa tcagattgga    2580 agatttttg gagagattga tcccagcttg atgagacacc tggttaatat atcagtttat    2640
gcttttaaca aatcttatga ttatcagtca gtatgtgagc ccggtgctgc accaaaacaa    2700
ggagcaggac atcgctcagc atatgtgcca tcagtagcag acatattaca aattggctgg    2760
tgggccactg ctgctgcctg gtctattcta cagcagtttc tcttgagttt gacctttcca    2820
cgactccttg aggcagttga gatggaggat gatgacttca cggcctccct gtccaagcag    2880
agctgcatta ctgaacaaac ccagtatttc ttcgataacg acagtaaatc attcagtggt    2940
gtattagact gtgaaactg ttccagaatc tttcatggag aaaagcttat gaacaccaac    3000
ttaatattca taatggttga gagcaaaggg acatgtccat gtgacacacg actgctcata    3060
caagcggagc agacttctga cggtccaaat ccttgtgaca tggttaagca acctagatac    3120
cgaaaagggc ctgatgtctg ctttgataac aatgtcttgg aggattatac tgactgtggt    3180
ggtgtttctg                                                          3190
```

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 22
gcagatttgg ttttagaagg g　　　　　　　　　　　　　　　　　　　　21

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence:primer

<400> SEQUENCE: 23
cagaattcct catcaagaaa caccaccaca gtcggt　　　　　　　　　　　　36

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 24
ttctctaatt ctgcatcaag g　　　　　　　　　　　　　　　　　　　　21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 25
tttggatgta ataaaacata g　　　　　　　　　　　　　　　　　　　　21